(12) United States Patent
Lovell et al.

(10) Patent No.: US 9,968,574 B2
(45) Date of Patent: May 15, 2018

(54) TREATMENT OF MCI AND ALZHEIMER'S DISEASE

(75) Inventors: Mark Lovell, Mt. Vernon, KY (US); Bert Lynn, Nicholasville, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 790 days.

(21) Appl. No.: 12/949,724

(22) Filed: Nov. 18, 2010

(65) Prior Publication Data
US 2011/0118299 A1 May 19, 2011

Related U.S. Application Data

(63) Continuation-in-part of application No. 12/779,345, filed on May 13, 2010.

(60) Provisional application No. 61/216,452, filed on May 15, 2009, provisional application No. 61/234,551, filed on Aug. 17, 2009.

(51) Int. Cl.
*A01N 43/40* (2006.01)
*A61K 31/44* (2006.01)
*A61K 31/198* (2006.01)

(52) U.S. Cl.
CPC ............ *A61K 31/198* (2013.01); *A61K 31/44* (2013.01)

(58) Field of Classification Search
CPC .................................................. A61K 31/198
USPC ........................................................ 514/350
See application file for complete search history.

(56) References Cited

U.S. PATENT DOCUMENTS

| | | | |
|---|---|---|---|
| 3,917,832 A | 11/1975 | Horster | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,639,476 A | 6/1997 | Oshlack et al. | |
| 5,674,533 A | 10/1997 | Santus et al. | |
| 5,733,566 A | 3/1998 | Lewis | |
| 6,066,642 A * | 5/2000 | Jacobson et al. | 514/267 |
| 6,558,650 B1 | 5/2003 | Morton et al. | |
| 2002/0028761 A1 | 3/2002 | Koppel et al. | |
| 2008/0026405 A1 | 1/2008 | Lovell et al. | |
| 2008/0107601 A1 | 8/2008 | Lauwereys et al. | |
| 2008/0194494 A1 | 8/2008 | Martinez et al. | |
| 2010/0029654 A1 | 2/2010 | Pasinetti | |

FOREIGN PATENT DOCUMENTS

| | | | |
|---|---|---|---|
| JP | 2007/091664 A | | 4/2007 |
| JP | 2009073759 A * | | 4/2009 |
| WO | WO 9943307 A1 * | | 9/1999 |
| WO | WO 2005/051389 A1 | | 6/2005 |
| WO | WO 2005/051426 A1 | | 6/2005 |
| WO | WO 2006/109164 A2 | | 10/2006 |
| WO | WO 2007/064010 A1 | | 6/2007 |
| WO | WO 2007112288 A2 * | | 10/2007 |
| WO | WO 2008/051291 A2 | | 5/2008 |
| WO | WO 2008/109613 A1 | | 9/2008 |
| WO | WO 2009108912 A1 * | | 9/2009 |
| WO | WO 2010/034110 A1 | | 4/2010 |
| WO | WO 2010/108052 A2 | | 9/2010 |

OTHER PUBLICATIONS

Quevedo et al. (L-Type Voltage-Dependent Calcium Channel Blocker Nifedipine Enhances Memory Retention When Infused into the Hippocampus; Neurobiology of Learning and Memory vol. 69, Issue 3, May 1998, pp. 320-325).*
Harrison et al. (A Neuropsychological Test Battery for Use in Alzheimer Disease Clinical Trials. Archives of Neurology. Sep. 2007, vol. 64, No. 9).*
Näslund et al. (Correlation Between Elevated Levels of Amyloid β-Peptide in the Brain and Cognitive Decline. JAMA, the journal of the American Medical Association Mar. 22-29, 2000, vol. 283, No. 12).*
de Vries et al. (Photoreactivity and Systemic Side-Effects of Drugs Nitroaromatics (Photoreactivity of Nifedipine in vitro and in vivo) Photochem. Photobiol 62 (1995): 959-963).*
Lovell, M. A., et al. (An aberrant protein complex in CSF as a biomarker of Alzheimer disease. Neurology 70.23 (2008): 2212-2218).*
Burbach et al., "Induction of Brain-Derived Neurotrophic Factor in Plaque-Associated Gial Cells of Aged APP23 Transgenic Mice", J. Neurosci. 24(10):2421-2430 (2004).
Fahnestock et al., "Neurotrophic factors and Alzheimer's disease: are we focusing on the wrong molecule?", J. Neural. Transm. Suppl. 62:241-52 (2002).
Folstein et al., "Mini-Mental State—A practical method for grading the cognitive state of patients for the clinician", J. Psychiat. Res. 12:189-198 (1975).
Javidnia et al., "Photostability Determination of Commercially Available Nifedipine Oral Dosage Forms in Iran", Iranian J. of Pharm. Res. 2(2):111-115 (2003).
Li et al., "Impairment of long-term potentiation and spatial memory in leptin receptor-deficient rodents", Neuroscience 113(3):607-15 (2002).
Masliah et al., "PDGF is associated with neuronal and glial alterations on Alzheimer's disease", Neurobiol. Aging 16(4):549-556 (1995).
McKhann et al., "Clinical diagnosis of Alzheimer's disease: Report of the NINCDS-ADRDA work group under the auspices of Department of Health and Human Services Task Force on Alzheimer's disease", Neurology 34:939-948 (1984).

(Continued)

*Primary Examiner* — Layla Soroush
(74) *Attorney, Agent, or Firm* — Viksnins Harris Padys Malen LLP

(57) ABSTRACT

The present invention provides, among other things, therapeutic compositions and methods that can effectively treat, slow or prevent a neurological disease (e.g., a neurodegenerative disease, e.g., mild cognitive impairment (MCI) or Alzheimer's disease (AD)), in particular, based on therapeutically effective amount of nifedipine, oxidized or nitroso nifedipine derivatives, lactam (e.g., a compound of formula (Ic) or (Ic-i), e.g., NFD-L1), thyroxine (T4), triiodothyronine (T3) and combinations thereof.

22 Claims, 34 Drawing Sheets

(56) References Cited

OTHER PUBLICATIONS

New et al., "G protein-coupled receptor-induced Akt activity in cellular proliferation and apoptosis", FEBS J. 274:6025-6036 (2007).
Petersen et al., "Mild Cognitive Impairment—Clinical characterization and outcome", Arch. Neurol. 56:303-308 (1999).
Power et al., "Circulating Leptin Levels and Weight Loss in Alzheimer's Disease Patients", Dement. Geriatr. Cogn. Disord. 12(2): 167-170 (2001).
Sanna et al., "Leptin surge precedes onset of autoimmune encephalomyelitis and correlates with development of pathogenic T cell responses", J. Clin. Invest. 111(2):241-250 (2003).
Thathiah et al., "The Orphan G Protein-Coupled Receptor 3 Modulates Amyloid-Beta Peptide Generation in Neurons", Science 323:946-951 (2009).
Written Opinion for PCT/US2010/34721, dated Aug. 25, 2010.
International Search Report for PCT/US2010/34721, dated Aug. 25, 2010.
International Preliminary Report of Patentability for PCT/US2010/034721, dated Nov. 24, 2011.
Ingram et al., "Chronic Nimodipine Treatment in Aged Rats: Analysis of Motor and Cognitive Effects and Muscarinic-Induced Striatal Dopamine Release", *Neurobiology of Aging 15* (1), 55-61 (1994).
Solomon et al, "Nimodipine Facilitates Retention of the Classically Conditioned Nictitating Membrane Response in Aged Rabbits Over Long Retention Intervals", *Neurobiology of Aging 16* (5), 791-796 (1995).
European Patent Office, EP Search Report for corresponding European Application No. 10851531.3, 10 pages, dated Feb. 11, 2014.
Gorlitzer et al., "9-Chlor-3,6-diazaphenanthrene aus Nifedipin", *Arch. Pharm. 318*, 106-110 (1985).
Gorlitzer et al., "3,6-Diazaphenanthrene aus Nifedipin", *Arch. Pharm. 318*, 97-105 (1985).
Horinouchi et al., (Examination on cytoprotective effect of nifedipine metabolite), Japanese Association of Cardiovascular Pharmacology, Kouenyoushishu (Summary book), vol. 16, p. 60 (2006).
Japanese Office Action for corresponding JP Application No. 2012-511013, 10 pages, dated May 27, 2014.
Kametani et al., "Nitrenes. Part III. The Reaction of 4-(2-Nitrophenyl)pyridine Deriv-atives with Triethyl Phosphite", *J. Chem. Soc. (C)*, 138-140 (1969).
Kim, "Rearrangements of 4-(2-Aminophenyl)-1,4-dihydro-2,6-dimethyl-3,5-pyridinedicarboxylic acid diethyl ester", *J. Heterocyclic Chem. 23*, 1471-1474 (1986).
Ogawa et al., "Photostability Nifedipine in Powder, Obtained by Crushing Tablet, Granule or Fine-Grnaule", Byouinn Yakugaku (Hospital Pharmacy), vol. 16 (3), 189-197 (1990). [English Abstract included.].
Patent Cooperation Treaty, International Searching Authority, Written Opinion and Search Report for PCT/US2010/057287, 15 pages, dated Jan. 21, 2011.
Petrow, "New Syntheses of Heterocyclic Compounds. Part VIII. The Schmidt Rearrangement of 1: 3-Dimethyl-2-azafluorenones (continued)", *Journal of the Chemical Society, Chemical Society*, pp. 888-891 (1946).
Pietta et al., "High-performance liquid chromatography of nifedipine, its metabolites and photochemical degradation products", Journal of Chromatography 210(3), 516-521 (1981).
Savigni et al., "Iron and transition metal transport into erythrocytes mediated by nifedipine degradation products and related compounds", *Biochemical Pharmacology 65*, 1215-1226 (2003).

\* cited by examiner

TREATMENT OF MCI AND ALZHEIMER'S DISEASE

REFERENCE TO RELATED APPLICATION

This application is a continuation-in-part of U.S. application Ser. No. 12/779,345, filed on May 13, 2010, which claims the benefit of U.S. Provisional Patent Application No. 61/216,452, filed May 15, 2009, and U.S. Provisional Patent Application No. 61/234,551, filed Aug. 17, 2009, both of which are hereby incorporated by reference in their entireties.

BACKGROUND OF THE INVENTION

Alzheimer's disease (AD) is a well-known but incompletely understood progressive neurodegenerative disease affecting ever-larger numbers of individuals in the aging population. Currently Alzheimer's disease affects 4 million Americans. Statistics from the National Institute on Aging estimate that there may be 14 million Americans with Alzheimer's disease by 2040 unless preventative strategies are developed.

The earliest clinical manifestation of Alzheimer's disease is described as a syndrome called Mild Cognitive Impairment (MCI). While detection of MCI may permit necessary lifestyle modifications to be planned and implemented, no therapies are currently available that forestall the progression of MCI to Alzheimer's disease or to treat Alzheimer's disease.

In 2007 testimony before the US Senate, FDA Commissioner Dr. Andrew C. von Eschenbach stated that "the estimated 4.5 million cases of Alzheimer's today can be expected to rise to about 16 million by 2050." Dr. Eschenbach explained that five drugs were approved for AD treatment—tacrine, rivastigmine, galantamine, donepezil, and memantine—the first four of which act by elevating acetylcholine levels in the brain, and the last of which is an antagonist of the N-methyl-D-aspartate receptor. Thus, Dr. Eschenbach pointed out that none of the five approved drugs have been shown to prevent or slow the underlying nerve degeneration in [AD] patients. He continued: "We await, together with the rest of the world, [ ] new drugs that may some day be able to treat the underlying cause of this insidious disease as well as other neurological diseases . . . ."

SUMMARY OF THE INVENTION

The present invention encompasses the discovery that nifedipine and its oxidized or nitroso derivatives can effectively inhibit Aβ1-40 generation, reduce Aβ processing enzymes and inactivate related biochemical pathways, both in vitro and in vivo. More surprisingly, the present inventors discovered that a lactam (e.g., a compound of formula (Ic) or (Ic-i) such as NFD-L1) can also effectively inhibit Aβ1-40 generation, reduce Aβ processing enzymes and inactivate related biochemical pathways, both in vitro and in vivo. Without wishing to be bound by any theory, it is contemplated that nitroso-nifedipine may likely be a pro-drug that converts stoichiometrically into lactam once administered in vivo. Thus, the present invention provides, among other things, novel therapeutic methods and compositions, based on nifedipine and its oxidized or nitroso derivatives, and/or lactam and its derivatives (e.g., a compound of formula (Ic) or (Ic-i), e.g., NFD-L1), that can effectively treat, slow or prevent Mild Cognitive Impairment (MCI) and/or Alzheimer's disease, as well as delaying the progression from MCI to AD.

In one aspect, the present invention provides a pharmaceutical composition suitable for treating, slowing, or preventing a neurological disease in a human subject comprising a therapeutically effective amount of one or more therapeutic agents and a pharmaceutically acceptable carrier. In some embodiments, the neurological disease is a neurodegenerative disease. In some embodiments, the neurodegenerative disease is Mild Cognitive Impairment (MCI) and/or Alzheimer's disease. In some embodiments, a therapeutic agent is of formula (Ia) as defined and described herein. In some embodiments, a therapeutic agent is of formula (Ib) as defined and described herein. In some embodiments, a therapeutic agent is of formula (Ic) as defined and described herein. In some embodiments, a therapeutic agent suitable for the invention is selected from the group consisting of nifedipine, oxidized nifedipine, nitroso-nifedipine, lactam (e.g., a compound of formula (Ic) or (Ic-i), e.g., NFD-L1), thyroxine (T4), triiodothyronine (T3) and combinations thereof. In some embodiments, a therapeutic agent suitable for the invention is a calcium channel blocker. In some embodiments, a therapeutic agent suitable for the invention is not a calcium channel blocker. In some embodiments, a therapeutic agent suitable for the invention increases calcium influx.

In some embodiments, a therapeutic agent suitable for the invention comprises nifedipine. In some embodiments, a therapeutic agent suitable for the invention comprises oxidized nifedipine. In some embodiments, a therapeutic agent suitable for the invention comprises nitroso-nifedipine. In some embodiments, a therapeutic agent suitable for the invention comprises lactam (e.g., a compound of formula (Ic) or (Ic-i), e.g., NFD-L1). In some embodiments, a therapeutic agent suitable for the invention comprises a mixture of nitroso-nifedipine, oxidized nifedipine, and nifedipine. In some embodiments, a therapeutic agent suitable for the invention comprises a mixture of nitroso-nifedipine and lactam (e.g., a compound of formula (Ic) or (Ic-i), e.g., NFD-L1). In some embodiments, a therapeutic agent suitable for the invention comprises a mixture of lactam (e.g., a compound of formula (Ic) or (Ic-i), e.g., NFD-L1), oxidized nifedipine, and nifedipine. In some embodiments, a therapeutic agent suitable for the invention comprises 55% nitroso-nifedipine, 11% oxidized nifedipine, and 34% nifedipine. In some embodiments, a therapeutic agent suitable for the invention comprises one or more (e.g., two, three, four) of lactam (e.g., a compound of formula (Ic) or (Ic-i), e.g., NFD-L1), nitroso-nifedipine, oxidized nifedipine, and nifedipine. In some embodiments, various therapeutic agents described herein further comprises thyroxine (T4) and/or triiodothyronine (T3). In some embodiments, a therapeutic agent suitable for the invention comprises nifedipine, oxidized nifedipine, nitroso-nifedipine, thyroxine (T4) and/or triiodothyronine (T3).

In some embodiments, a pharmaceutical composition according to the present invention comprises a therapeutic agent in a therapeutically effective amount of about 0.01 to about 1000 mg (e.g., about 0.01 to about 200 mg, about 0.01 to about 100 mg, about 0.1 to about 50 mg, about 0.01 to about 10 mg, about 0.01 to about 5 mg, about 0.01 to about 2.5 mg, about 0.01 to about 2.0 mg, about 0.01 to about 1.5 mg, about 0.01 to about 1.0 mg, about 0.01 to about 0.5 mg, about 0.01 to about 0.1 mg) per dose. In some embodiments, a pharmaceutical composition according to the present invention comprises nitroso-nifedipine in a therapeutically effective amount of about 10 mg to 2.5 g (e.g., about 10 mg to 2.0 g, about 10 mg to 1.5 g, about 10 to about 1000 mg, about 10 mg to about 500 mg) per dose.

In some embodiments, a pharmaceutical composition according to the present invention comprises a therapeutic agent in a therapeutically effective amount, wherein the therapeutically effective amount is insufficient to induce an adverse event in a human subject. In some embodiments, an adverse event is liver toxicity. In some embodiments, a pharmaceutical composition according to the present invention comprises a therapeutic agent in a therapeutically effective amount, wherein the therapeutically effective amount is insufficient to induce an adverse event in a human subject, wherein the agent is nitroso-nifedipine and the adverse event is liver toxicity.

In some embodiments, a pharmaceutical composition according to the present invention is formulated for oral, subcutaneous, intravenous, transdermal, intraperitoneal, intramuscular, intracerebroventricular, intraparenchymal, intrathecal, intracranial, buccal, mucosal, nasal, or rectal administration. In certain embodiments, a pharmaceutical composition according to the present invention is formulated for oral administration. In some embodiments, a pharmaceutical composition according to the invention is formulated for immediate or extended release.

In another aspect, the present invention provides a method for treating, slowing, or preventing a neurological disease in a human subject, the method comprising administering to the subject who is suffering from or susceptible to a neurological disease a therapeutic agent, such that at least one symptom or feature associated with the neurological disease is reduced in abundance, intensity, severity, or frequency, or has delayed onset. In some embodiments, a neurological disease is a neurodegenerative disorder. In some embodiments, the present invention provides a method for treating, slowing, or preventing Mild Cognitive Impairment (MCI) and/or Alzheimer's disease in a human subject, the method comprising administering to a subject who is suffering from or susceptible to MCI or Alzheimer's disease a therapeutically effective amount of one or more therapeutic agents, such that at least one symptom or feature associated with the MCI or Alzheimer's disease is reduced in abundance, intensity, severity, or frequency, or has delayed onset. In some embodiments, a symptom or feature is cognitive decline, production of amyloid beta protein, beta-secretase activity, gamma-secretase activity, paired helical filaments, phosphorylated tau protein in the brain, and/or an immune or inflammatory condition in the central nervous system. In some embodiments, an immune or inflammatory condition in the central nervous system is viral meningitis, viral encephalitis, fungal meningitis, fungal encephalitis, multiple sclerosis, schizophrenia, myasthenia gravis, or charcot joint. In some embodiments, production of amyloid beta protein comprises production of Aβ1-40. In some embodiments, production of amyloid beta protein comprises production of Aβ1-42. In some embodiments, production of amyloid beta protein is reduced by increasing an alpha-secretase activity. In some embodiments, alpha-secretase activity is ADAM-10 activity. In some embodiments, the gamma-secretase activity is reduced by inhibiting presenilin-1 (PS-1), nicastrin, APH-1 and/or PEN-2 activity. In some embodiments, the gamma-secretase activity is reduced by inhibiting orphan G-coupled receptor 3 (GPCR-3) activity. In some embodiments, an immune or inflammatory condition is reduced by decreasing the level of one or more cytokines (e.g., IL-1, IL-6, TNF-α) in the central nervous system.

In some embodiments, a therapeutically effective amount of an agent according to the present invention is sufficient to increase a glutamate transporter level in the brain of a human subject. In some embodiments, a glutamate transporter level is a glial glutamate transporter EAAT2 level. In some embodiments, a therapeutically effective amount of an agent according to the present invention is insufficient to induce an adverse event in a human subject. In some embodiments, an adverse event is liver toxicity.

In some embodiments, a therapeutic agent used in a method according to the present invention is of formula (Ia) as defined and described herein. In some embodiments, a therapeutic agent used in a method according to the invention is of formula (Ib) as defined and described herein. In some embodiments, a therapeutic agent used in a method according to the invention is of formula (Ic) as defined and described herein. In some embodiments, a suitable therapeutic agent is selected from the group consisting of nifedipine, oxidized nifedipine, nitroso-nifedipine, lactam (e.g., a compound of formula (Ic) or (Ic-i), e.g., NFD-L1), thyroxine (T4), triiodothyronine (T3) and combinations thereof. In some embodiments, a suitable therapeutic agent is a calcium channel blocker. In some embodiments, a suitable therapeutic agent is not a calcium channel blocker. In some embodiments, a suitable therapeutic agent increases calcium influx.

In some embodiments, a suitable therapeutic agent comprises nifedipine. In some embodiments, a suitable therapeutic agent comprises oxidized nifedipine. In some embodiments, a suitable therapeutic agent comprises nitroso-nifedipine. In some embodiments, a suitable therapeutic agent comprises lactam (e.g., a compound of formula (Ic) or (Ic-i), e.g., NFD-L1). In some embodiments, a suitable therapeutic agent used in a method according to the present invention comprises a mixture of nitroso-nifedipine, oxidized nifedipine, and nifedipine. In some embodiments, a suitable therapeutic agent comprises a mixture of nitroso-nifedipine and lactam (e.g., a compound of formula (Ic) or (Ic-i), e.g., NFD-L1). In some embodiments, a suitable therapeutic agent comprises a mixture of lactam (e.g., a compound of formula (Ic) or (Ic-i, e.g., NFD-L1), oxidized nifedipine, and nifedipine. In some embodiments, a suitable therapeutic agent used in a method according to the present invention comprises 55% nitroso-nifedipine, 11% oxidized nifedipine, and 34% nifedipine. In some embodiments, a suitable therapeutic agent comprises one or more (e.g., two, three, four) of lactam (e.g., a compound of formula (Ic) or (Ic-i), e.g., NFD-L1), nitroso-nifedipine, oxidized nifedipine, and nifedipine. In some embodiments, suitable agents described herein further comprises T3/T4. In some embodiments, an suitable agent used in a method of the present invention comprising nifedipine, oxidized nifedipine, and/or nitroso-nifedipine further comprises thyroxine (T4) and/or triiodothyronine (T3).

In some embodiments, a method according to the present invention administers to a subject in need of treatment a therapeutic agent in a therapeutically effective amount of about 0.01 to about 1000 mg (e.g., about 0.01 to about 200 mg, about 0.01 to about 100 mg, about 0.1 to about 50 mg, about 0.01 to about 10 mg, about 0.01 to about 5 mg, about 0.01 to about 2.5 mg, about 0.01 to about 2.0 mg, about 0.01 to about 1.5 mg, about 0.01 to about 1.0 mg, about 0.01 to about 0.5 mg, about 0.01 to about 0.1 mg) per dose. In some embodiments, a method according to the present invention administers to a subject in need of treatment a therapeutic agent comprising nitroso-nifedipine in a therapeutically effective amount of about 10 mg to about 2.5 g (e.g., about 10 mg to about 2.0 g, about 10 mg to about 1.5 g, about 10 mg to about 1000 mg, or about 10 mg to about 500 mg) per dose. In some embodiments, an agent used in a method according to the present invention is administered by oral, subcutaneous, intravenous, transdermal, intraperitoneal, intramuscular, intracerebroventricular, intraparenchymal, intrathecal, intracranial, buccal, mucosal, nasal, or rectal administration. In certain embodiments, an agent used in a method according to the present invention is administered orally.

In some embodiments, according to a method of the present invention, an agent is administered monthly, bi-weekly, or weekly. In some embodiments, according to a method of the present invention, an agent is administered daily. In some embodiments, according to a method of the present invention, an agent is administered twice daily, three times daily, or four times daily.

In some embodiments, a subject treated by a method of the present invention has a diminished or elevated level of a biomarker (e.g., a protein biomarker complex) as compared to a control. In some embodiments, a suitable biomarker is a protein biomarker complex comprising at least one of a transthyretin protein and/or a prostaglandin-H2 D-isomerase protein, and at least one second, different protein selected from a transthyretin, prostaglandin-H2 D-isomerase, beta-2-microglobulin, cystatin C, superoxide dismutase [Cu—Zn], plasma retinol-binding protein, phosphatidylethanolamine-binding protein, carbonic anhydrase 2, and/or serotransferrin protein. In some embodiments, a suitable protein biomarker complex comprises prostaglandin-D2-synthase and transthyretin (PDS/TTR complex). In some embodiments, a suitable biomarker comprises one or more of (i) beta amyloid 40 (Aβ40), (ii) beta amyloid 42 (Aβ42), (iii) the ratio of Aβ40 to Aβ42, and (iv) the ratio of phosphorylated tau to total tau. In some embodiments, a biomarker is determined in a fluid sample (e.g., CSF, serum, whole blood, blood plasma, urine, ascitic fluid, saliva, tissue effusion, lavage, and combinations thereof) obtained from the subject. In some embodiments, a suitable control is indicative of a level of the biomarker in a subject selected from the group consisting of a healthy individual, a patient suffering from Alzheimer's disease with a pre-determined stage, the subject before the treatment, and combinations thereof.

In some embodiments, a subject to be treated has a test score indicative of cognitive impairment. In some embodiments, a test score indicative of cognitive impairment is an MMSE score (e.g., lower than 27, e.g., 21-26). In some embodiments, a test score indicative of cognitive impairment is a CDR score (e.g., above 0, e.g., 0.5, e.g., 1).

In some embodiments, a method according to the invention further includes a step of first determining the therapeutically effective amount of the therapeutic agent based on the level of a biomarker and/or a cognitive test score.

In yet another aspect, the invention provides a solid oral dosage form comprising nitroso-nifedipine and nifedipine, and wherein the mass ratio of nitroso-nifedipine to nifedipine is at least about 1:1 (e.g., at least about 2:1, at least about 4:1, at least about 8:1, at least about 16:1, at least about 32:1, at least about 64:1, at least about 100:1, at least about 200:1, at least about 500:1, or at least about 1000:1). In some embodiments, a solid oral dosage form according to the present invention further comprises one or more pharmaceutically acceptable excipients (e.g., a binder, a buffer, a diluent, a dispersant, an emollient, a film-forming agent, a glidant, a light-blocking agent, a preservative, a solvent, a stabilizing agent, a surfactant, a suspending agent, and/or a tonicity agent). In some embodiments, a solid dosage form is for controlled or extended release. In some embodiments, a solid dosage form is for immediate release.

In yet another aspect, the invention provides benzo[c][2,7]naphthyridine-5(6H)-one compounds. In some embodiments, provided compounds are of the general formula (Ic):

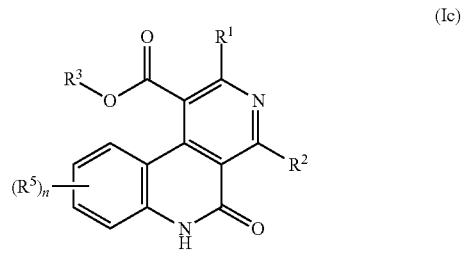

(Ic)

or a pharmaceutically acceptable salt thereof, wherein:
$R^1$ and $R^2$ are independently an optionally substituted group selected from $C_{1-6}$ aliphatic, $C_{1-6}$ heteroaliphatic, aryl, heteroaryl, or cyano;
$R^3$ is an optionally substituted group selected from $C_{1-6}$ aliphatic, $C_{1-6}$ heteroaliphatic or aryl;
$R^5$ is halogen, optionally substituted $C_{1-6}$ aliphatic, hydroxyl, alkoxy, amino, alkylamino, cyano, nitro, or nitroso; and
n is 0, 1, 2, or 3.

In certain embodiments, provided compounds are of formula (Ic-i):

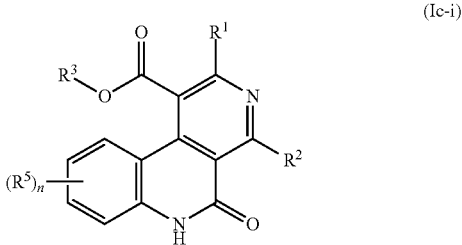

(Ic-i)

or a pharmaceutically acceptable salt thereof, wherein:
$R^1$ and $R^2$ are independently $C_{1-6}$ aliphatic or cyano;
$R^3$ is $C_{1-6}$ aliphatic;
$R^5$ is halogen, $C_{1-6}$ aliphatic, hydroxyl, alkoxy, amino, alkylamino, cyano, nitro, or nitroso; and
n is 0, 1, 2, or 3.

In certain embodiments, an inventive compound is NFD-L1.

Among other things, the present invention also provides pharmaceutical compositions containing a compound described herein (e.g., a compound of formula Ic or Ic-i) and methods of use. In some embodiments, the present invention provides a method of treating, slowing, or preventing a neurological disease in a human subject by administering to a subject who is suffering from or susceptible to a neurological disease a compound described herein (e.g., such as a compound of formula Ic or Ic-i). In some embodiments, the present invention provides a method of treating, slowing, or preventing a neurodegenerative disease in a human subject by administering to a subject who is suffering from or susceptible to a neurodegenerative disease a compound described herein (e.g., such as a compound of formula Ic or Ic-i). In some embodiments, the present invention provides a method of treating, slowing, or preventing Mild Cognitive Impairment (MCI) and/or Alzheimer's disease in a human subject by administering to a subject who is suffering from or susceptible to MCI or Alzheimer's disease a compound described herein (e.g., such as a compound of formula Ic or Ic-i). In some embodiments, the invention provides a method of inhibiting beta secretase (BACE) in a human subject comprising administering to the human subject a compound described herein (e.g., such as a compound of formula Ic or Ic-i). In some embodiments, the invention provides a method of modulating an inflammatory condition in the central nervous system of a human subject by administering to the human subject a compound described herein (e.g., such as a compound of formula Ic or Ic-i).

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

BRIEF DESCRIPTION OF THE DRAWINGS

The drawings are for illustration purposes only and not for limitation.

DEFINITIONS

Figure 1:
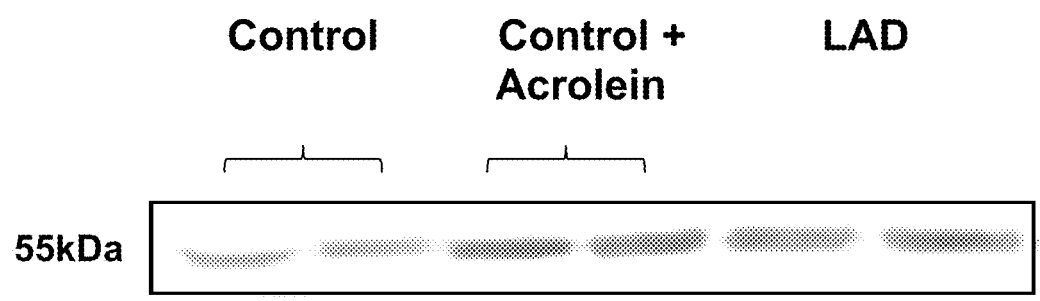
FIG. 1 illustrates an exemplary Western blot analysis of the PDS/TTR complex expressed in cell culture medium by control epithelial cells, control epithelial cells treated with acrolein, and late stage AD epithelial cells.

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., *Current Protocols in Molecular Biology*, Wiley Interscience, New York, 2001; and Sambrook et al., *Molecular Cloning: A Laboratory Manual*, $3^{rd}$ edition, Cold Spring Harbor Laboratory Press, N.Y., 2001.

In order for the present invention to be more readily understood, certain terms are first defined. Additional definitions for the following terms and other terms are set forth throughout the specification.

Alzheimer's patient: As used herein, the terms "Alzheimer's patient," "AD patient," and "individual diagnosed with AD" all refer to an individual who has been diagnosed with AD or has been given a probable diagnosis of Alzheimer's Disease (AD).

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biological fluid sample: As used herein, the term "biological fluid sample" encompasses a variety of fluid sample types obtained from an individual and can be used in a diagnostic or monitoring assay. The term encompasses whole blood, blood serum or blood plasma, cerebrospinal fluid (CSF), urine and other liquid samples of biological origin. The term also includes samples that have been manipulated in any way after their procurement, such as by treatment with reagents, solubilization, or enrichment for certain components, such as proteins or polynucleotides.

Combination therapy: The term "combination therapy", as used herein, refers to those situations in which two or more different pharmaceutical agents are administered in overlapping regimens so that the subject is simultaneously exposed to both agents.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Dosing regimen: A "dosing regimen", as that term is used herein, refers to a set of unit doses (at least one and often more than one) that are administered individually separated by periods of time. The recommended set of doses (i.e., amounts, timing, route of administration, etc.) for a particular therapeutic agent constitutes its dosing regimen.

Functional: As used herein, a "functional" biological molecule is a biological molecule in a form in which it exhibits a property and/or activity by which it is characterized.

Inhibition: As used herein, the terms "inhibition," "inhibit" and "inhibiting" refer to processes or methods of decreasing or reducing activity and/or expression of a protein or a gene of interest. Typically, inhibiting a protein or a gene refers to reducing expression or a relevant activity of the protein or gene by at least 10% or more, for example, 20%, 30%, 40%, or 50%, 60%, 70%, 80%, 90% or more, or a decrease in expression or the relevant activity of greater than 1-fold, 2-fold, 3-fold, 4-fold, 5-fold, 10-fold, 50-fold, 100-fold or more as measured by one or more methods described herein or recognized in the art.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism such as a non-human animal.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Individual with MCI: As used herein, "an individual with MCI (mild cognitive impairment)" is typically an individual who meets the following clinical criteria of amnestic MCI (Petersen et al. Arch Neurol 56:303-308 (1999): 1) memory complaints corroborated by an informant, 2) objective memory impairment for age and education, 3) normal general cognitive function, 4) intact activities of daily living, and 5) the subject does not meet criteria for dementia.

Individual with EAD: As used herein, an "individual with EAD (early or moderate Alzheimer's disease)" is an individual who demonstrate the following criteria: 1) a decline in cognitive function for a previous higher level, 2) declines in one or more areas of cognition in addition to memory, 3) a clinical dementia rating scale score of 0.5 to 1, and 4) a clinical examination that excluded other causes of dementia.

Individual with LAD: As used herein, an "individual with LAD (severe or late stage Alzheimer's disease)" is an individual who meets the standard clinical diagnostic criteria for probable AD (McKhann et al. Neurology 34:939-48 (1984).

Lactam: As used herein, a "lactam" is a cyclic amide. Typically, prefixes indicate how many carbon atoms (apart from the carbonyl moiety) are present in the ring: β-lactam (2 carbon atoms outside the carbonyl, 4 ring atoms in total), γ-lactam (3 and 5), δ-lactam (4 and 6). In some embodiment, a lactam suitable for the invention is defined by formula (Ic) or formula (Ic-i). In some embodiments, a lactam suitable for the invention is NFD-L1.

Reference value: As used herein, a "reference value" can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the individual with AD, MCI or cognitive impairment, but at an earlier point in time, or a value obtained from a sample from an AD patient other than the individual being tested, or a "normal" individual, that is an individual not diagnosed with AD. The reference value can be based on a large number of samples, such as from AD patients or normal individuals or based on a pool of samples including or excluding the sample to be tested.

Neurological disease: As used herein, the phrase "neurological disease" refers to a disease or disorder of the central nervous system. Neurological diseases include multiple sclerosis, neuropathies, and neurodegenerative disorders such as AD, Parkinson's disease, amyotrophic lateral sclerosis (ALS), Huntington's disease, mild cognitive impairment (MCI) and frontotemporal dementia. Additional exemplary neurological diseases include epilepsy, convulsive disorder, pain, anxiety, depression, schizophrenia, post-anesthesia cognitive decline, opioid tolerance, drug abuse, alcohol abuse, schizophrenia, neuroleptic malignant syndrome, Tourette's syndrome, Pick's Disease, dementia, delirium, neurodegeneration in Down Syndrome, Familial British Dementia, Familial Danish Dementia, Korsakoffs disease, olivopontocerebellar atrophy, HIV-induced dementia and blindness, multi-infarct dementia, hereditary motor and sensory neuropathies (HMSN, also known as peroneal muscular atrophy or Charcot-Marie-Tooth disease), diabetic polyneuropathy, olivopontocerebellar atrophy, age-onset neurological deterioration, alcoholic polyneuropathy, tinnitus, and pathophysiologically symptomology.

Normal individual: As used herein, a "Normal" individual or "healthy" individual refers to an individual who has or would be assessed by a physician as not having AD or MCI, and has an Mini-Mental State Examination (MMSE) (referenced in Folstein et al., J. Psychiatr. Res 1975; 12:1289-198) score or would achieve a MMSE score in the range of 25-30. A "Normal" individual is generally age-matched within a range of 5 to 10 years, including but not limited to an individual that is age-matched, with the individual to be assessed.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, etc. In some embodiments, proteins may comprise natural amino acids, non-natural amino acids, synthetic amino acids, and combinations thereof. The term "peptide" is generally used to refer to a polypeptide having a length of less than about 100 amino acids.

Subject: As used herein, the term "subject" or "patient" refers to any organism to which compositions in accordance with the invention may be administered, e.g., for experimental, diagnostic, prophylactic, and/or therapeutic purposes. Typical subjects include animals (e.g., mammals such as mice, rats, rabbits, non-human primates, and humans; insects; worms; etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition.

Therapeutic agent: As used herein, the phrase "therapeutic agent" refers to any agent that, when administered to a subject, has a therapeutic effect and/or elicits a desired biological and/or pharmacological effect. As used herein, the terms "therapeutic agent" and "agent" are used inter-changeably.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Aliphatic: The term "aliphatic" or "aliphatic group", as used herein, denotes a hydrocarbon moiety that may be straight-chain (i.e., unbranched), branched, or cycloaliphatic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl: The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

Alkyl: The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl: The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

Amino: The term "amino," as used herein, refers to a group of the formula ($-NH_2$).

Alkoxy: The term "alkoxy" refers to a "substituted hydroxyl" of the formula ($-OR^i$), wherein $R^i$ is an alkyl group, as defined herein, and the oxygen moiety is directly attached to the parent molecule.

Alkylamino: The term "alkylamino" refers to a "substituted amino" of the formula ($-NR^h_2$), wherein $R^h$ is, independently, a hydrogen or an alkyl group, as defined herein, and the nitrogen moiety is directly attached to the parent molecule.

Aryl—As used herein, the term "aryl" refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Cycloaliphatic: The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

Cyano: The term "cyano," as used herein, refers to a group of the formula ($-CN$).

Halogen: The terms "halo" and "halogen" as used herein refer to an atom selected from fluorine (fluoro, $-F$), chlorine (chloro, $-Cl$), bromine (bromo, $-Br$), and iodine (iodo, $-I$).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Nitro: The term "nitro," as used herein, refers to a group of the formula (—$NO_2$).

Nitroso: The term "nitroso," as used herein, refers to a group of the formula (—NO).

Partially unsaturated: As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

Unsaturated: The term "unsaturated", as used herein, means that a moiety has one or more units of unsaturation.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

DETAILED DESCRIPTION

The present invention provides, among other things, therapeutic compositions and methods that can effectively treat, slow or prevent mild cognitive impairment (MCI) or Alzheimer's disease (AD).

As described in the Examples section, the present invention is, in part, based on the following unexpected discoveries: (1) a protein complex PDS/TTR, known as a biomarker for early diagnosis of MCI or Alzheimer's disease, is neurotoxic and induces characteristic symptoms and features of Alzheimer's disease in cell cultures; (2) dihydropyridine calcium channel blockers (like nifedipine), their oxidized, nitroso derivatives and mixtures (which no longer function as calcium channel blockers), and/or T3/T4 effectively reduce or eliminate the ability of the PDS/TTR complex to induce AD-like symptoms and underlying enzymes and biochemical pathways in cell cultures and reduce endogenous levels of Aβ1-40 peptide in animal models; and (3) human association studies demonstrated that the use of dihydropyridine calcium channel blockers significantly delays the onset of cognitive decline thus indicating that these compounds may be used to effectively treat Alzheimer's disease. Surprisingly, the inventors found that oxidized, nitroso nifedipine derivatives and mixtures no longer function as calcium channel blockers. In some embodiments, nitroso nifedipine or a derivative thereof increases calcium influx. Without wishing to be bound by any theory, it is contemplated that the ability of these compounds to treat MCI or Alzheimer's disease may be independent of their ability to block calcium channels.

More surprisingly, the present inventors discovered that lactam such as NFD-L1 can also effectively inhibit Aβ1-40 generation, reduce Aβ processing enzymes and inactivate related biochemical pathways, both in vitro and in vivo, similar to nitroso-nifedipine. Without wishing to be bound by any theory, it is contemplated that nitroso-nifedipine may likely be a pro-drug that converts stoichiometrically into lactam once administered in vivo.

Thus, the present invention contemplates methods and compositions that can effectively treat Alzheimer's disease based on therapeutically effective amount of nifedipine, oxidized or nitroso nifedipine derivatives, lactam (e.g., a compound of formula (Ic) or (Ic-i), e.g., NFD-L1), thyroxine (T4), triiodothyronine (T3) and combinations thereof. In some embodiments, the present invention provides methods for treating, slowing, or preventing Mild Cognitive Impairment (MCI) and/or Alzheimer's disease in a human subject, comprising administering to a subject who is suffering from or susceptible to MCI or Alzheimer's disease a therapeutically effective amount of an agent selected from the group consisting of nifedipine, oxidized nifedipine, nitroso-nifedipine, lactam (e.g., a compound of formula (Ic) or (Ic-i), e.g., NFD-L1), thyroxine (T4), triiodothyronine (T3) and combinations thereof, such that at least one symptom or feature associated with the MCI or Alzheimer's disease is reduced in abundance, intensity, severity, or frequency, or has delayed onset. In some embodiments, the present invention contemplates methods and compositions that can effectively treat Alzheimer's disease based on therapeutically effective amount of a compound of formula (Ia), (Ib), (Ic), (II) and combinations thereof. In some embodiments, an agent suitable for the invention does not function as a calcium channel blocker. In some embodiments, an agent suitable for the invention increases calcium influx.

It is further contemplated that inventive methods according to the invention can be combined with sensitive biomarkers and/or cognitive test scores to identify patents, including those at an early stage of the disease, for treatment and to monitor efficacy of the treatment. Thus, the present invention is particularly useful to treat early stage patients, especially, those patients having symptoms described as Mild Cognitive Impairment (MCI) and/or to prevent progression of MCI to Alzheimer's disease.

Various aspects of the invention are described in detail in the following sections. The use of sections is not meant to limit the invention. Each section can apply to any aspect of the invention. In this application, the use of "or" means "and/or" unless stated otherwise.

Therapeutic Agents

Therapeutic agents suitable for the present invention include both calcium channel blockers (e.g., dihydropyridine calcium channel blockers such as nifedipine) and non-calcium channel blockers (e.g., oxidized nifedipine, nitroso-nifedipine, mixture of nifedipine and its derivatives, thyroxine (T4), triiodothyronine (T3)).

In some embodiments, a therapeutic agent suitable for the present invention is of formula (Ia) or (Ib):

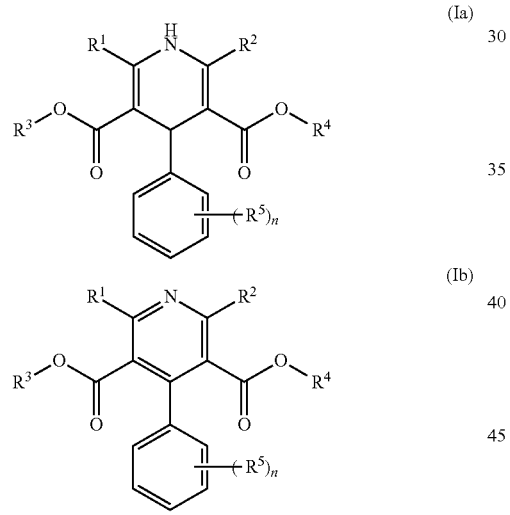

or a pharmaceutically acceptable salt thereof, wherein:
$R^1$ and $R^2$ are independently $C_{1-6}$ aliphatic or cyano;
$R^3$ and $R^4$ are independently $C_{1-6}$ aliphatic;
$R^5$ is halogen, $C_{1-6}$ aliphatic, hydroxyl, alkoxy, amino, alkylamino, cyano, nitro, or nitroso; and
n is 0, 1, 2, or 3.

In some embodiments, compounds of formula (Ia) are referred to as "reduced" or "dihydropyridines". In some embodiments, compounds of formula (Ib) are referred to as "oxidized" or "dehydro".

In some embodiments, $R^1$ and $R^2$ are independently $C_{1-3}$ alkyl. In some embodiments, $R^3$ and $R^4$ are independently $C_{1-4}$ alkyl. In some embodiments, $R^1$ and $R^2$ are methyl. In some embodiments, $R^3$ and $R^4$ are methyl.

In some embodiments, a therapeutic agent suitable for the present invention is nifedipine, oxidized nifedipine, or nitroso-nifedipine. As used herein, "nitroso-nifedipine" is an oxidized analog of nifedipine, as shown below.

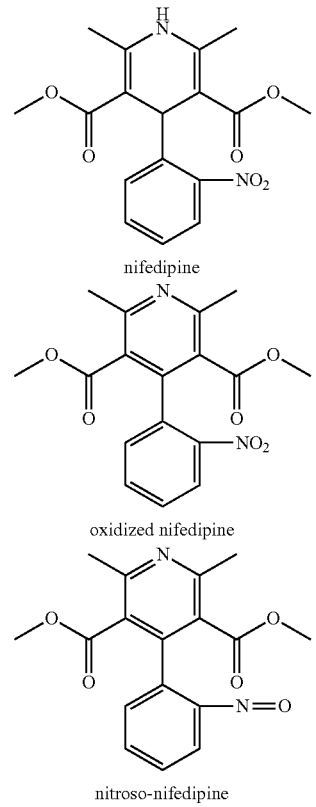

nifedipine oxidized nifedipine nitroso-nifedipine

In some embodiments, therapeutic agents suitable for the present invention include, but are not limited to, dihydropyridine compounds such as amlodipine, aranidipine, azelnidipine, barnidipine, benidipine, cilnidipine, clevidipine, efonidipine, felodipine, isradipine, lacidipine, manidipine, lercanidipine, nicardipine, nifedipine, nilvadipine, nimodipine, nisoldipine, nitrendipine, and pranidipine. In some embodiments, therapeutic agents suitable for the present invention include, but are not limited to, oxidized amlodipine, oxidized aranidipine, oxidized azelnidipine, oxidized barnidipine, oxidized benidipine, oxidized cilnidipine, oxidized clevidipine, oxidized efonidipine, oxidized felodipine, oxidized isradipine, oxidized lacidipine, oxidized manidipine, oxidized lercanidipine, oxidized nicardipine, oxidized nifedipine, oxidized nilvadipine, oxidized nimodipine, oxidized nisoldipine, oxidized nitrendipine, and oxidized pranidipine. It will be understood by one of ordinary skill in the art that an "oxidized" dihydropyridine compound (e.g., oxidized amlodipine, oxidized nimodipine, oxidized nivaldipine) is the pyridine version of said compound.

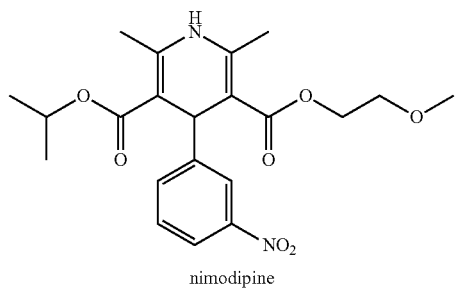

nimodipine

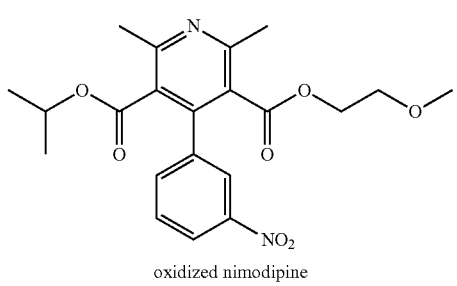
oxidized nimodipine
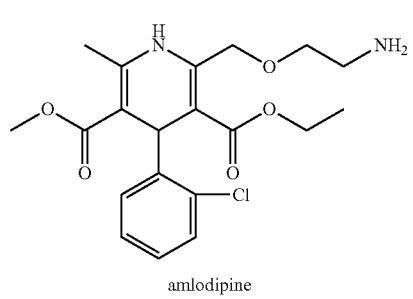
amlodipine
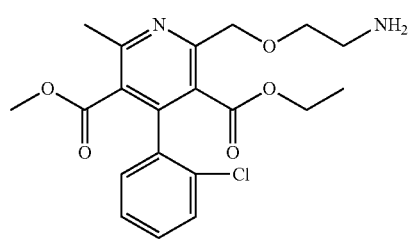
oxidized amlodipine
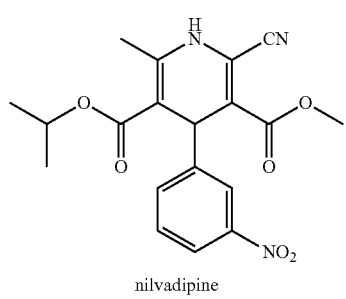
nilvadipine
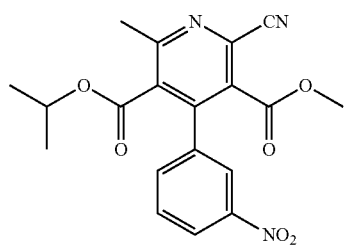
oxidized nilvadipine
Further exemplary therapeutic agents include the following:
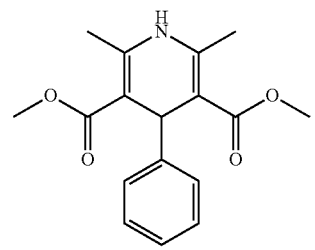
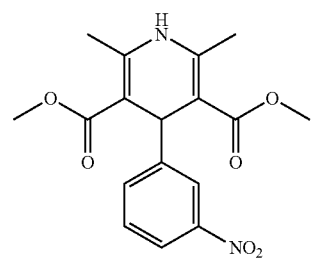
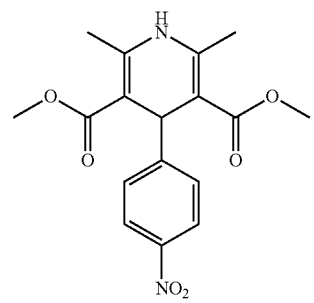
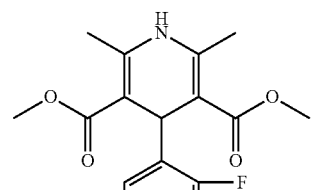
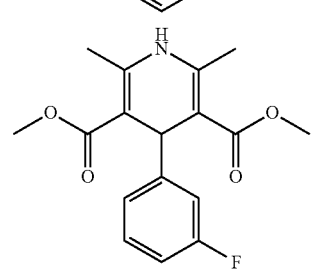
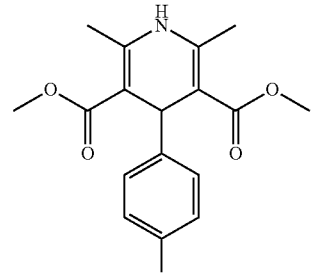

-continued

-continued
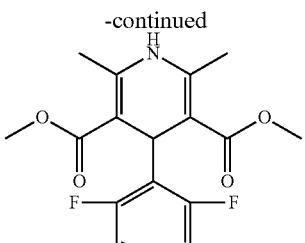
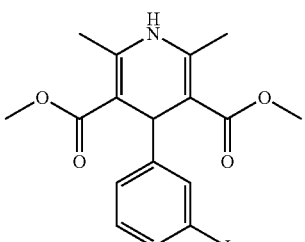
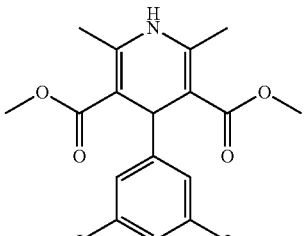
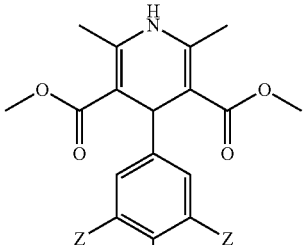
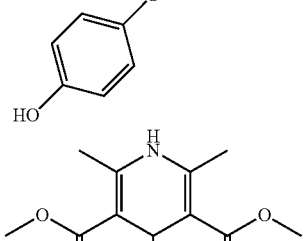
-continued
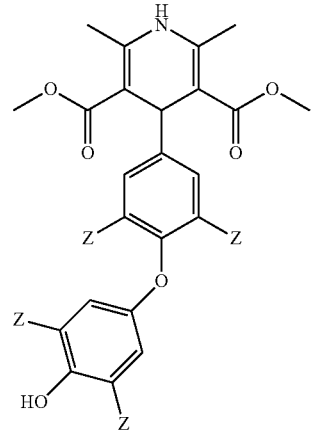
wherein Z is H, F, Cl, Br, or I;
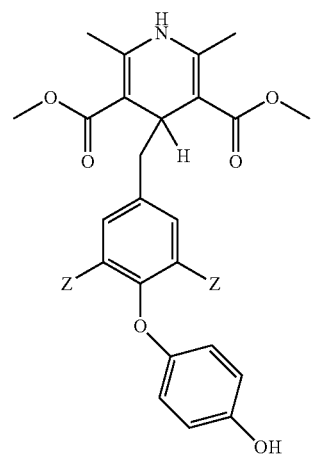
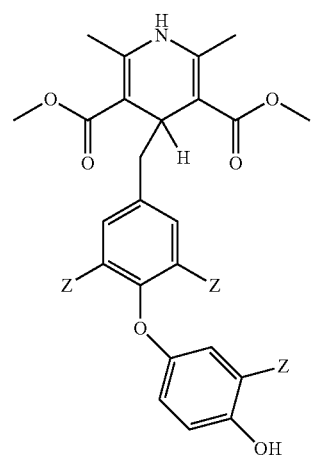

-continued

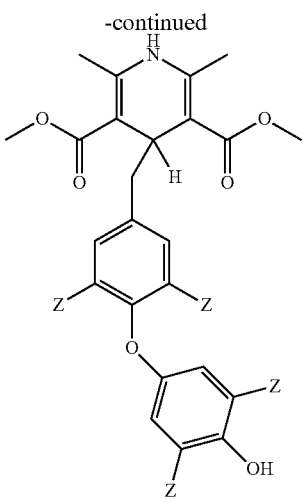

wherein Z is H, F, Cl, Br, or I.

In some embodiments, a therapeutic agent suitable for the present invention is of formula (Ic):

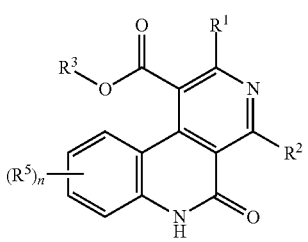

or a pharmaceutically acceptable salt thereof, wherein:

$R^1$ and $R^2$ are independently an optionally substituted group selected from $C_{1-6}$ aliphatic, $C_{1-6}$ heteroaliphatic, aryl, heteroaryl, or cyano;

$R^3$ is an optionally substituted group selected from $C_{1-6}$ aliphatic, $C_{1-6}$ heteroaliphatic or aryl;

$R^5$ is halogen, optionally substituted $C_{1-6}$ aliphatic, optionally substituted $C_{1-6}$ heteroaliphatic, hydroxyl, alkoxy, amino, alkylamino, cyano, nitro, or nitroso; and n is 0, 1, 2, or 3.

In some embodiments, a therapeutic agent suitable for the present invention is of formula (Ic-i):

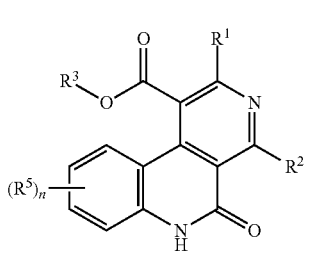

or a pharmaceutically acceptable salt thereof, wherein:

$R^1$ and $R^2$ are independently $C_{1-6}$ aliphatic or cyano;

$R^3$ is $C_{1-6}$ aliphatic;

$R^5$ is halogen, $C_{1-6}$ aliphatic, hydroxyl, alkoxy, amino, alkylamino, cyano, nitro, or nitroso; and n is 0, 1, 2, or 3.

As defined generally above, $R^1$ of formula (Ic) is an optionally substituted group selected from $C_{1-6}$ aliphatic, $C_{1-6}$ heteroaliphatic, aryl, heteroaryl, or cyano. In some embodiments, $R^1$ is substituted. In some embodiments, $R^1$ is unsubstituted. In some embodiments, $R^1$ is $C_{1-6}$ aliphatic. In some embodiments, $R^1$ is $C_{1-4}$ alkyl. In some embodiments, $R^1$ is methyl, ethyl, propyl, butyl, or isopropyl. In some embodiments, $R^1$ is methyl. In some embodiments, $R^1$ is isopropyl. In some embodiments, $R^1$ is cyano. In some embodiments, $R^1$ is $C_{1-6}$ heteroaliphatic. In some embodiments, $R^1$ is —$OCH_2CH_2NH_2$. In some embodiments, $R^1$ is aryl. In some embodiments, $R^1$ is heteroaryl.

As defined generally above, $R^2$ of formula (Ic) is an optionally substituted group selected from $C_{1-6}$ aliphatic, $C_{1-6}$ heteroaliphatic, aryl, heteroaryl, or cyano. In some embodiments, $R^2$ is substituted. In some embodiments, $R^2$ is unsubstituted. In some embodiments, $R^2$ is $C_{1-6}$ aliphatic. In some embodiments, $R^2$ is $C_{1-4}$ alkyl. In some embodiments, $R^2$ is methyl, ethyl, propyl, butyl, or isopropyl. In some embodiments, $R^2$ is methyl. In some embodiments, $R^2$ is isopropyl. In some embodiments, $R^2$ is cyano. In some embodiments, $R^2$ is $C_{1-6}$ heteroaliphatic. In some embodiments, $R^2$ is —$OCH_2CH_2NH_2$. In some embodiments, $R^2$ is aryl. In some embodiments, $R^2$ is heteroaryl.

In some embodiments, $R^1$ and $R^2$ are independently $C_{1-3}$ alkyl. In some embodiments, at least one of $R^1$ and $R^2$ is methyl. In some embodiments, $R^1$ and $R^2$ are methyl.

As defined generally above, $R^3$ of formula (Ic) is an optionally substituted group selected from $C_{1-6}$ aliphatic, $C_{1-6}$ heteroaliphatic, or aryl. In some embodiments, $R^1$ is substituted. In some embodiments, $R^1$ is unsubstituted. In some embodiments, $R^1$ is $C_{1-6}$ aliphatic. In some embodiments, $R^1$ is $C_{1-4}$ alkyl. In some embodiments, $R^1$ is methyl, ethyl, propyl, butyl, or isopropyl. In some embodiments, $R^1$ is methyl. In some embodiments, $R^1$ is isopropyl. In some embodiments, $R^1$ is ethyl. In some embodiments, $R^1$ is $C_{1-6}$ heteroaliphatic. In some embodiments, $R^1$ is —$CH_2CH_2OCH_3$. In some embodiments, $R^1$ is aryl.

As defined generally above, $R^5$ of formula (Ic) is halogen, optionally substituted $C_{1-6}$ aliphatic, optionally substituted $C_{1-6}$ heteroaliphatic, hydroxyl, alkoxy, amino, alkylamino, cyano, nitro, or nitroso. In some embodiments, $R^5$ is substituted. In some embodiments, $R^5$ is unsubstituted. In some embodiments, $R^5$ is $C_{1-6}$ aliphatic. In some embodiments, $R^5$ is $C_{1-4}$ alkyl. In some embodiments, $R^5$ is methyl, ethyl, propyl, butyl, or isopropyl. In some embodiments, $R^5$ is methyl. In some embodiments, $R^5$ is cyano. In some embodiments, $R^5$ is halogen. In some embodiments, $R^5$ is $C_{1-6}$ heteroaliphatic. In some embodiments, $R^5$ is hydroxyl. In some embodiments, $R^5$ is alkoxy. In some embodiments, $R^5$ is amino. In some embodiments, $R^5$ is alkylamino. In some embodiments, $R^5$ is nitro. In some embodiments, $R^5$ is nitroso.

As defined generally above, n of formula (Ic) is 0, 1, 2, or 3. In some embodiments, n is 0. In some embodiments, n is 1. In some embodiments, n is 2. In some embodiments, n is 3.

In some embodiments, a therapeutic agent suitable for the present invention is NFD-L1.

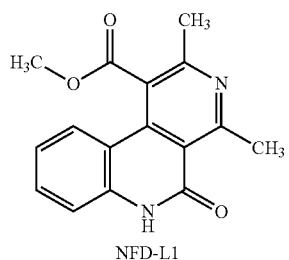 [SMILES: COC(=O)c1c(C)nc(C)c2c(=O)[nH]c3ccccc3c12]

NFD-L1

Further exemplary therapeutic agents include the following:

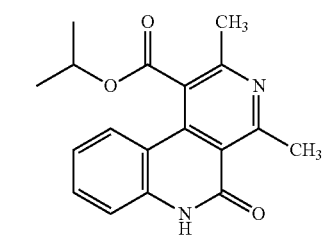

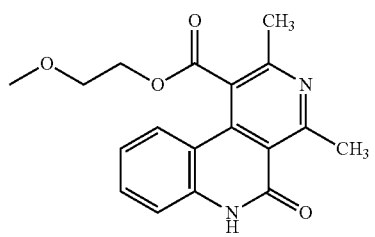

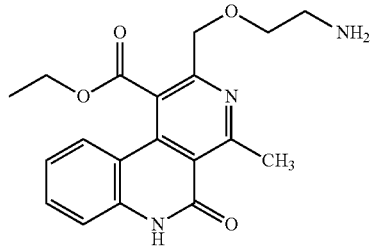

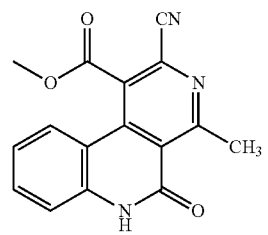

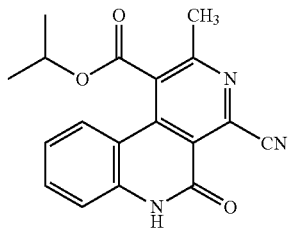

In some embodiments, a therapeutic agent suitable for the present invention is of formula (II):

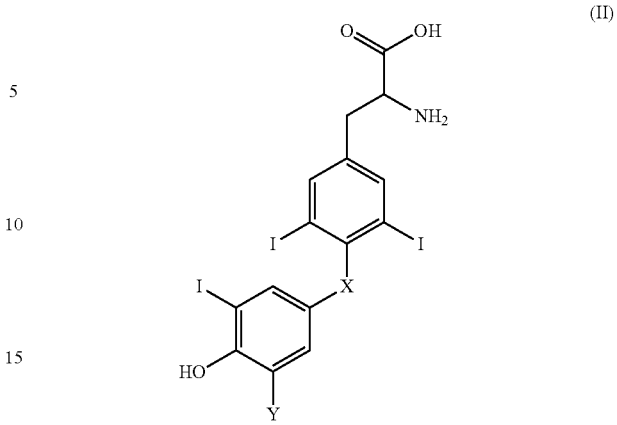

or a pharmaceutically acceptable salt thereof, wherein:
X is —CH$_2$—, —O—, or —NH—; and
Y is —H or —I.

In some embodiments, X is —CH$_2$—. In some embodiments, X is —O—. In some embodiments, X is —NH—.

In some embodiments, a therapeutic agent suitable for the present invention is thyroxine (T4) or triiodothyronine (T3):

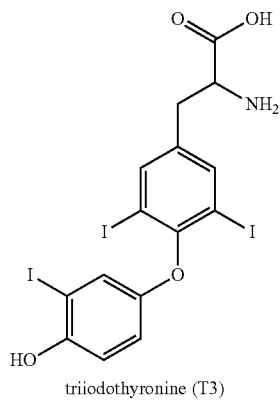

triiodothyronine (T3)

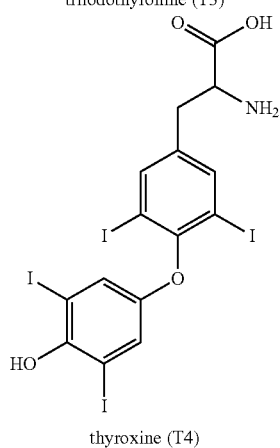

thyroxine (T4)

In some embodiments, a therapeutic agent suitable for the present invention is a mixture of various compounds described herein. For example, two or more compounds of formula (Ia) or (Ib) can be combined to form a therapeutic agent. In some embodiments, two or more of nifedipine, oxidized nifedipine, and nitroso-nifedipine are combined. In some embodiments, T3 and/or T4 are combined with one or more of nifedipine, oxidized nifedipine, and nitroso-nifedipine. In certain embodiments, nifedipine, oxidized nifedipine, and nitroso-nifedipine are combined to form a nifedipine mix or mixture.

Compounds can be mixed at various mass or molar ratios. For example, a therapeutic agent according to the invention can be a mixture of two or more of nifedipine, oxidized nifedipine, nitroso-nifedipine, NFD-L1, thyroxine (T4), and triiodothyronine (T3) at pre-determined mass or molar ratios. In some embodiments, a therapeutic agent suitable for the invention contains a mixture of nitroso-nifedipine and nifedipine. In some embodiments, nitroso-nifedipine and nifedipine can be mixed at a mass or molar ratio of about 1000:1, about 500:1, about 200:1, about 100:1, about 64:1, about 32:1, about 16:1, about 10:1, about 8:1, about 5:1, about 4:1, about 3:1, about 2:1, about 1:1, about 1:2, about 1:3, about 1:4, about 1:5, about 1:8, about 1:10, about 1:16, about 1:32, about 1:64, about 1:100, about 1:200, about 1:500, or about 1:1000. In some embodiments, nitroso-nefidipine and nifedipine can be mixed at a mass or molar ratio ranging from about 1:1000 to about 1000:1 (e.g., about 1:500 to about 500:1, about 1:200 to about 200:1, about 1:100 to about 100:1, about 1:10 to about 10:1, about 1:16 to about 16:1, about 1:32 to about 32:1, about 1:64 to about 64:1, about 1:1 to about 32:1, about 1:1 to about 10:1, about 100:1 to about 1000:1, about 10:1 to about 100:1, about 1:1000 to 1:1, about 1:1 to about 1000:1, or about 1:100 to about 1:10). In some embodiments, a therapeutic agent suitable for the invention contains a mixture of oxidized-nifedipine and nifedipine. In some embodiments, oxidized-nifedipine and nifedipine can be mixed at a mass or molar ratio of about 1000:1, about 500:1, about 200:1, about 100:1, about 64:1, about 32:1, about 16:1, about 10:1, about 8:1, about 5:1, about 4:1, about 3:1, about 2:1, about 1:1, about 1:2, about 1:3, about 1:4, about 1:5, about 1:8, about 1:10, about 1:16, about 1:32, about 1:64, about 1:100, about 1:200, about 1:500, or about 1:1000. In some embodiments, oxidized-nefidipine and nifedipine can be mixed at a mass or molar ratio ranging from about 1:1000 to about 1000:1 (e.g., about 1:500 to about 500:1, about 1:200 to about 200:1, about 1:100 to about 100:1, about 1:10 to about 10:1, about 1:16 to about 16:1, about 1:32 to about 32:1, about 1:64 to about 64:1, about 1:1 to about 32:1, about 1:1 to about 10:1, about 100:1 to about 1000:1, about 10:1 to about 100:1, about 1:1000 to 1:1, about 1:1 to about 1000:1, or about 1:100 to about 1:10). In some embodiments, a therapeutic agent suitable for the invention contains a mixture of nitroso-nifedipine and oxidized nifedipine. In some embodiments, nitroso-nifedipine and oxidized-nifedipine can be mixed at a mass or molar ratio of about 1000:1, about 500:1, about 200:1, about 100:1, about 64:1, about 32:1, about 16:1, about 10:1, about 8:1, about 5:1, about 4:1, about 3:1, about 2:1, about 1:1, about 1:2, about 1:3, about 1:4, about 1:5, about 1:8, about 1:10, about 1:16, about 1:32, about 1:64, about 1:100, about 1:200, about 1:500, or about 1:1000. In some embodiments, nitroso-nefidipine and oxidized nifedipine can be mixed at a mass or molar ratio ranging from about 1:1000 to about 1000:1 (e.g., about 1:500 to about 500:1, about 1:200 to about 200:1, about 1:100 to about 100:1, about 1:10 to about 10:1, about 1:16 to about 16:1, about 1:32 to about 32:1, about 1:64 to about 64:1, about 1:1 to about 32:1, about 1:1 to about 10:1, about 100:1 to about 1000:1, about 10:1 to about 100:1, about 1:1000 to 1:1, about 1:1 to about 1000:1, or about 1:100 to about 1:10). In some embodiments, a therapeutic agent suitable for the invention contains a mixture of nitroso-nifedipine, oxidized nifedipine, and nifedipine. In some embodiments, nitroso-nifedipine, oxidized nifedipine, and nifedipine are mixed at a mass or molar ratio of about 5:1:3, 5:2:2, 6:3:1, 10:4:1, 3:1:5, 2:5:5, or 1:1:1. In some embodiments, a therapeutic agent contains a mixture of T3 and T4. In some embodiments, T3 and T4 can be mixed at a mass or molar ratio of about 1000:1, about 500:1, about 200:1, about 100:1, about 64:1, about 32:1, about 16:1, about 10:1, about 8:1, about 5:1, about 4:1, about 3:1, about 2:1, about 1:1, about 1:2, about 1:3, about 1:4, about 1:5, about 1:8, about 1:10, about 1:16, about 1:32, about 1:64, about 1:100, about 1:200, about 1:500, or about 1:1000. In some embodiments, T3 and T4 can be mixed at a mass or molar ratio ranging from about 1:1000 to about 1000:1 (e.g., about 1:500 to about 500:1, about 1:200 to about 200:1, about 1:100 to about 100:1, about 1:10 to about 10:1, about 1:16 to about 16:1, about 1:32 to about 32:1, about 1:64 to about 64:1, about 1:1 to about 32:1, about 1:1 to about 10:1, about 100:1 to about 1000:1, about 10:1 to about 100:1, about 1:1000 to 1:1, about 1:1 to about 1000:1, or about 1:100 to about 1:10). In some embodiments, various compounds and mixtures described herein can be further combined to generate desirable therapeutic agents for the invention. For example, a T3/T4 mix can be combined with any of the nifedipine, nifedipine derivatives (e.g., oxidized or nitroso-nifedipine) or nifedipine mixtures described herein.

In some embodiments, a therapeutic agent suitable for the invention comprises a mixture of nitroso-nifedipine and lactam (e.g., a compound of formula (Ic) or (Ic-i) such as NFD-L1). In some embodiments, nitroso-nifedipine and lactam (e.g., a compound of formula (Ic) or (Ic-i) such as NFD-L1) can be mixed at a mass or molar ratio of about 1000:1, about 500:1, about 200:1, about 100:1, about 64:1, about 32:1, about 16:1, about 10:1, about 8:1, about 5:1, about 4:1, about 3:1, about 2:1, about 1:1, about 1:2, about 1:3, about 1:4, about 1:5, about 1:8, about 1:10, about 1:16, about 1:32, about 1:64, about 1:100, about 1:200, about 1:500, or about 1:1000. In some embodiments, nitroso-nefidipine and lactam (e.g., a compound of formula (Ic) or (Ic-i) such as NFD-L1) can be mixed at a mass or molar ratio ranging from about 1:1000 to about 1000:1 (e.g., about 1:500 to about 500:1, about 1:200 to about 200:1, about 1:100 to about 100:1, about 1:10 to about 10:1, about 1:16 to about 16:1, about 1:32 to about 32:1, about 1:64 to about 64:1, about 1:1 to about 32:1, about 1:1 to about 10:1, about 100:1 to about 1000:1, about 10:1 to about 100:1, about 1:1000 to 1:1, about 1:1 to about 1000:1, or about 1:100 to about 1:10). In some embodiments, a therapeutic agent suitable for the invention contains a mixture of lactam (e.g., a compound of formula (Ic) or (Ic-i) such as NFD-L1) and oxidized nifedipine. In some embodiments, lactam (e.g., a compound of formula (Ic) or (Ic-i) such as NFD-L1) and oxidized-nifedipine can be mixed at a mass or molar ratio of about 1000:1, about 500:1, about 200:1, about 100:1, about 64:1, about 32:1, about 16:1, about 10:1, about 8:1, about 5:1, about 4:1, about 3:1, about 2:1, about 1:1, about 1:2, about 1:3, about 1:4, about 1:5, about 1:8, about 1:10, about 1:16, about 1:32, about 1:64, about 1:100, about 1:200, about 1:500, or about 1:1000. In some embodiments, lactam (e.g., a compound of formula (Ic) or (Ic-i) such as NFD-L1) and oxidized nifedipine can be mixed at a mass or molar ratio ranging from about 1:1000 to about 1000:1 (e.g., about 1:500 to about 500:1, about 1:200 to about 200:1, about 1:100 to about 100:1, about 1:10 to about 10:1, about 1:16 to about 16:1, about 1:32 to about 32:1, about 1:64 to about 64:1, about 1:1 to about 32:1, about 1:1 to about 10:1, about 100:1 to about 1000:1, about 10:1 to about 100:1, about 1:1000 to 1:1, about 1:1 to about 1000:1, or about 1:100 to about 1:10). In some embodiments, a therapeutic agent suitable for the invention contains a mixture of lactam (e.g., a compound of formula (Ic) or (Ic-i) such as NFD-L1), oxidized nifedipine, and nifedipine. In some embodiments, lactam (e.g., a compound of formula (Ic) or (Ic-i) such as NFD-L1), oxidized nifedipine, and nifedipine are mixed at a mass or molar ratio of about 5:1:3, 5:2:2, 6:3:1, 10:4:1, 3:1:5, 2:5:5, or 1:1:1. In some embodiments, a therapeutic agent contains a mixture of T3 and T4. In some embodiments, T3 and T4 can be mixed at a mass or molar ratio of about 1000:1, about 500:1, about 200:1, about 100:1, about 64:1, about 32:1, about 16:1, about 10:1, about 8:1, about 5:1, about 4:1, about 3:1, about 2:1, about 1:1, about 1:2, about 1:3, about 1:4, about 1:5, about 1:8, about 1:10, about 1:16, about 1:32, about 1:64, about 1:100, about 1:200, about 1:500, or about 1:1000. In some embodiments, T3 and T4 can be mixed at a mass or molar ratio ranging from about 1:1000 to about 1000:1 (e.g., about 1:500 to about 500:1, about 1:200 to about 200:1, about 1:100 to about 100:1, about 1:10 to about 10:1, about 1:16 to about 16:1, about 1:32 to about 32:1, about 1:64 to about 64:1, about 1:1 to about 32:1, about 1:1 to about 10:1, about 100:1 to about 1000:1, about 10:1 to about 100:1, about 1:1000 to 1:1, about 1:1 to about 1000:1, or about 1:100 to about 1:10). In some embodiments, various compounds and mixtures described herein can be further combined to generate desirable therapeutic agents for the invention. For example, a T3/T4 mix can be combined with any of the nifedipine, nifedipine derivatives (e.g., oxidized or nitroso-nifedipine), compound of formula (I-c) (e.g., NFD-L1, or nifedipine mixtures described herein.

Biomarkers for Identifying Patients or Monitoring Treatment

Various biomarkers can be used to identify subject or patient who is suffering from, susceptible to or at risk of MCI or Alzheimer's disease. As used herein, a biomarker is a characteristic bio-molecule which is differentially present in a sample taken from a subject of one phenotypic status (e.g., having a disease) as compared with another phenotypic status (e.g., not having a disease). A biomarker is differentially present between different phenotypic statuses if the mean or median expression level of the biomarker in the different groups is calculated to be statistically significant. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

For example, the inventors have recently shown that levels of a ~55 kDa proteinaceous complex containing prostaglandin-D2-synthase and transthyretin (PDS/TTR complex) may serve as a sensitive and specific diagnostic biomarker of MCI and AD, as detailed in US Pat. Pub. No. 2008/0026405, which is incorporated herein by reference.

Typically, the PDS/TTR complex presents in cerebrospinal fluid and appears to be a sensitive and specific biomarker of the disease. Formation of the PDS/TTR complex was been localized to the choroid plexus, an assembly of epithelial cells located adjacent to the lateral ventricles. The choroid plexus functions as the blood-CSF barrier. The choroid plexus passes water, salts and selected small molecules from the blood to the CSF but effectively prevents blood proteins form entering the CSF. Proteins required for CSF are synthesized by the choroid plexus. Thus, the choroid plexus also functions as the source of CSF. Epithelial cells isolated from choroid plexus obtained fresh from short post mortem autopsies of late stage AD patients have been grown and expanded in culture. Examination of cell culture medium obtained from AD epithelial cells showed elevated levels of the PDS/TTR complex compared to control cells. Thus, an elevated PDS/TTR complex level as compared to a normal control can be used to identify subjects or patients suffering from, susceptible to or at risk of developing MCI or Alzheimer's disease.

In some embodiments, a biomarker suitable for the present invention comprises at least one of transthyretin and/or a prostaglandin-H2 D-isomerase, and at least one second protein selected from transthyretin, prostaglandin-H2 D-isomerase, beta-2-microglobulin, cystatin C, superoxide dismutase [Cu—Zn], plasma retinol-binding protein, phosphatidylethanolamine-binding protein, carbonic anhydrase 2 and/or serotransferrin. Mild cognitive impairment or Alzheimer's disease status is determined by correlating the obtained measurement with standards.

In some embodiments, neuronal thread protein, tau (total; T-tau and various phosphorylated forms; P-tau), and/or derivatives of amyloid precursor protein (APP) including $A\beta_{40}$ and $A\beta_{42}$, may be used as biomarkers to identify patient population for treatment with compositions and methods of the present invention. In some embodiments, a subject in need of treatment has an abnormal level of a protein biomarker complex as compared to a control, wherein the protein biomarker complex comprises one or more of (i) beta amyloid 40 ($A\beta40$), (ii) beta amyloid 42 ($A\beta42$), (iii) the ratio of $A\beta40$ to $A\beta42$, and (iv) the ratio of phosphorylated tau to total tau.

Additional biomarkers have been reported in the literature and may be used to identify patients for treatment according to the invention including, but not limited to, those described in Fahnestock et al, *J. Neural. Transm. Suppl.* 2002(62): 241-52 (2002); Masliah et al, *Neurobiol. Aging* 16(4):549-56 (1995); Power et al, *Dement. Geriatr. Cong. Disord.* 12(2):167-170 (2001); Burbach et al, *J. Neurosci.* 24(10): 2421-30 (2004), Li et al, *Neuroscience* 113(3):607-15 (2002), and Sanna et al, *J. Clin. Invest.* 111(2):241-50 (2003), each of which is incorporated herein by reference.

In some embodiments, a biomarker is determined in a fluid sample obtained from the subject. In some embodiments, a fluid sample is selected from the group consisting of CSF, serum, whole blood, blood plasma, urine, ascitic fluid, saliva, tissue effusion, lavage, and combinations thereof.

Various methods can be used to measure biomarkers qualitatively and quantitatively. For example, to detect a protein complex (such as PDS/TTR), a sandwich enzyme linked immunoassay (ELISA) cane be utilized that traps a first component of the complex (e.g., PDS) and probes for a second component (e.g. TTR). Additional exemplary methods are described in US Pat. Pub. No. 2008/0026405, which is incorporated herein by reference. Other methods are well known in the art and can be used to practice the present invention.

Typically, the measured level of a biomarker is compared to one or more controls or reference levels. Suitable reference level used for comparison with the measured level for a AD biomarker may vary, depending on aspect of the invention being practiced, as will be understood by one of ordinary skill in the art. To identify subjects suffering from or susceptible to AD or MCI, a suitable "reference level" is typically a level indicative of healthy individuals, in particular, age-matched healthy individuals. A reference level can be determined in parallel with patient sample. A reference level can also be a pre-determined level or based on historical data. For example, a suitable reference level can be an average of levels obtained from a population that is not afflicted with AD or MCI. Typically, a suitable reference level is derived from (e.g., is the mean or median of) levels obtained from an age-matched population.

Typically, a subject in need of treatment has an greater or elevated level of a biomarker described herein as compared to a control or reference level indicative of a healthy individual or population.

For treatment monitoring purposes, a suitable reference level is typically a level indicative of healthy individuals or individuals suffering from Alzheimer's disease (e.g., with a pre-determined stage, such as MCI, EAD, or LAD). A reference level can be determined in parallel with patient sample. A reference level can also be a pre-determined level or based on historical data. For example, a suitable reference level can be an average of levels obtained from a population that is not afflicted with AD or MCI, or a population that has been diagnosed with MCI or AD (e.g., EAD or LAD). Alternately, a suitable reference level may be a historical reference level for a particular patient, for example, a level that was obtained from a sample derived from the same individual, but at an earlier point in time (e.g., before the treatment or an earlier point in the treatment). Typically, a suitable reference level is derived from (e.g., is the mean or median of) levels obtained from an age-matched population.

For AD patient stratification (i.e., methods of stratifying AD patients into mild, moderate and severe stages of AD), suitable reference levels are normally derived from (e.g., is the mean or median of) levels obtained from a population which has been diagnosed with a particular stage of AD (e.g., EAD or LAD) or MCI.

In some embodiments, the level of a suitable biomarker (such as the ~55 kDa PDS/TTR complex) can be used to monitor the efficacy of the treatment. Typically, the goal of a therapy would be, ideally, to decrease, lower or diminish the level of the PDS/TTR complex in a subject so that a fluid sample taken from the subject would contain no detectable complex. A more conservative, subsidiary, goal of therapy would be to forestall any increase in the level of the ~55 kDa PDS/TTR complex. Accordingly, a person of ordinary skill in the medical therapeutic arts would be able to determine whether a given therapeutic regime is accomplishing the chosen therapeutic goal based on the level of an appropriate biomarker. In this way, a person of ordinary skill in the medical therapeutic arts would also be able to determine the effective amount of a therapeutic agent described herein based on the measured level of a suitable biomarker as compared to appropriate controls or reference levels.

Typically, aged-matched populations are used to derive various reference levels. Age-matched populations are ideally the same age as the individual being tested, but approximately age-matched populations are also acceptable. Approximately age-matched populations may be within 1, 2, 3, 4, or 5 years of the age of the individual tested, or may be groups of different ages which encompass the age of the individual being tested. Approximately age-matched populations may be in 2, 3, 4, 5, 6, 7, 8, 9, or 10 year increments (e.g. a "5 year increment" group which serves as the source for reference values for a 62 year old individual might include 58-62 year old individuals, 59-63 year old individuals, 60-64 year old individuals, 61-65 year old individuals, or 62-66 year old individuals).

The process of comparing a measured value and a reference value can be carried out in any convenient manner appropriate to the type of measured value and reference value for the AD biomarker at issue. For example, "measuring" can be performed using quantitative or qualitative measurement techniques, and the mode of comparing a measured value and a reference value can vary depending on the measurement technology employed. For example, the measured values used in the methods of the invention will most commonly be quantitative values (e.g., quantitative measurements of concentration, such as nanograms of AD biomarker per milliliter of sample, or absolute amount). As with qualitative measurements, the comparison can be made by inspecting the numerical data, by inspecting representations of the data (e.g., inspecting graphical representations such as bar or line graphs). As a non-limiting example, a measured value is generally considered to be substantially equal to or greater than a reference value if it is at least about 95% of the value of the reference value (e.g., a measured value of 1.71 can be considered substantially equal to a reference value of 1.80). A measured value is considered less or lower than a reference value if the measured value is less than 95% of the reference value (e.g., a measured value of 1.7 can be considered less than a reference value of 1.80).

Tests of Cognitive Function

Various cognitive tests may also be used to identify subject or patient who is suffering from, susceptible to or at risk of MCI or Alzheimer's disease. Two exemplary cognitive tests are the Mini Mental Status Examination (MMSE) and the Clinical Dementia Rating (CDR).

In some embodiments, an MMSE score is used to identify a subject in need of treatment with the compositions and methods described herein. An MMSE score is a composite score representing multiple tests of cognitive function. The maximum possible total MMSE score is 30 points. The MMSE can be used to classify the severity of cognitive impairment in patients with dementia or other medical conditions. Table 1 shows how MMSE scores generally represent degrees of cognitive function.

TABLE 1

| MMSE Score | Cognitive Function |
|---|---|
| 27-30 | normal cognitive function |
| 21-26 | mild cognitive impairment |
| 11-20 | moderate cognitive impairment |
| 0-10 | severe cognitive impairment |

In some embodiments, a subject in need of treatment has an MMSE score of 21-26 (mild cognitive impairment), 11-20 (moderate cognitive impairment), or 0-10 (severe cognitive impairment).

In some embodiments, a CDR score is used to identify a subject in need of treatment with the compositions and methods described herein. An CDR score is constructed from six domains that are scored individually: memory, orientation, judgment and problem solving, community affairs, home and hobbies, and personal care. Table 2 shows how CDR scores generally represent degrees of cognitive function.

TABLE 2

| MMSE Score | Cognitive Function |
|---|---|
| 0 | no cognitive impairment |
| 0.5 | very mild dementia |
| 1 | mild dementia |
| 2 | moderate dementia |
| 3 | severe dementia |

In some embodiments, a CDR score above 0 indicates that a subject may be suffering from, susceptible to or at risk of MCI or Alzheimer's disease. In some embodiments, a subject in need of treatment may have a CDR score of 0.5 (very mild dementia), 1 (mild dementia), 2 (moderate dementia), or 3 (severe dementia).

In some embodiments, a cognitive test score (such as an MMSE score or CDR score) can be used to monitor the efficacy of the treatment. Typically, an effective therapy should improve the cognitive test score. Therefore, by comparing the cognitive test scores before and after the treatment or from different time points of a treatment regimen, a person of ordinary skill in the medical therapeutic arts can determine whether a given therapeutic regime is effective. For example, a person of ordinary skill in the medical therapeutic arts would be able to determine or adjust the effective amount of a therapeutic agent described herein by based on relative cognitive test scores determined before the treatment or from different time points of a treatment regimen.

Pharmaceutical Compositions and Administration

The present invention encompasses pharmaceutical compositions comprising therapeutic agents such as those disclosed herein. In some embodiments, a pharmaceutical composition of the invention contain a therapeutically effective amount of a therapeutic agent and a pharmaceutically acceptable carrier.

As used herein, the term "pharmaceutically acceptable carrier" means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

The term "therapeutically effective amount" or simply "effective amount" of a therapeutic agent, as used herein, refers to an amount of therapeutic agent that is sufficient, when administered to a subject in need of treatment according to an appropriate regimen, to alleviate, ameliorate, stabilize, and/or delay the onset of at least one symptom or feature associated with MCI or Alzheimer's disease as well as delay in progression of one or more symptoms of MCI or Alzheimer's disease (e.g., delay in progression with respect to abundance, intensity, severity, or frequency). It will be understood, however, that the total daily usage of the therapeutic agents and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coinciding with the specific compound employed; and like factors well known in the medical arts.

In some embodiments, a therapeutically effective dose of a therapeutic agent of the present invention can range, for example, from 0.01 to 100 mg/kg body weight or more. In some embodiments, a therapeutically effective dose of a therapeutic agent of the present invention ranges from about 0.1 to about 50 mg/kg body weight (e.g., about 0.1 to about 35 mg/kg, about 0.1 to about 15 mg/kg, about 6.25 to about 35 mg/kg, about 12.5 to about 35 mg/kg, about 6.25 to about 25 mg/kg, about 35 mg/kg). In some embodiments, a therapeutically effective amount of a therapeutic agent ranges from about 0.01 mg to about 2.5 g per dose (e.g., from about 0.01 mg to about 2.0 g, from about 0.01 mg to about 1.5 g, from about 0.01 mg to about 1.0 g, per dose). In some embodiments, a therapeutically effective amount of a therapeutic agent ranges from about 0.01 to about 1000 mg (e.g., about 0.01 to about 500 mg, about 0.01 to about 250 mg, about 0.01 to about 200 mg, about 0.01 to about 150 mg, about 0.01 to about 100 mg, about 0.01 to about 50 mg, about 0.01 to about 10 mg, about 0.01 to about 5 mg, about 0.01 to about 2.5 mg, about 0.01 to about 2.0 mg, about 0.01 to about 1.5 mg, about 0.01 to about 1.0 mg, about 0.01 to about 0.5 mg, about 0.01 to about 0.1 mg) per dose. In some embodiments, the therapeutically effective amount of a therapeutic agent (in particular, nitroso-nifedipine) ranges from about 100 mg to about 5 g (e.g., about 100 mg to about 3 g, about 100 mg to about 2.5 g, about 100 mg to about 2 g, about 100 mg to about 1.5 g, about 100 mg to about 1000 mg, about 100 mg to about 500 mg, about 100 mg to about 250 mg) per dose. In some embodiments, a therapeutically effective amount of a therapeutic agent can be about 0.01 mg, about 0.05 mg, about 0.1 mg, about 0.5 mg, about 1 mg, about 5 mg, about 10 mg, about 25 mg, about 50 mg, about 100 mg, about 500 mg, about 1000 mg, about 1.5 g, about 2 g, about 2.5 g, about 3 g, or about 5 g per dose. Typically, the amount described herein is the total amount of all active compounds in a composition. For example, if a composition contains a mix of nifedipine, nitroso-nifedipine and oxidized nifedipine, a therapeutically effective amount is the combined amount of nifedipine, nitroso-nifedipine and oxidized nifedipine.

In some embodiments, a therapeutically effective amount of a therapeutic agent as described herein is an amount insufficient to induce an adverse event (e.g., liver toxicity) in a human subject.

In some embodiments, a therapeutic agent as described herein is administered once daily. In some embodiments, a therapeutic agent as described herein is administered multiple times per day, e.g., twice, three times, or four times daily. In some embodiments, a total daily dose of a therapeutic agent ranges from about 0.01 mg to about 5 g per day in multiple doses or in a single dose (e.g., from about 0.01 mg to about 4.0 g, from about 0.01 mg to about 3.0 g, from about 0.01 mg to about 2.5 g, from about 0.01 mg to about 2.0 g, from about 0.01 mg to about 1.5 g, from about 0.01 mg to about 1.0 g, per day in multiple doses or in a single dose). In some embodiments, a total daily dose of a therapeutic agent ranges from about 0.01 to about 1000 mg (e.g., about 0.01 to about 500 mg, about 0.01 to about 250 mg, about 0.01 to about 200 mg, about 0.01 to about 150 mg, about 0.01 to about 100 mg, about 0.01 to about 50 mg, about 0.01 to about 10 mg, about 0.01 to about 5 mg, about 0.01 to about 2.5 mg, about 0.01 to about 2.0 mg, about 0.01 to about 1.5 mg, about 0.01 to about 1.0 mg, about 0.01 to about 0.5 mg, about 0.01 to about 0.1 mg) per day in a single dose or in multiple doses. In some embodiments, a total daily dose of a therapeutic agent (in particular, nitroso-nifedipine) ranges from about 50 mg to about 5 g (e.g., about 50 mg to about 4 g, about 100 mg to about 3 g, about 100 mg to about 2.5 g, about 100 mg to about 2 g, about 100 mg to about 1.5 g, about 100 mg to about 1000 mg, about 100 mg to about 500 mg, about 100 mg to about 250 mg) per day in a single dose or in multiple doses. In some embodiments, a total daily dose of a therapeutic agent can be about 0.01 mg, about 0.05 mg, about 0.1 mg, about 0.5 mg, about 1 mg, about 5 mg, about 10 mg, about 25 mg, about 50 mg, about 100 mg, about 500 mg, about 1000 mg, about 1.5 g, about 2 g, about 2.5 g, about 3 g, about 3.5 g, about 4 g, about 4.5 g, or about 5 g. Typically, an amount described herein is the total amount of all active compounds in a composition. For example, if a composition contains a mix of nifedipine, nitroso-nifedipine and oxidized nifedipine, a therapeutically effective amount is the combined amount of nifedipine, nitroso-nifedipine and oxidized nifedipine.

In some embodiments, a therapeutic agent as described herein is administered monthly, bi-weekly, weekly, twice a week, or three times a week. In these instances, the daily doses described above reflects the average daily dose.

In certain situations, it may be important to maintain a fairly high dose of the active agent in the blood stream of the patient, particularly early in the treatment. Hence, at least initially, it may be important to keep the dose relatively high and/or at a substantially constant level for a given period of time, e.g., at least about six or more hours, e.g., at least about twelve or more hour, e.g., at least about twenty-four or more hours.

The compounds of the present invention may be administered alone or in combination or in concurrent therapy with other agents which affect the central or peripheral nervous system, particularly selected areas of the brain.

Pharmaceutical compositions according to the present invention may be administered by any route, including oral, subcutaneous, intravenous, intraperitoneal, intramuscular, intracerebroventricular, intraparenchymal, intrathecal, intracranial, buccal, mucosal, nasal, rectal, auricular, conjunctival, cutaneous, electro-osmosis, endocervical, endosinusial, endotracheal, enteral, epidural, extra-amniotic, extracorporeal, hemodialysis, infiltration, interstitial, intraabdominal, intra-amniotic, intra-arterial, intra-articular, intrabiliary, introbrochial, intrabursal, intracardiac, intracartilaginous, intracavitary, intracerebral, intracisternal, intracorneal, intracoronal, intracoronary, intracorporus cavernosum, intradermal, intradiscal, intraductal, intraduodenal, intradural, intraepidermal, intraesophageal, intragastric, intragingival, intraileal, intralesional, intralymphatic, intramedullary, intrameningeal, intramuscular, intraocular, intraovarian, intrapericardial, intrapleural, intraprostatic, intrapulmonary, intrasinal, intrasynovial, intratendinous, intratesticular, intrathecal, intrathroacic, intratubular, intratumor, intratympanic, intrauterine, intravascular, intravenous bolus, intravenous drip, intraventricular, intravesical, intravitreal, iontophoresis, irrigation, laryngeal, nasogastric, occlusive dressing technique, ophthalmic, oropharyngeal, parenteral, percutaneous, peridural, perineural, periodontal, respiratory, retrobulbar, soft tissue, subarachnoid, subconjunctival, sublingual, submucosal, topical, transdermal, transmucosal, transplacental, transtracheal, transtympanic, ureteral, urethral, and vaginal. In certain embodiments, a pharmaceutical composition of the present invention is administered by a route selected from oral, subcutaneous, intravenous, transdermal, intraperitoneal, intramuscular, intracerebroventricular, intraparenchymal, intrathecal, intracranial, buccal, mucosal, nasal, and rectal. In certain embodiments, a pharmaceutical composition of the present invention is administered orally.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. Depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

Solid dosage forms for oral administration include, but are not limited to, capsules, tablets, pills, powders, gelcaps and granules. In such solid dosage forms, therapeutic agent may be admixed with at least one inert diluent such as sucrose, lactose or starch. Such dosage forms may also comprise additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active compounds of this invention, excipients such as lactose, talc, silicic acid, aluminum hydroxide, calcium silicates and polyamide powder, or mixtures of these substances. Sprays can additionally contain customary propellants, such as chlorofluorohydrocarbons.

Transdermal patches can provide controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

Pharmaceutical compositions described herein can be formulated for immediate release or controlled release (also referred to as slow, sustained or extended release). Various slow or extended release formulations or devices are well known to those of ordinary skill in the art. Examples include, but are not limited to, those described in U.S. Pat. Nos. 5,674,533, 5,059,595, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art can be readily selected and adapted for use with therapeutic agents of the invention. For example, the invention encompasses solid oral dosage forms such as, but not limited to, tablets, capsules, gelcaps, and caplets that are formulated for controlled-release (i.e., slow release, extended release, or sustained release).

Advantages of controlled-release formulations include extended activity of the drug, reduced dosage frequency, and increased patient compliance. For example, controlled or extended release formulations can keep adequate dose levels constantly available inside a patient body to enhance delivery across the blood-brain barrier.

Most controlled-release formulations are designed to initially release an amount of therapeutic agent (active ingredient) that promptly produces the desired therapeutic effect, and gradually and continually release of other amounts of thug to maintain this level of therapeutic or prophylactic effect over an extended period of time. In order to maintain this constant level of drug inside the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In some embodiments, two or more therapeutic agents may be administered in combination. The two or more therapeutic agents may be administered separately from one another, as part of a multiple dosage regimen. Alternatively, those agents may be part of a single dosage form, mixed together with a compound of this invention in a single composition. If administered as part of a multiple dosage regime, the two therapeutic agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle.

The invention is provided in numerous embodiments and can be discerned, inter alia, in various examples. The following examples provide an illustrative but non-limiting description of the breadth and applicability of the invention.

EXAMPLES

Example 1. Neurotoxic Effect of PDS/TTR Complex

It has been shown that examination of cell culture medium obtained from epithelial cells derived from Alzheimer's disease patients showed elevated levels of the PDS/TTR complex compared to control cells, indicating that the PDS/TTR complex can be used as an effective biomarker for the early diagnosis of Alzheimer's disease. See, U.S. Application Pub. No. 20080026405, the disclosure of which is incorporated by reference herein. This example shows that in addition to being a biomarker for disease, the PDS/TTR complex is also neurotoxic.

First of all, it was found that acrolein (an alpha, beta unsaturated three carbon aldehydic by-product of lipid peroxidation) causes normal control epithelial cells to express the PDS/TTR complex into culture medium at comparable levels to the epithelial cells derived from Alzheimer's disease patients. For these experiments, primary cultures of choroid plexus epithelial cells were established from short post mortem interval autopsies using established methods. AD and normal control cultures were grown to confluence in MEM growth medium containing 2% fetal bovine serum and 1% epithelial growth factor (EGF). Normal control cultures were switched to Opti-MEM containing N2 supplement and were treated with vehicle (controls) or with 5 μM acrolein for 72 hours. Cultures from AD subjects were switched to N2 supplemented medium and maintained for 72 hours. After treatment, medium was collected from each flask and was desalted using PD-10 columns. The eluted proteins were then freeze-dried, resuspended in 25 μl water and analyzed using Western blot analysis and antibodies specific to PDS and TTR. FIG. 1 shows exemplary results illustrating an Western blot analysis of the PDS/TTR complex expressed in cell culture medium by control epithelial cells, control epithelial cells treated with acrolein, and epithelial cells derived from late stage Alzheimer's disease patients. As shown in FIG. 1, acrolein increased the expression of the PDS/TTR complex in control epithelial cells to a level comparable to that in late stage AD (LAD) epithelial cells.

Figure 2:
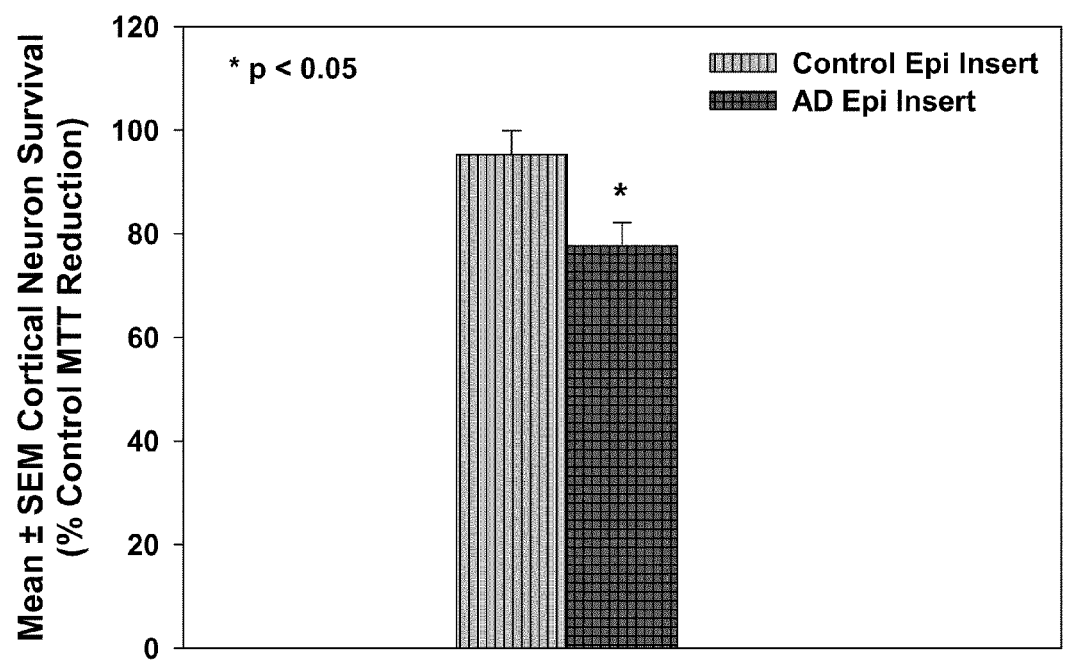
FIG. 2 illustrates exemplary survival data for cortical neurons treated with medium from control epithelial cells or AD epithelial cells.

Medium from LAD epithelial cells that contains the PDS/TTR complex was then used to treat cortical neurons. To determine if PDS/TTR complex generated by LAD choroid plexus epithelial cultures or normal control cultures treated with vehicle or with 5 μM acrolein negatively impacted primary cortical neurons, normal control epithelial cultures were switched to N2 supplemented medium and treated with vehicle alone (controls) or with 5 μM acrolein for 16 hours. LAD cultures were switched to N2 medium for 16 hours. After treatment, medium was collected from each culture type (LAD; normal controls treated with vehicle alone or normal controls treated with 5 μM acrolein) and was added to primary rat neuron cultures (7 days in culture). Primary cultures treated were subjected to the conditioned medium for 16 hours and cell viability was measured using MTT reduction assays. An exemplary result was shown in FIG. 2. As shown in FIG. 2, the survival rate for cortical neurons treated with LAD epithelial medium is significantly lower as compared to the control (FIG. 2). This experiment indicates that the PDS/TTR complex is itself neurotoxic.

Figure 3:
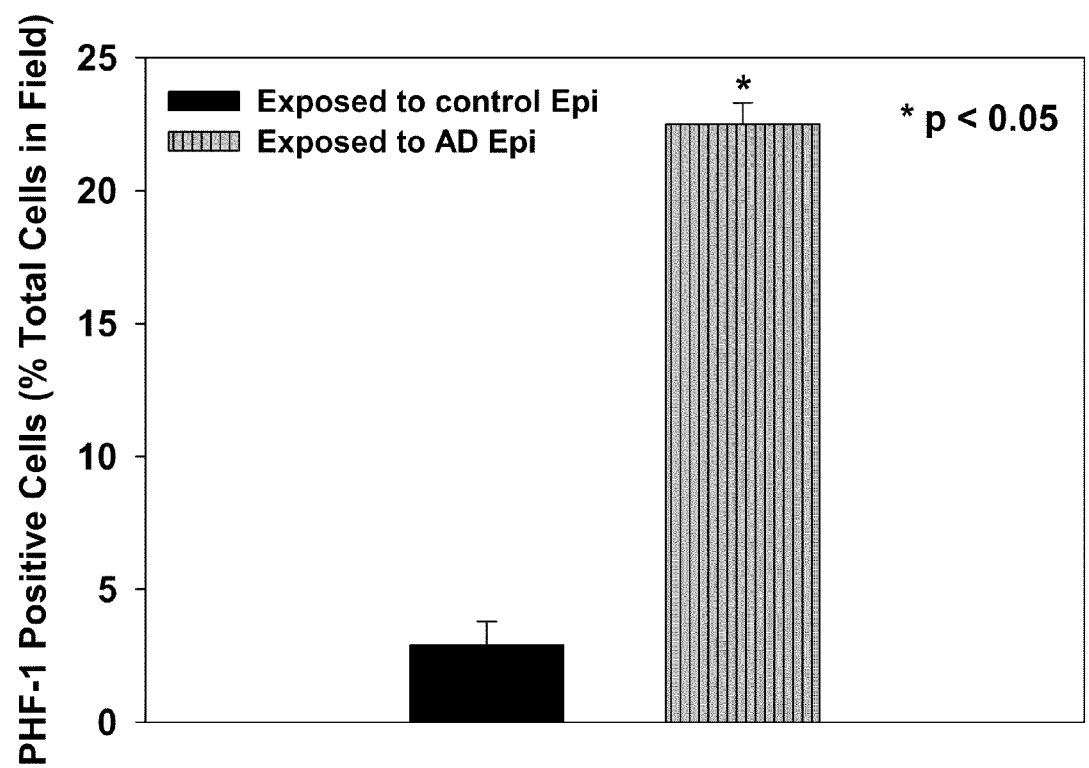
FIG. 3 illustrates exemplary results indicating that PHF1 immunopositivity was detected in SY5Y cells resulting from exposure to the PDS/TTR protein complex.

To further investigate the neurotoxic effect of the PDS/TTR complex, SY5Y neuroblastoma cells were exposed to conditioned medium from LAD or normal control epithelial cells for 16 hours. Following exposure to conditioned medium, cells were fixed in 70% methanol/30% acetone and were subjected to immunohistochemistry using anti-PHF-1 antibody. PHF-1 recognizes aberrantly phosphorylated Tau as observed in AD NFT (neurofibrillary tangles). As shown in FIG. 3, close to 25% of SY5Y cells treated with LAD epithelial cell medium are PHF-1 positive as compared to about 3% of SY5Y cells treated with control medium. Paired helical filaments are precursors to neurofibrillary tangles. Therefore, PHF1 immunopositivity is typically an indicator of the formation of late-stage neurofibrillary tangles in Alzheimer's disease. Thus, this experiment shows that the PDS/TTR complex promotes the formation of paired helical filaments in SY5Y neuroblastoma cells, indicating the PDS/TTR that complex can promote amyloid beta peptide (Aβ) generation by H4 neuroglioma cells.

To determine if the complex generated by epithelial cultures would impact inflammatory cytokine pathways, cultures of human astrocytomas were plated at a density of $2.5 \times 10^5$ cells/well and were exposed to conditioned medium for 24 hours. Following exposure medium was collected from each well and levels of inflammatory cytokines (IL-6, TNF-α, TGF-β and IL-6) were determined using commercially available ELISAs. Results of the assays showed the PDS/TTR complex activated 2 inflammatory cytokine pathways (i.e., IL-6, TNF-α) in astrocytoma cultures (data not shown), indicating a role of the PDS/TTR in neuroinflammation.

In summary, the experiments described in this example established that the PDS/TTR complex causes various biochemical changes that can directly impact hallmarks of Alzheimer's disease.

Example 2. Nifedipine, Nifedipine Analog Mix and/or T3/T4 Inhibit PDS/TTR Expression The assays described in Example 1 provide a tool to identify potential therapeutic agents that can protect neuronal cells against the PDS/TTR complex. The inventors observed that compounds such as nifedipine (1,4-dihydro-2,6-dimethyl-4-(2-nitrophenyl)-3,5-pyridinedicarboxylic acid dimethyl ester, CAS#21829-25-4 (Sigma Aldrich)), a calcium channel blocker prescribed for high blood pressure; or nifedipine analogs such as oxidized derivative of nifedipine ((2,6-dimethyl-4-(2-nitrophenyl)-3,5-pyridinedicarboxylic acid dimethyl ester, CAS#67035-22-7 (Sigma Aldrich)) or a nitroso derivative of nifedipine (2,6-dimethyl-4-(2-nitrosophenyl)-3,5-pyridinedicarboxylic acid dimethyl ester, CAS#50428-14-3 (Sigma Aldrich)), can effectively inhibit the expression of PDS/TTR complex in cell culture, individually or in combination. In addition, T3 and T4 were also evaluated and found to be effective in inhibiting the expression of PDS/TTR complex.

Figure 4:
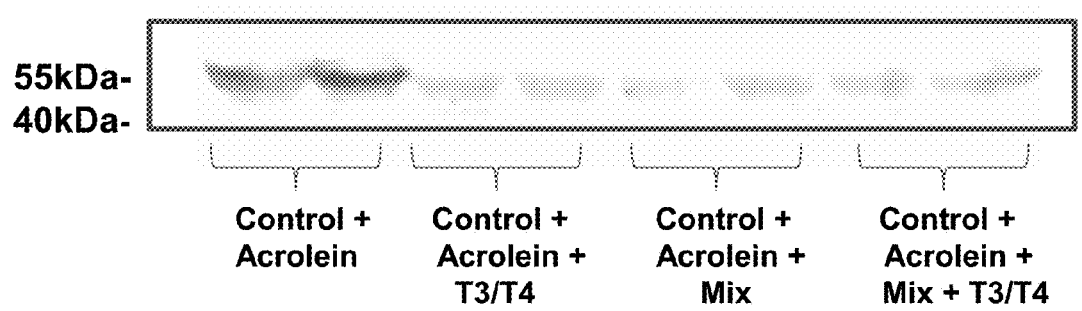
FIG. 4 illustrates exemplary Western blot data showing reduction of the PDS/TTR complex expressed by control epithelial cells treated with acrolein, acrolein plus T3/T4, acrolein plus nifedipine mixture (nitroso nifedipine 55%, oxidized nifedipine 11% and nifedipine 34%) and acrolein plus nifedipine mix and T3/T4.

Specifically, epithelial cells were treated with 5 μM acrolein, 5 μM acrolein plus 0.5 μM T3/0.5 μM T4, 5 μM acrolein plus 1 μM nifedipine mixture (nitroso-nifedipine 55%, oxidized nifedipine 11% and nifedipine 34%), or 5 μM acrolein plus 1 μM nifedipine mixture and 0.5 μM T3/0.5 μM T4, as described in Example 1. The amount of PDS/TTR secreted into the culture medium by each culture was determined by Western blot analysis as described above. Exemplary data was shown in FIG. 4. As can be seen, the amount expressed by cells treated with acrolein plus T3/T4, acrolein plus nifedipine mixture, or acrolein plus nifedipine mixture and T3/T4, was significantly less than that expressed by cells treated only with acrolein.

Figure 5:
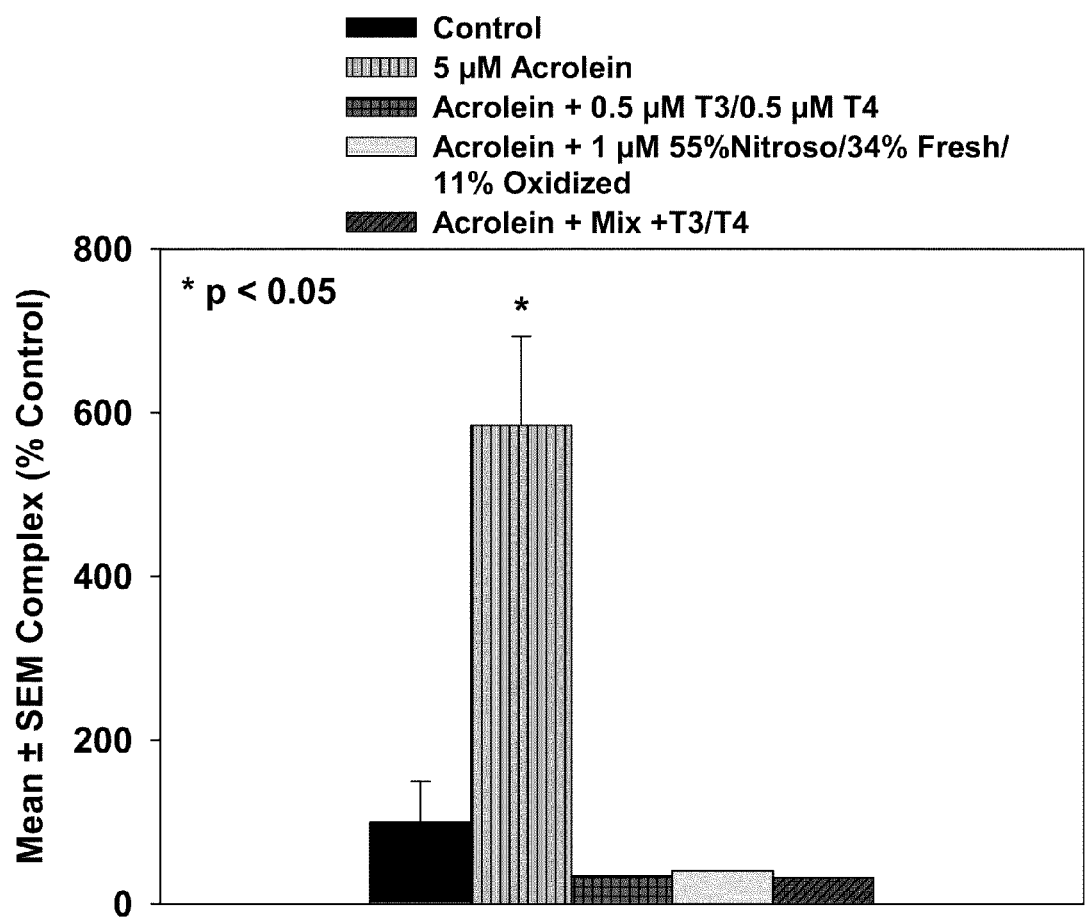
FIG. 5 summarizes the numbers of PDS/TTR-positive cells determined by immunostaining in cultures treated with acrolein, acrolein plus T3/T4, acrolein plus nifedipine mixture (nitroso nifedipine 55%, oxidized nifedipine 11% and nifedipine 34%) and acrolein plus nifedipine mix and T3/T4.

In addition, immunostaining was used to determine the PDS/TTR-positive cells and the numbers of PDS/TTR-positive cells from treated and untreated cell cultures were counted and compared. Exemplary results were summarized in FIG. 5. As can be seen from FIG. 5, the number of PDS/TTR-positive cells in acrolein alone-treat sample is about 600% of the number of PDS/TTR-positive cells in untreated control. By contrast, the numbers of PDS/TTR-positive cells in samples treated with acroline plus acrolein plus T3/T4, acrolein plus nifedipine mixture, or acrolein plus nifedipine mixture and T3/T4 were significantly reduced as compared to untreated control.

Figure 6:
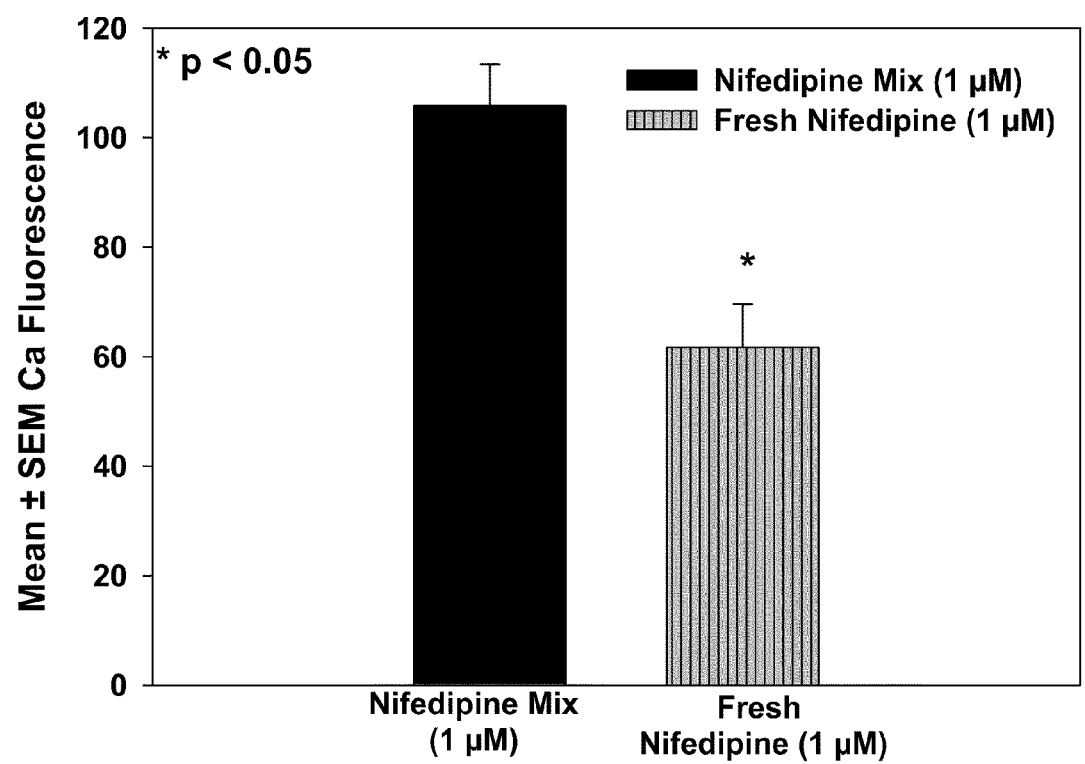
FIG. 6 illustrates that nifedipine mix does not function as a calcium channel blocker compared to fresh nifedipine as determined by confocal microscopy and a calcium fluorescent dye.

To determine if the nifedipine mix functions through blocking calcium channels, we evaluated the impact of the nifedipine mix on the calcium channels. SY5Y neuroblastoma cultures were pretreated for 16 hours with fresh nifedipine or the nifedipine mix and were then switched to calcium free medium and loaded with 5 µM Fura-2 fluorescent dye. Cultures were then rinsed with calcium free medium and exposed to calcium containing medium and fluorescence resulting from Ca binding to Fura-2 was measured using confocal microscopy and excitation at 340 nm. 50 to 100 cells were imaged per dish for 3 separate dishes. An exemplary result is shown in FIG. 6. Interestingly, as shown in FIG. 6, the nifedipine mix had minimal (~30%) activity as a calcium channel blocker compared to fresh nifedipine indicating these compounds may act through an alternative, novel mechanism.

Therefore, the experiments described in this example indicate that nifedipine analog mix and T3/T4, alone or in combination, can effectively inhibit PDS/TTR expression in epithelial cells, and this effect is likely to be independent of calcium channels. Furthermore, T3/T4 improved the effectiveness of the nifedipine analogs.

Example 3. Nifedipine Analogs Inhibit Inflammatory Cytokine Production

Figure 7:
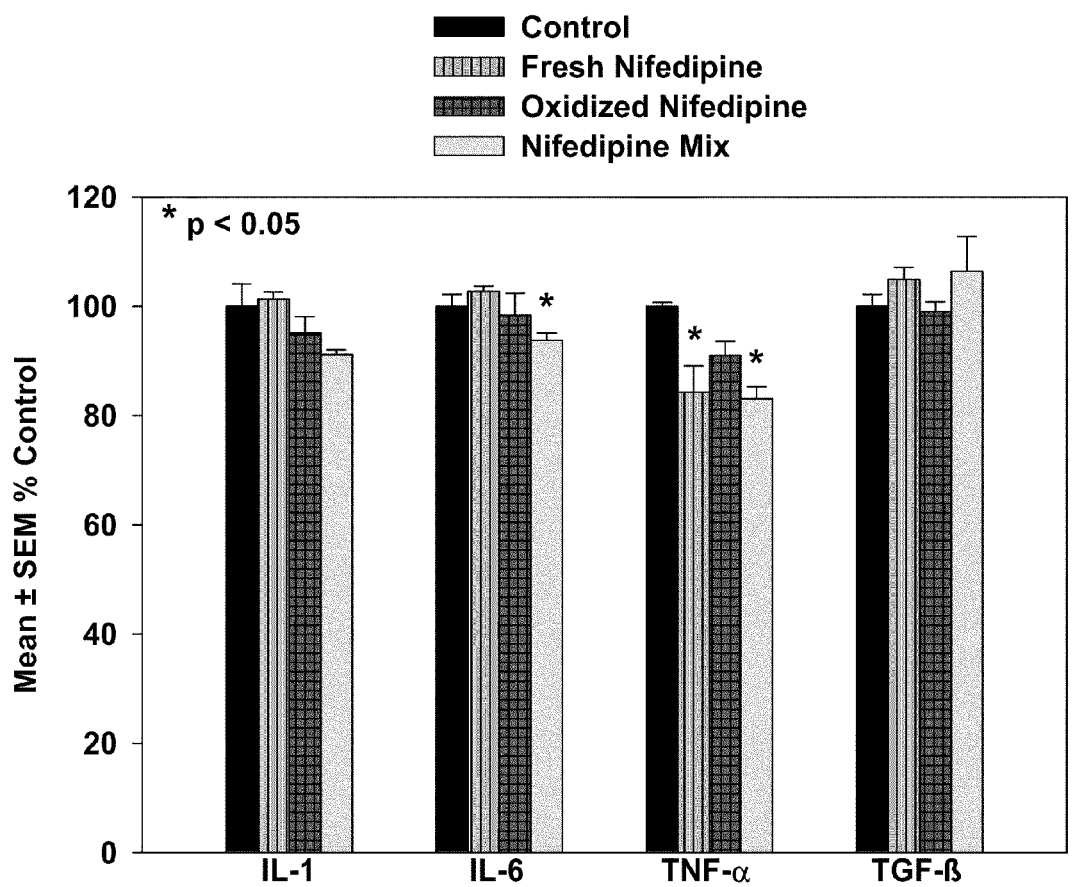
FIG. 7 illustrates exemplary results indicating that inflammatory cytokine production was inhibited by nifedipine mix.

It was reported that inflammatory response elements (cytokines) are elevated in Alzheimer's disease patients. The inventors tested the nifedipine mix and individual analogs in astrocytoma cultures. Human astrocytoma cells were plated at $2.5 \times 10^5$ cells/well in 6 well culture plates and were grown for 24 hours. Cultures were then switched to serum free Opti-MEM and treated with the nifedipine mixture and individual analogs for 24 hours. Three 6-well plates were subjected to each treatment. Following treatment, medium was collected from each well and levels of IL-1β, IL-6, TNF-α and TGF-β were measured using commercially available ELISAs. Exemplary results are shown in FIG. 7. As can be seen from FIG. 7, IL-1, IL-6 and TNF-α secreted in the medium were significantly reduced with the treatment of nifedipine mix or oxidized nifedipine, indicating these compounds have a direct positive effect on neuroinflammation.

Example 4. NFD-L1 Inhibits Inflammatory Cytokine Production

Figure 8:
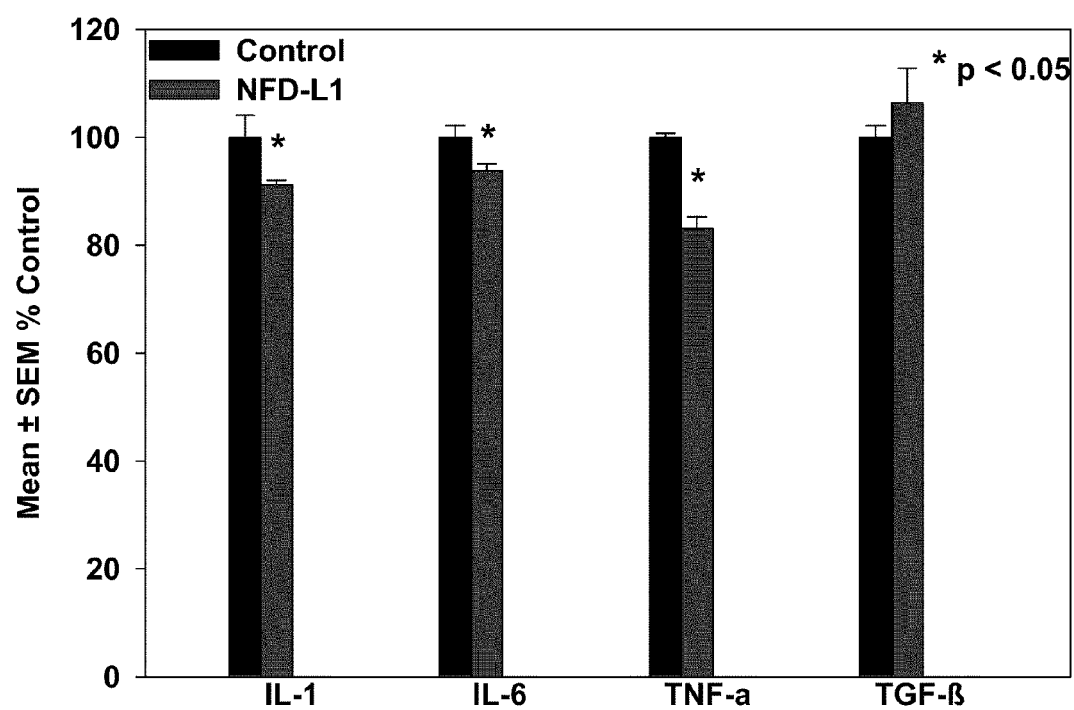
FIG. 8 illustrates exemplary results indicating that inflammatory cytokine production was inhibited by NFD-L1.

Using a similar procedure to that described in Example 3, NFD-L1 was tested in astrocytoma cultures. As can be seen from FIG. 8, IL-1, IL-6, and TNF-α secreted in the medium were significantly reduced with the treatment of NFD-L1, indicating that NFD-L1 has a direct positive effect on neuroinflammation. The results shown in this example indicate that a lactam such as NFD-L1 can effectively inhibit inflammatory condition in the central nervous system.

Example 5. Nifedipine, Nifedipine Mix and/or T3/T4 Reduce PHF-1 Levels

Figure 9:
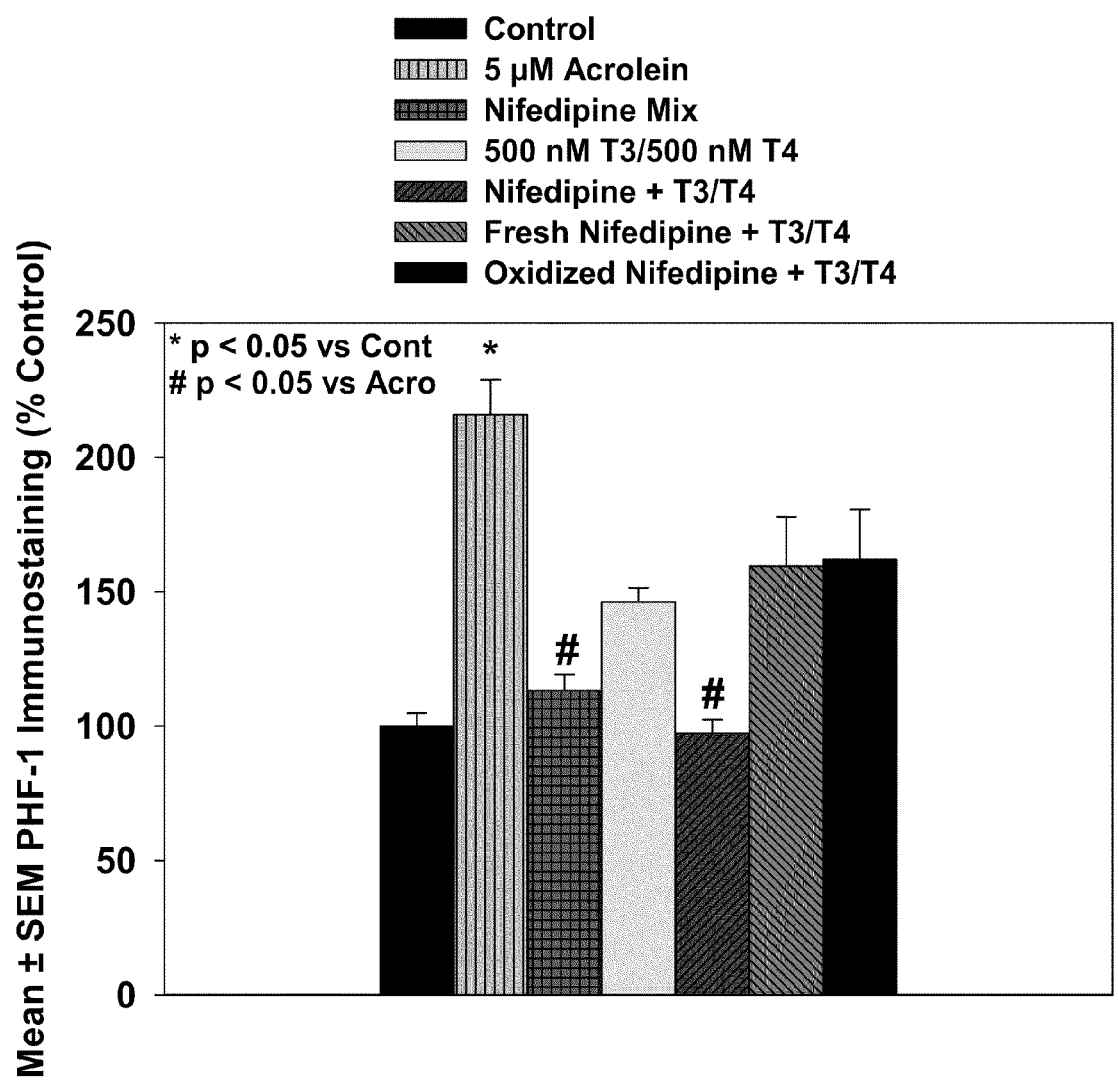
FIG. 9 illustrates quantification of PHF-1 immunostaining for SY5Y cultures treated with medium from epithelial cells treated with acrolein and combinations of nifedipine, analogs, mixtures and T3/T4.

As described in Example 1, SY5Y neuroblastoma cells exposed to medium from LAD epithelial cells that contained significantly higher levels of the PDS/TTR complex displayed significantly increased PHF-1 immunostaining as compared to those exposed to medium from untreated control cultures. In this experiment, SY5Y cells were exposed to medium from epithelial cells treated with acrolein and combinations of nifedipine, nifedipine analogs, mixtures of nifedipine analogs and T3/T4 using procedures described in Example 1. As shown in FIG. 9, nifedipine mix and nifedipine/nifedipine analogs plus T3/T4 significantly reduced PHF-1 levels.

Example 6. Inhibition of Aβ1-42 Production from H4 Neuroglioblastoma Cells

Figure 10:
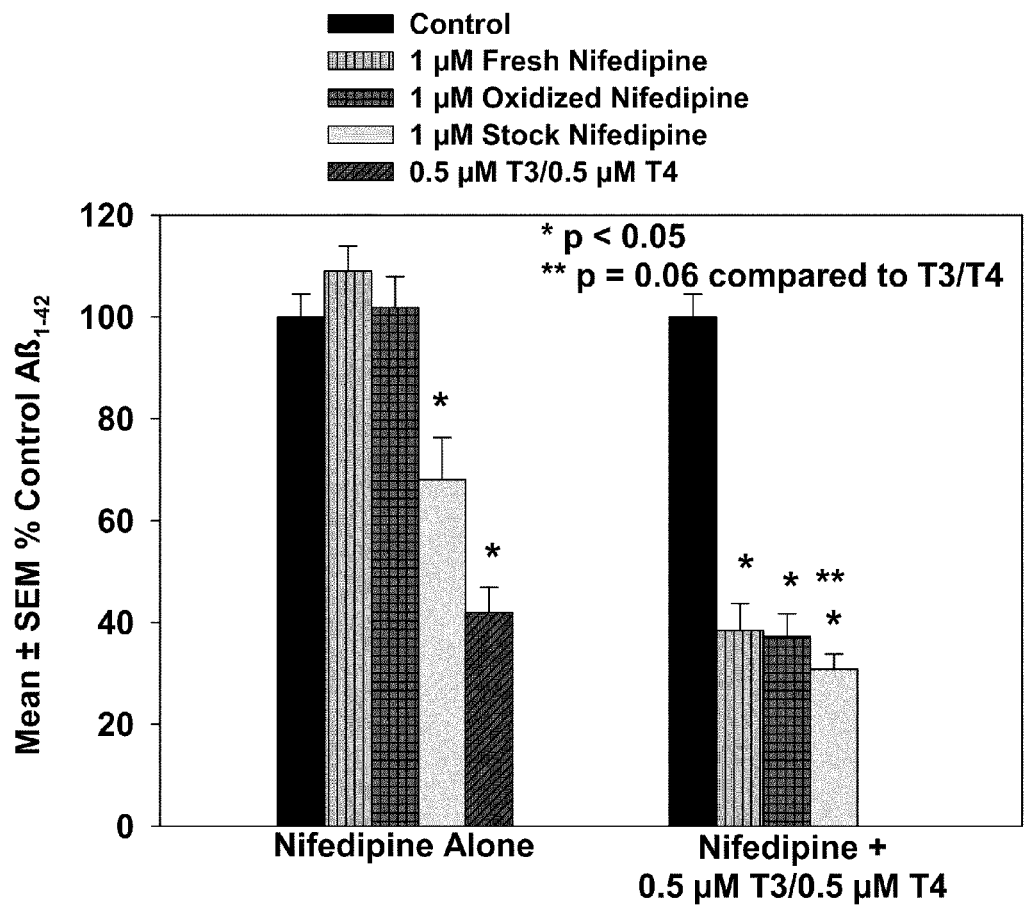
FIG. 10 illustrates exemplary results indicating that $A\beta_{1-42}$ generation is inhibited by nifedipine, oxidized nifedipine, nitroso nifedipine and T3/T4.

In this example, the inventors used H4 neuroglioblastoma cells stably transfected to overexpress amyloid precursor protein (APP) to further investigate if nifedipine, nifedipine analogs (e.g., oxidized nifedipine or nitroso-nifedipine) and/or T3/T4 can inhibit the production of Aβ1-42. H4 neuroglioblastoma cells stably transfected with a construct overexpressing amyloid precursor protein (APP) secret $A\beta_{1-42}$ into the culture medium. These H4 cells were treated with 1 µM fresh nifedipine, 1 µM oxidized nifedipine, 1 µM nitroso-nifedipine, or 0.5 µM T3/0.5 µM T4 for 16 hours. The Aβ levels in the culture medium were measured using ELISAs (Invitrogen). As shown in FIG. 10, treatment of fresh nifedipine, oxidized nifedipine, nitroso-nifedipine, or T3/T4 lead to significantly decreased production of Aβ1-42.

Figure 11:
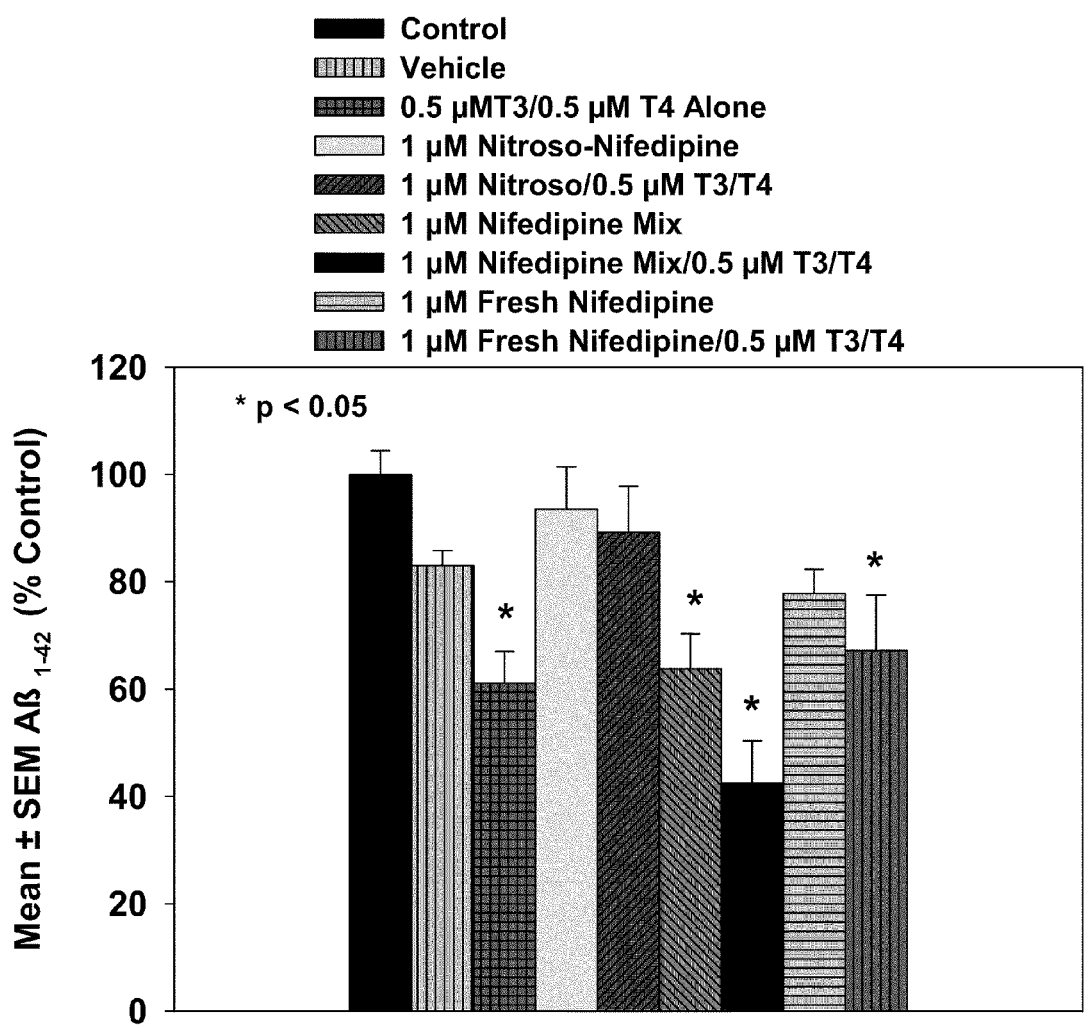
FIG. 11 illustrates exemplary results indicating effect of nifedipine, nifedipine analogs and nifedipine mix, with and without T3/T4 on $A\beta_{1-42}$ production from H4 cells.

Furthermore, the effect of nifedipine, nifedipine analogs and nifedipine mix on Aβ1-42 production from H4 cells were further tested with and without T3/T4. Exemplary results are summarized in FIG. 11. As can be seen, T3/T4 improves the inhibitory effect of nifedipine, nifedipine analogs and nifedipine mix on Aβ1-42 production.

Figure 12:
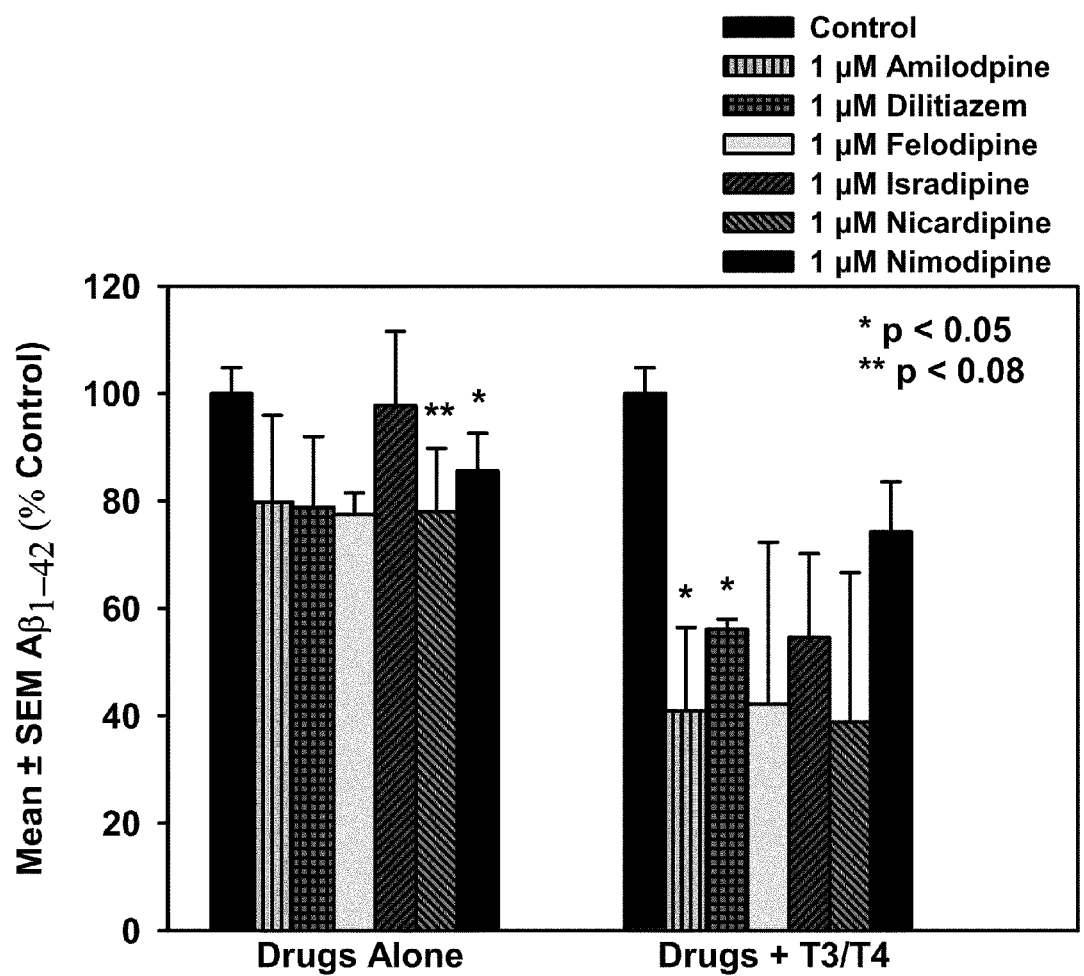
FIG. 12 illustrates exemplary results indicating effects of known calcium channel blockers such as Amilodpine, Dilitiazem, Felodipine, Isradipine, Nicardipine, and Nimodipine on $A\beta$ 1-42 generation in H4 neuroglioma cultures.

We then tested if other calcium channel blockers can inhibit Aβ 1-42 generation in H4 neuroglioma cultures. Known calcium channel blockers such as Amilodpine, Dilitiazem, Felodipine, Isradipine, Nicardipine, and Nimodipine were used in this experiment. Specifically, H4 cells were treated with 1 µM each drug, with and without T3/T4, in opti-MEM (Serum free) for 16 hours and Aβ1-42 secreted into medium was measured using Invitrogen ELISAs. Exemplary results are shown in FIG. 12. As shown in FIG. 12, Nicardipine, showed a trend (p<0.10) toward a significant decrease in Aβ secretion and Nimodipine led to a significant (p<0.05) decrease in Aβ formation. The other drugs did not significantly alter levels of Aβ formation. Combining the alternate calcium channel blockers with T3/T4 showed a significant decrease of Aβ formation when T3/T4 were combined with Amlodipine and Dilitiazem. Combinations of T3/T4 with the other drugs did not provide any significant decrease in Aβ formation.

Example 7. Inhibition of Aβ1-42 Production from H4 Neuroglioblastoma Cells by NFD-L1

Figure 13:
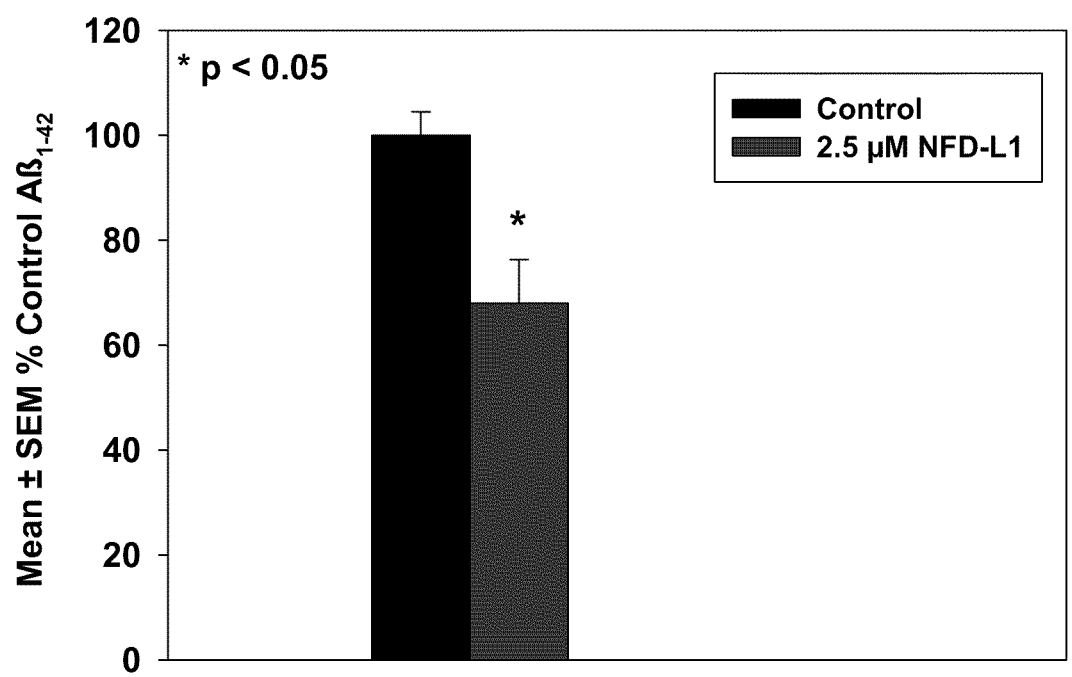
FIG. 13 illustrates exemplary results indicating effects of NFD-L1 on $A\beta$ 1-42 generation in H4 neuroglioma cultures.

Using a procedure similar to that described in Example 6, NFD-L1 was tested for inhibition of Aβ 1-42 generation in H4 neuroglioma cultures. As shown in FIG. 13, Aβ 1-42 generation is inhibited by NFD-L1. The results shown in this example indicate that a lactam such as NFD-L1 can effectively inhibit Aβ1-42 production.

Example 8. Inhibition of Beta Secretase (BACE) and Gamma Secretase Activity

This surprising finding that nifedipine, nifedipine analogs and nifedipine mix can effectively inhibit $A\beta_{1-42}$ peptide generation prompted further investigation into possible mechanism of $A\beta_{1-42}$ peptide reduction. It was contemplated that $A\beta_{1-42}$ production depends on the activity of beta secretase (BACE), an enzyme that cleaves the amyloid precursor protein at the beta secretase cleavage site, and the gamma secretase complex composed of presenilin-1 (PS-1), nicastrin, APH-1 and PEN-2 that cleaves at the gamma secretase cleavage site. The inventors tested whether the inhibition of $A\beta_{1-42}$ production in our culture model system was due to inhibition of BACE and/or gamma secretase activities.

Figure 14:
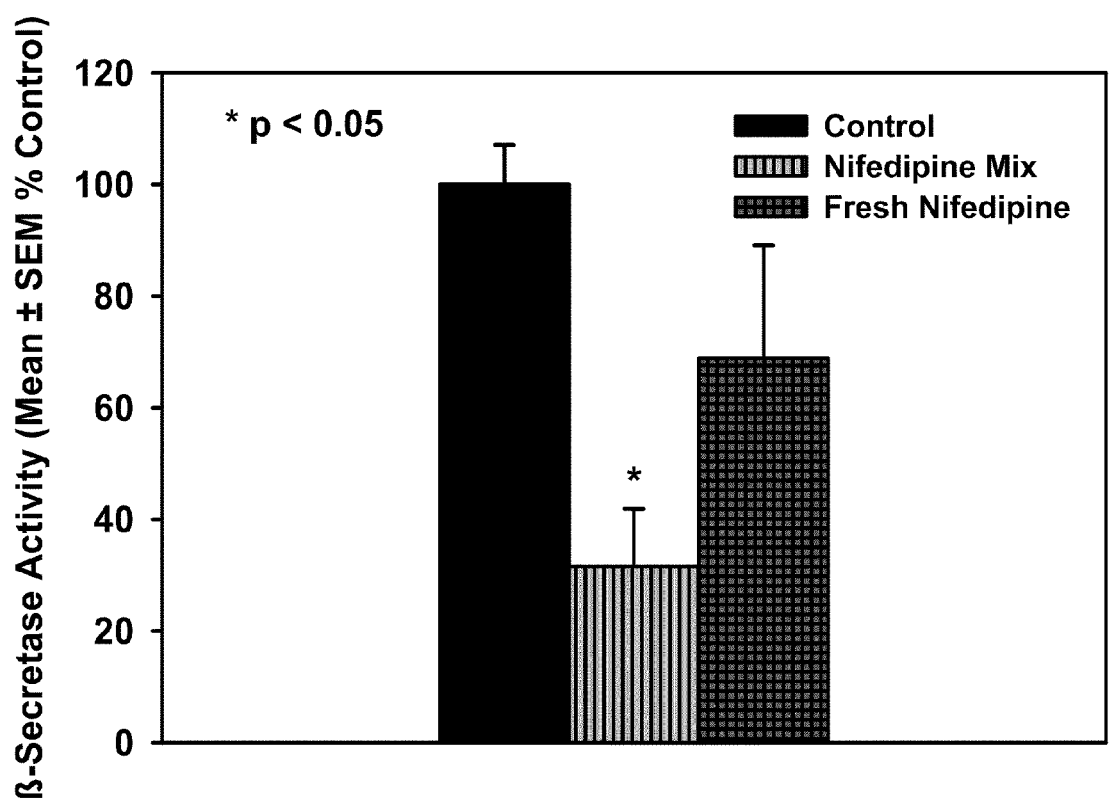
FIG. 14 illustrates exemplary results indicating that nitroso-nifedipine significantly inhibits BACE activity.

BACE activity was measured using a fluorescent substrate and purified recombinant BACE as part of a commercial kit from Invitrogen. As shown in FIG. 14, nifedipine alone or in combination with thyroxine slightly inhibited BACE activity; however, nitroso-nifedipine alone and in combination with thyroxine led to significant inhibition of BACE activity (FIG. 14).

Figure 16:
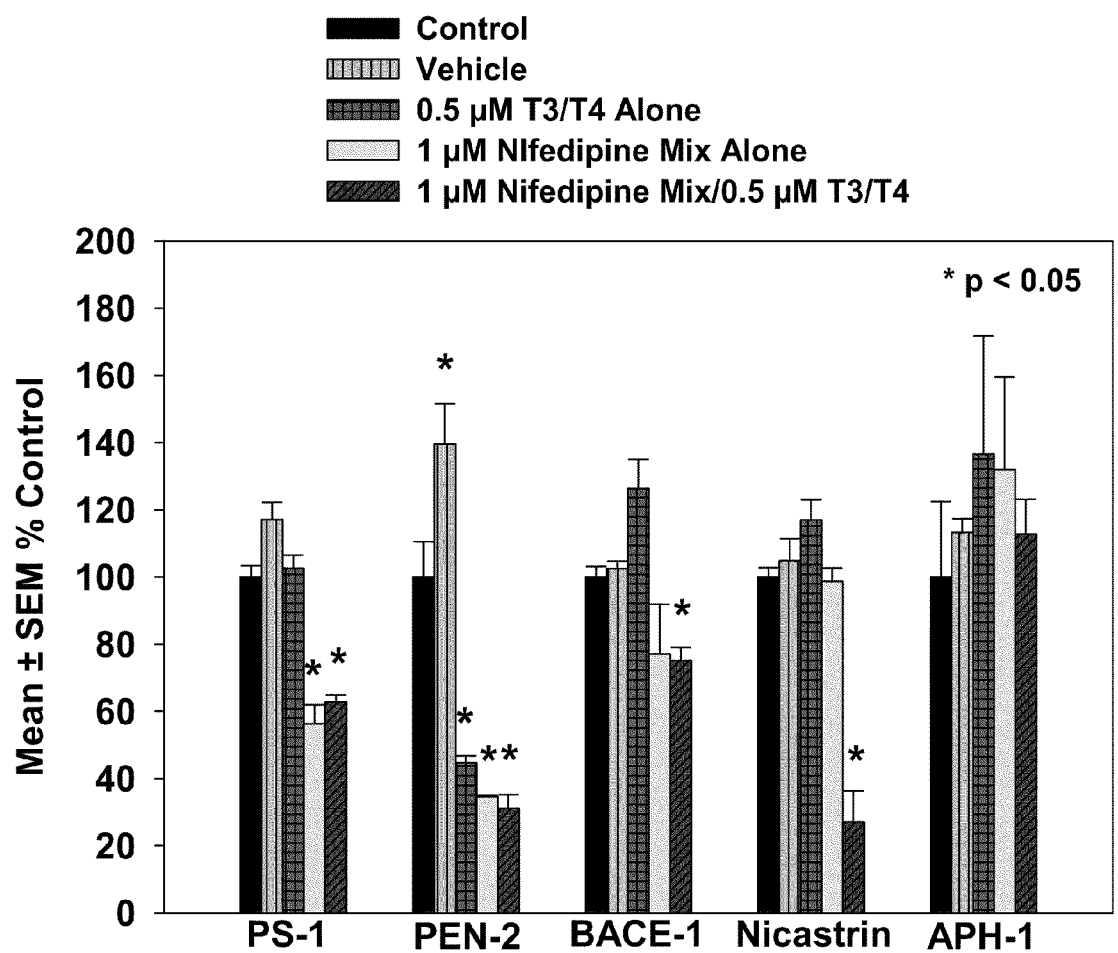
FIG. 16 illustrates exemplary results indicating the effect of nifedipine mix on PS-1, PEN-2, BACE-1 and Nicastrin, with and without T3/T4.

Examination of protein levels of BACE and individual components of the gamma secretase complex in H4 cultures treated with the nifedipine mix alone or in combination with T3/T4 revealed that the nifedipine mix alone significantly reduced levels of PS-1 and PEN-2. Levels of BACE-1 were decreased but not significantly. However, the nifedipine mix plus T3/T4 significantly reduced PS-1, PEN-2, BACE-1 and Nicastrin. APH-1 was not affected by any treatment. Exemplary results were shown in FIG. 16. Protein levels were determined in individual cells (50-100 cells/dish; 3 dishes/experiment) using immunohistochemistry and confocal microscopy and were verified in total cell homogenate using Western blot analysis. Antibodies specific to each protein were purchased from commercial vendors.

Experiments described in this example demonstrated that nifedipine mixtures, their oxidized and nitroso derivatives, and/or T3/T4 directly act on the enzymes responsible for Aβ production.

Example 9. Inhibition of Beta Secretase (BACE) by NFD-L1

Figure 15:
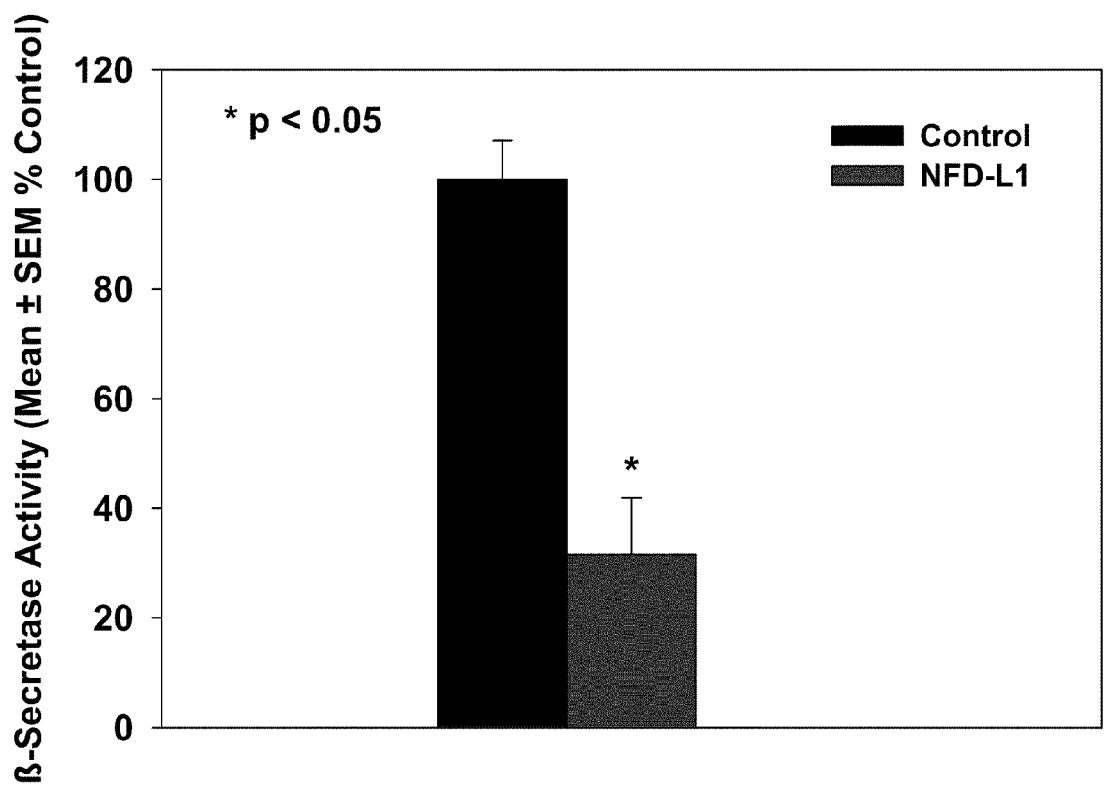
FIG. 15 illustrates exemplary results indicating that NFD-L1 significantly inhibits BACE activity.

Using a similar procedure as described in Example 8, NFD-L1 was tested for inhibition of BACE activity. As shown in FIG. 15, NFD-L1 inhibits BACE. This example indicates that a lactam such as NFD-L1 can effectively inhibit beta secretase (BACE) activity.

Example 10. Inhibition of Aβ1-40 Production In Vivo

Based on the in vitro data described above, the inventors initiated an acute exposure study in 3 month old C57-Black-6 (C57BL/6) mice. In this study, six groups of six C57BL/6 mice were subjected to intraperitoneal (IP) injections of vehicle (2% DMSO/98% polyethylene glycol-3000 (PEG-3000), 25 mg/kg nifedipine or nifedipine mix, T3/T4 (10 mg/kg T3 and 10 mg/kg T4), nifedipine mix plus T3/T4 and nifedipine plus T3/T4 on three consecutive days. Animals were euthanatized 1 hour after the third injection. The brains and terminal serum were removed and immediately frozen in liquid nitrogen and stored at −80° C. until used for analysis.

Figure 17:
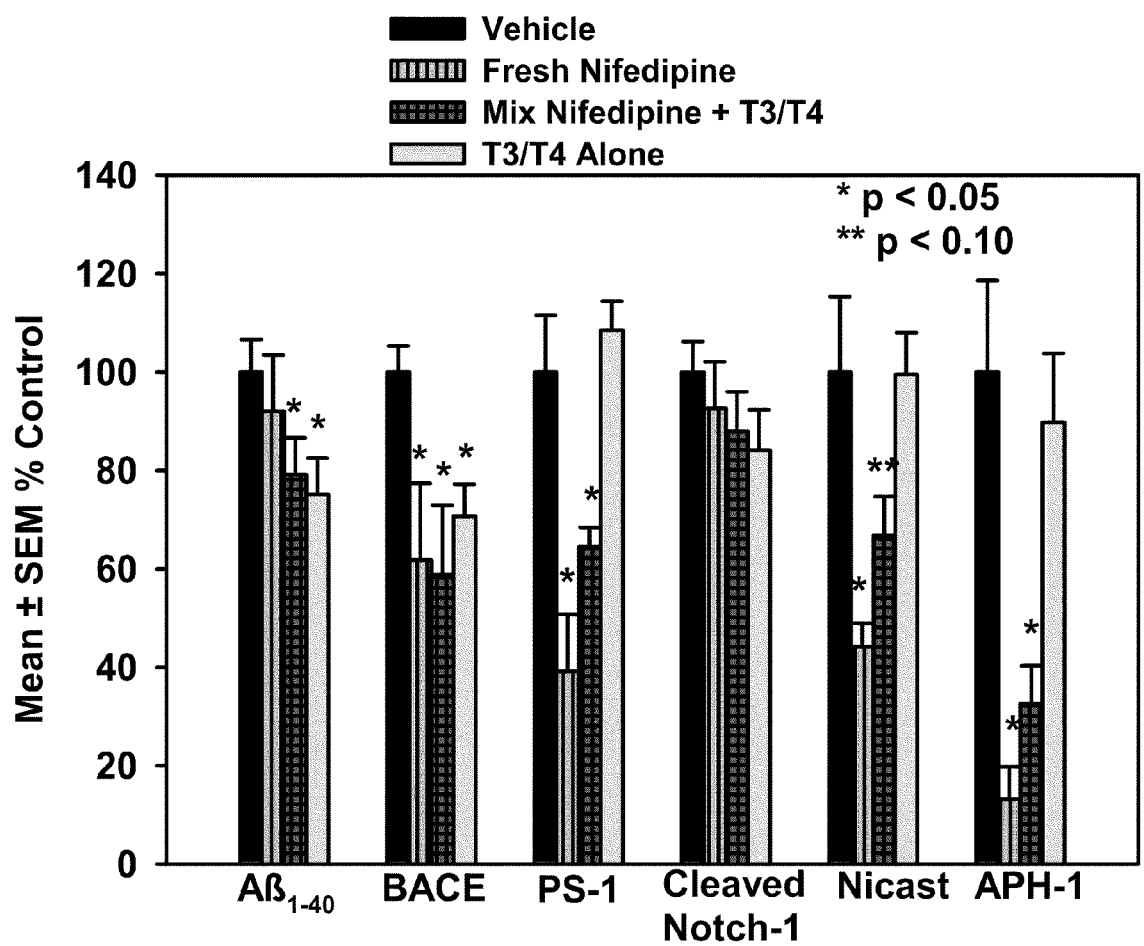
FIG. 17 illustrates exemplary results indicating the effect of nifedipine, nifedipine mix and/or T3/T4 on $A\beta$1-40 generation and certain $A\beta$1-40 processing enzymes in a mouse model.

One hemisphere of brains was homogenized for Aβ1-40 measurements (Invitrogen ELISA) and the other homogenized for protein levels. In addition, levels of PS-1, BACE, cleaved Notch, an essential substrate for PS-1, Nicast, APH-1 were measured using Western blot analysis. As shown in FIG. 17, mice treated with both T3/T4 and nifedipine mix plus T3/T4 showed a modest (25%) but significant decrease in $A\beta_{1-40}$ levels compared to animals treated with vehicle. Levels of PS-1, Nicast, and APH-1 were significantly decreased in mice treated with nifedipine, nifedipine mix plus T3/T4. BACE protein levels were significantly decreased in mice treated with nifedipine, nifedipine plus T3/T4 and T3/T4 alone. In contrast, there were no significant differences in levels of cleaved Notch with any treatment (FIG. 17).

Additionally the brains were extracted and analyzed by GC/MS for levels of nifedipine and its analogs. Oxidized nifedipine was found in all samples analyzed indicating that components of the mixture were passing the blood-brain barrier and thus available for neuronal protection. This experiments has shown that these derivatives possess the brain permeability desired for treatment of Alzheimer's disease.

Experiments described in this example demonstrated that nifedipine mixtures, their oxidized and nitroso derivatives, and/or T3/T4 reduce endogenous levels of Aβ 1-40 peptide in vivo.

Example 11. Nitroso-Nifedipine Inhibits Production of Aβ1-40 In Vivo

Figure 18:
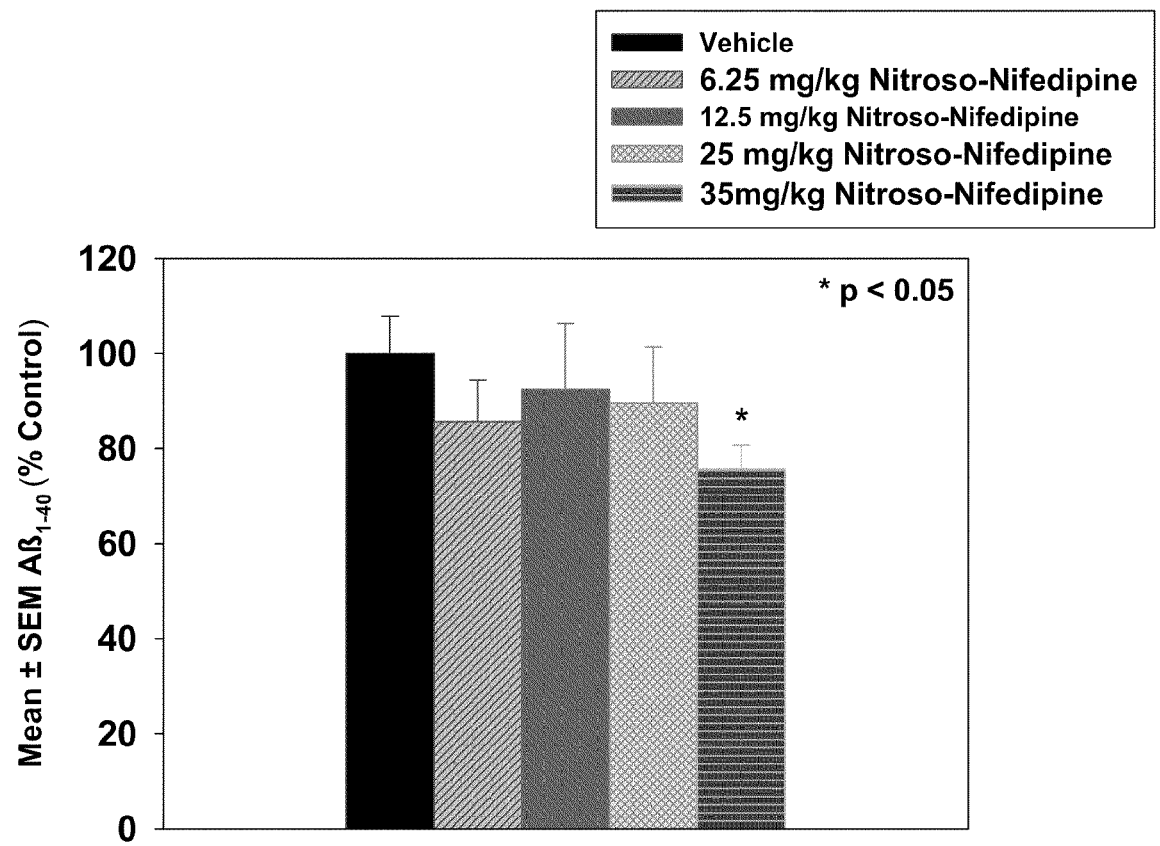
FIG. 18 illustrates exemplary results indicating that treatment with nitroso-nifedipine leads to a decrease in levels of $A\beta$1-40 in a mouse model.

Additional experiments were conducted to show that nitroso-nifedipine can effectively inhibit production of Aβ1-40 in vivo. Specifically, C57/B16 mice (6 per group) were given IP injections of increasing concentrations of nitroso-nifedipine in 2% DMSO/98% PEG-300 for 3 days. The animals were sacrificed 15 minutes following the final injection. Brains were quickly removed, split into hemispheres, and snap frozen in liquid nitrogen. Brains were shipped on dry ice and maintained at −80° C. until used for analysis. One hemisphere of each brain was homogenized in diethylamine (200 mg wet weight/mL) containing complete protease inhibitors using a Dounce homogenizer. Homogenate was centrifuged at 16,000×g for 30 minutes and 50 µL soluble protein subjected to Aβ1-40 quantification using a Covance ELISA per manufacturer's instructions. Results are expressed as % vehicle treated animals. Results of the analyses showed acute treatment with 35 mg/kg nitroso-nifedipine led to a significant decrease in levels of Aβ1-40 (FIG. 18).

Thus, this example demonstrates that nitroso-nifedipine effectively inhibits production of Aβ1-40 in vivo.

Example 12. Inhibition of Orphan G-Coupled Receptor Protein 3 (GPCR-3) In Vitro and In Vivo This example was conducted to test if nifedipine, nifedipine mixtures, and/or T3/T4 can inhibit the orphan G-coupled receptor protein 3 (GPCR-3), an enzyme which is suggested to play a role in maintaining stability of the gamma secretase complex (which, as discussed above, is important for cleavage of APP to form Aβ).

Figure 19:
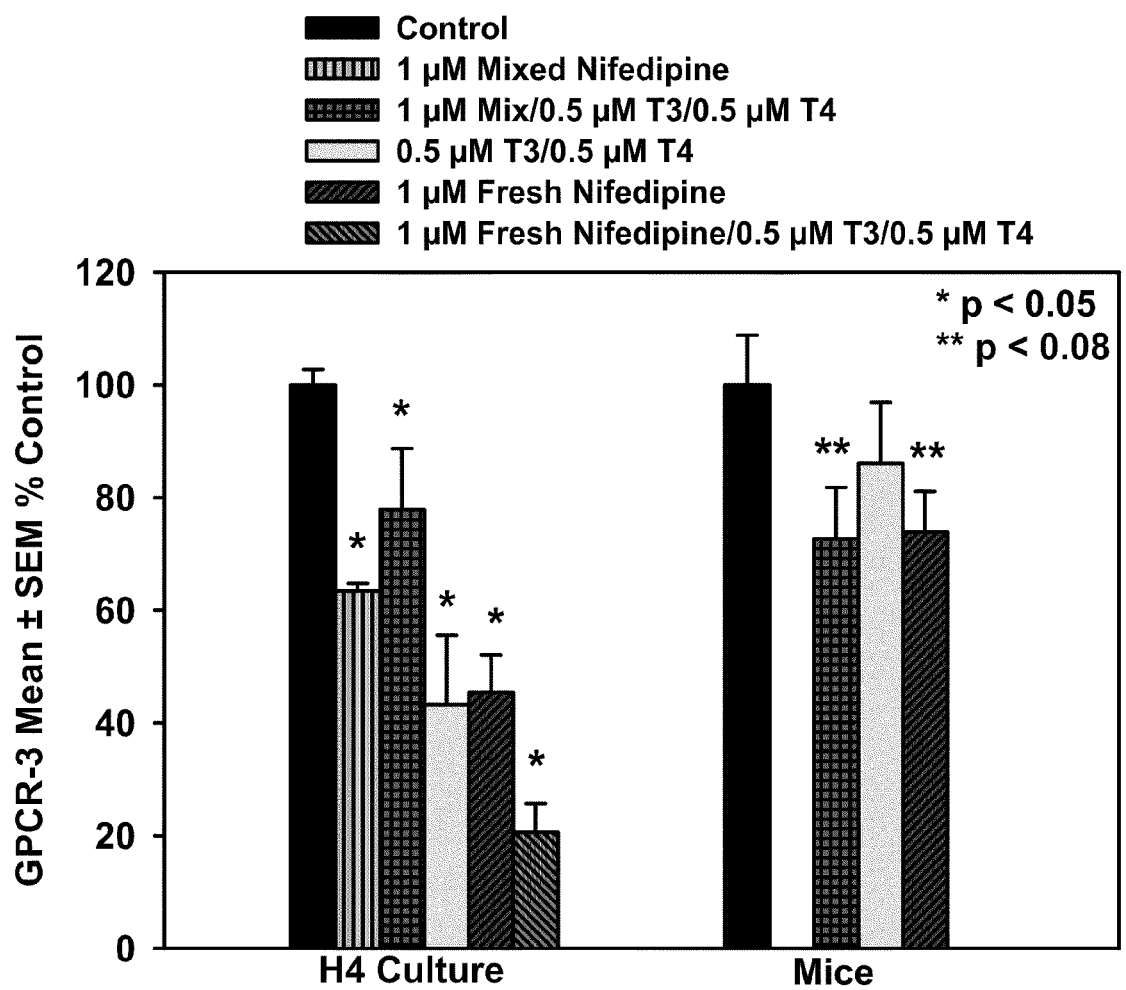
FIG. 19 illustrates exemplary results indicating that nifedipine, nifedipine mix and/or T3/T4 reduced GPCR-3 levels in H4 cultures or in mice treated acutely with drugs. The GPCR-3 levels were determined using Western blot analysis.

H4 neuroglioblastoma cells were treated with 1 µM mixed nifedipine, 1 µM mixed nifedipine plus 0.5 µM T3/0.5 µM T4, 0.5 µM T3/0.5 µM T4, 1 µM fresh nifedipine, 1 µM fresh nifedipine plus 0.5 µM T3/0.5 µM T4 for 16 hours. Levels of GPCR-3 were measured using Western blot analysis using a GPCR-3 specific antibody. As shown in FIG. 19, nifedipine mixtures, fresh nifedipine, and/or T3/T4 significantly reduced GPCR-3 expression levels in H4 cells.

In addition, GPCR-3 levels were determined in the C57BL/6 mice described above in Example 10 using Western blot analysis. Exemplary results are also shown in FIG. 19. Nifedipine mixtures and T3/T4, fresh nifedipine, and T3/T4 also reduced GPCR-3 expression levels in mice.

Therefore, this example demonstrated that nifedipine mixtures, their oxidized and nitroso derivatives, and/or T3/T4 reduce GPCR-3 levels in vitro and in vivo.

Figure 20:
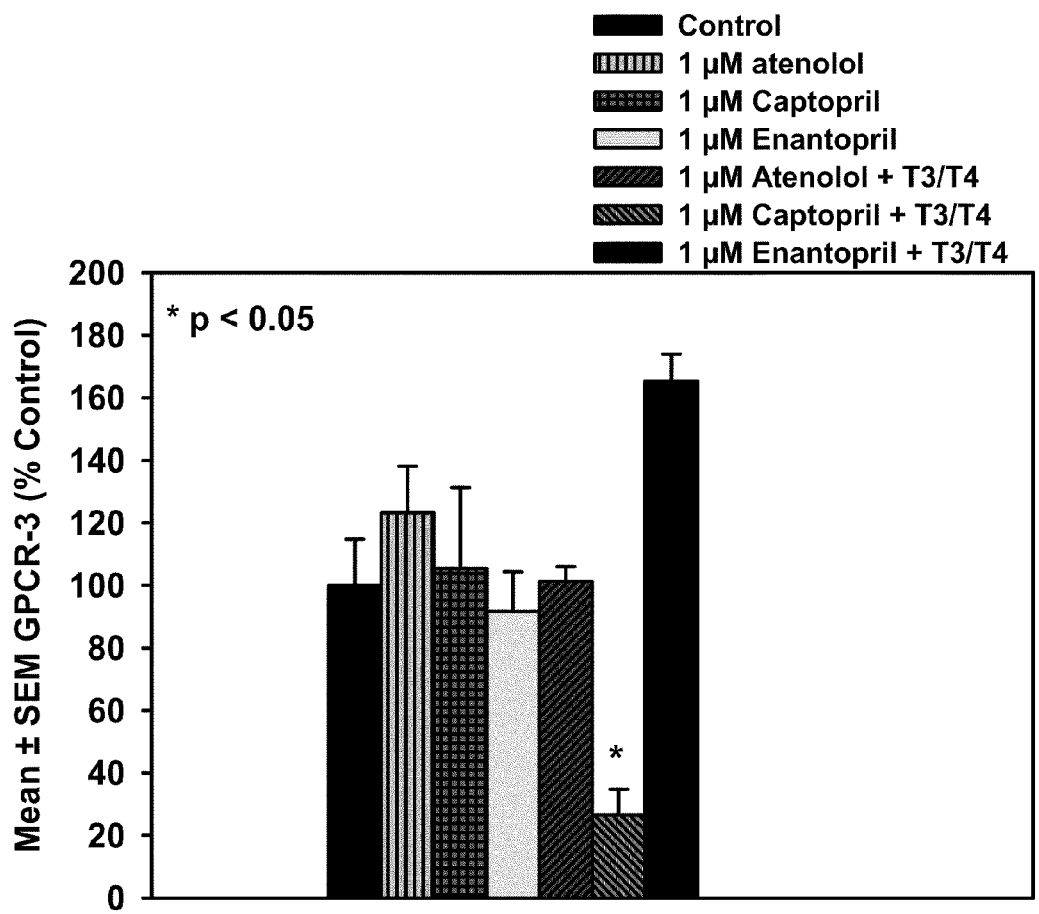
FIG. 20 illustrates exemplary results indicating the effect of other classes of blood pressure drugs on the levels of GPCR-3 in H4 cultures with and without T3/T4.

To determine if the reduction of GPCR-3 levels by nifedipine mixtures, their oxidized and nitroso derivatives, and/or T3/T4 is through a pathway involved in blood pressure regulation, we tested known blood pressure drugs such as atenolol, captopril, and enantopirl on H4 cells. Specifically, H4 cells were treated with 1 µM each drug, with and without T3/T4, in Opti-MEM (Serum free) medium for 16 hours and levels of GPCR-3 were measured using confocal microscopy and a specific anti-GPCR-3 antibody. Exemplary results are shown in FIG. 20. As shown in FIG. 20, only captopril+T3/T4 led to a significant change (decrease) in levels of GPCR-3. This experiment indicates that the reduction of GPCR-3 by nifedipine mixtures, their oxidized and nitroso derivatives, and/or T3/T4 is independent of blood pressure pathways.

Figure 21:
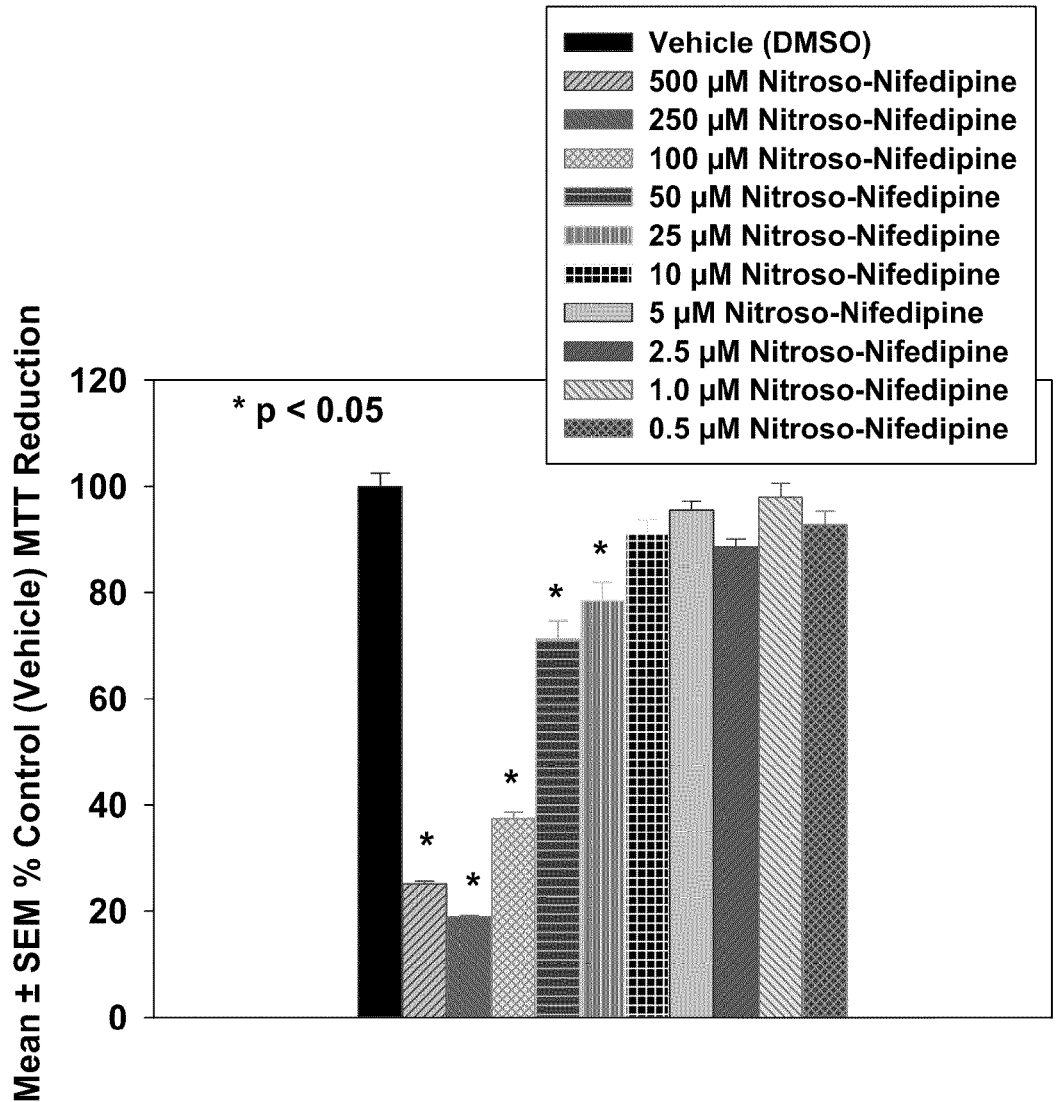
FIG. 21 illustrates exemplary results showing survival of H4 cells after treatment with increasing concentrations of nitroso-nifedipine.

Example 13. Effects of Nitroso-Nifedipine on Levels of Enzymes Involved in Aβ Processing This experiment was conducted to determine effects of nitroso-nifedipine on levels of enzymes involved in Aβ processing. Suitable concentration of nitroso-nifedipine was first determined based on the survival rate of H4 cells treated with increasing concentrations of nitroso-nifedipine. Specifically, H4 neuroglioma cultures were plated at a density of $2.5\times10^5$ cells/well and allowed to attach overnight. Cultures were switched to Opti-MEM and treated for 16 hours with increasing concentrations of nitroso-nifedipine. Following treatment, MTT was added at a final concentration of 0.5 mg/mL and cultures incubated for 30 minutes. Following MTT treatment, medium was removed and the formazan crystals generated by mitochondrial conversion of MTT were dissolved in DMSO and absorbance was measured at 650 nm. Data are reported as mean±SEM % control MTT reduction (FIG. 21). Results of the studies suggest that H4 cultures are more resistant to nitroso-nifedipine compared to nifedipine. Based on survival data, 2.5 µM nitroso-nifedipine was chosen for use in additional studies.

Figure 22:
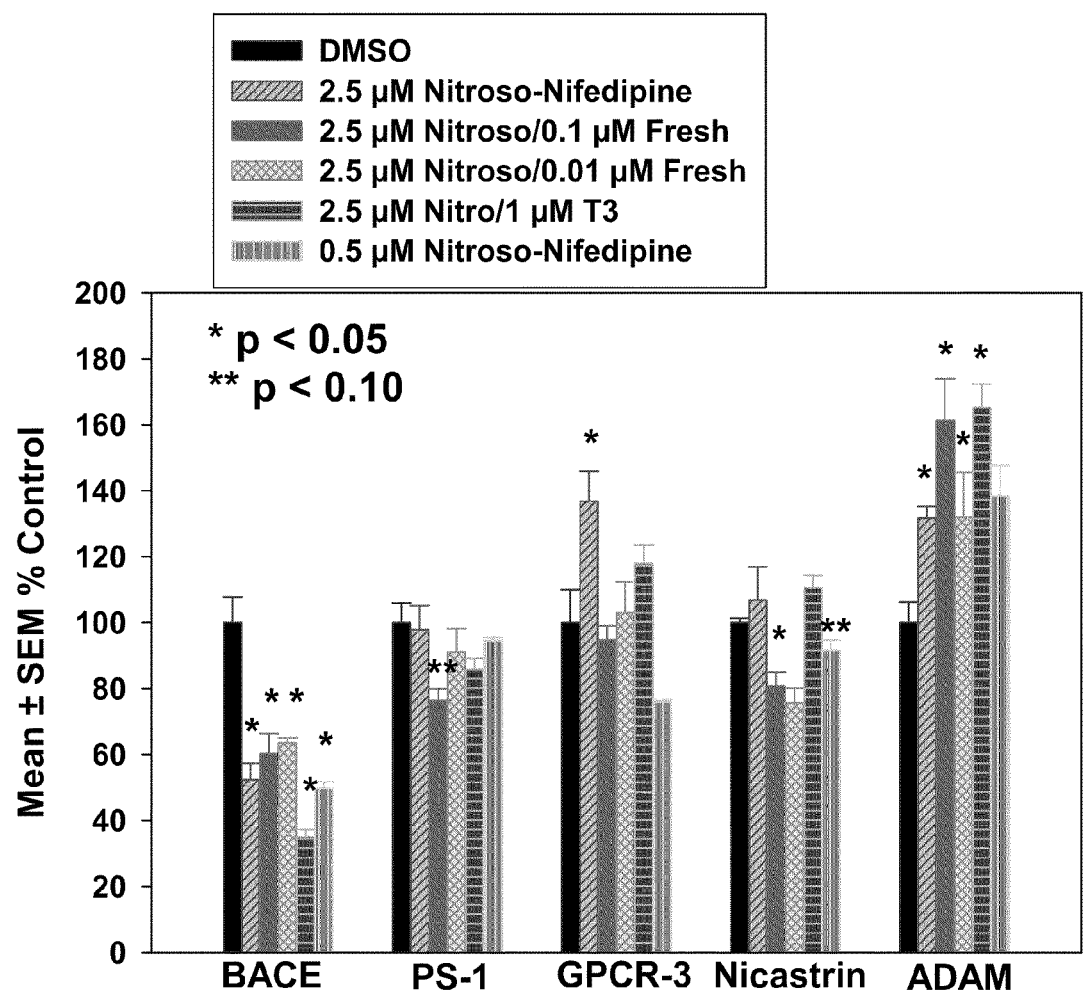
FIG. 22 summarizes exemplary effects of nitroso-nifedipine on levels of enzymes involved in $A\beta$ processing.

To determine the effects of nitroso-nifedipine on levels of enzymes involved in Aβ processing, H4 neuroglioma cultures that overexpress APP were plated at a density of $2.5\times10^5$ cells/dish and allowed to attach overnight. Cultures were switched to Opti-MEM and treated with 2.5 µM or 0.5 µM nitroso-nifedipine alone or 2.5 µM nitroso-nifedipine+ nifedipine (0.1 and 0.01 µM) or 1 µM T3/T4. Following treatment, cultures were rinsed three times in PBS and fixed in 70% methanol/30% acetone for 30 minutes at −20° C. Cultures were then subjected to immunohistochemistry for BACE, PS-1, GPCR-3, nicastrin, and ADAM (the enzyme responsible for alpha secretase cleavage). 30 to 50 cells were imaged in 4-5 fields/dish (3 dishes each treatment) (FIG. 22). Similar to results observed for nifedipine, nitroso-nifedipine treatment led to a significant decrease in BACE protein. In contrast to nifedipine, nitroso-nifedipine did not significantly alter PS-1 or nicastrin levels. Also in contrast to nifedipine, nitroso-nifedipine led to a significant increase in GPCR-3. Nitroso-nifedipine also led to a significant increase in levels of ADAM-10 which is responsible for cleavage of Aβ at the alpha secretase site. Alpha secretase cleavage leads to decreased Aβ1-42.

Example 14. Effects of NFD-L1 on Levels of Enzymes Involved in Aβ Processing

Figure 23:
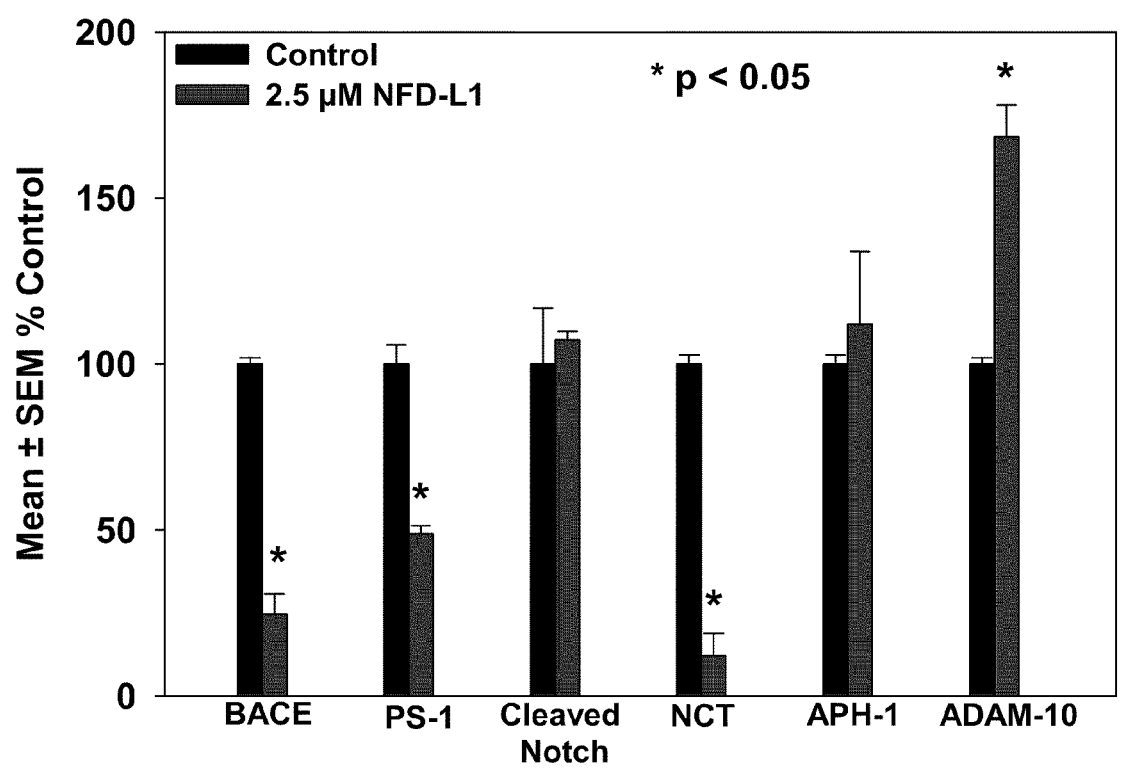
FIG. 23 summarizes exemplary effects of NFD-L1 on levels of enzymes involved in $A\beta$ processing.

Using a similar procedure as described in Example 13, H4 neuroglioma cultures were treated with NFD-L1 to determine the effects of NFD-L1 on levels of enzymes involved in Aβ processing. As shown in FIG. 23, similar to nitroso-nifedipine, NFD-L1 led to a significant decrease in BACE protein and a significant increase in ADAM-10. NFD-L1 also led to a significant decrease in PS-1 and NCT. This example demonstrated that treatment with lactam such as NFD-L1 has significant effect on levels of enzymes involved in Aβ processing.

Figure 24:
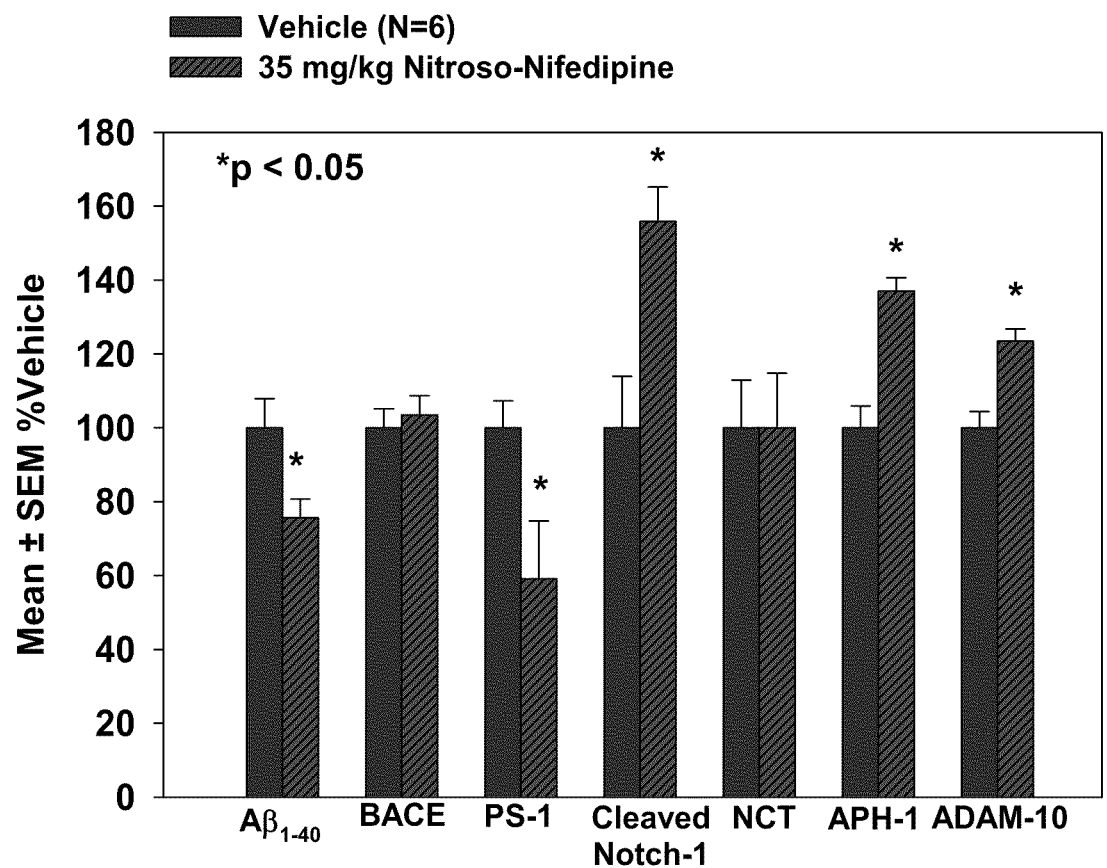
FIG. 24 summarizes exemplary effects of nitroso-nifedipine on levels of enzymes involved in $A\beta$ processing in a mouse model.

Example 15. Effects of Nitroso-Nifedipine on Levels of Enzymes Involved in Aβ Processing in Vivo To determine the effects of nitroso-nifedipine on levels of enzymes involved in Aβ processing in vivo, levels of Aβ were quantified by ELISA and levels of proteins involved in Aβ processing were quantified by Western blot analysis for mice treated with vehicle or 35 mg/kg nitroso-nifedipine (FIG. 24). IP injections for 3 days led to a significant decrease in Aβ1-40 and a significant decrease in presenilin-1. The data also show that nitroso-nifedipine mediated inhibition of PS-1 did not decrease levels of cleaved Notch-1 but instead led to a significant increase in levels of cleaved Notch-1. In addition, treatment with nitroso-nifedipine led to a significant increase in levels of ADAM-10, which functions as an alpha secretase. It is contemplated that increased ADAM-10 levels lead to increased cleavage at the alpha secretase position of APP, minimizing generation of Aβ.

Figure 25:
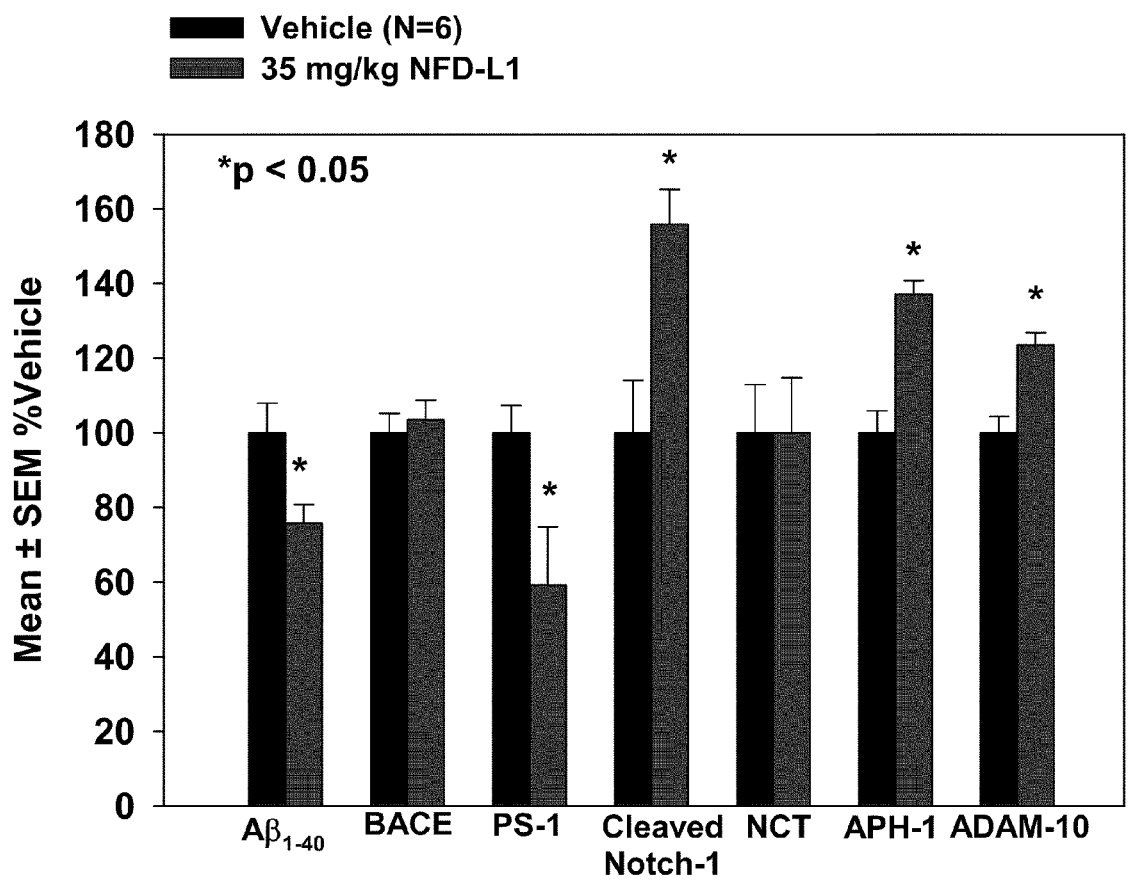
FIG. 25 summarizes exemplary effects of NFD-L1 on levels of enzymes involved in $A\beta$ processing in a mouse model.

Example 16. Effects of NFD-L1 on Levels of Enzymes Involved in Aβ Processing In Vivo The effects of NFD-L1 on levels of enzymes involved in Aβ processing in vivo were determined using a similar procedure to that described in Example 15. As shown in FIG. 25, similar to nitroso-nifedipine, IP injections of NFD-L1 led to a significant decrease in Aβ1-40 and a significant decrease in presenilin-1. The data also show that NFD-L1 mediated inhibition of PS-1 led to a significant increase in levels of cleaved Notch-1. In addition, treatment with NFD-L1 led to a significant increase in levels of ADAM-10. Thus, this example demonstrated that treatment with lactam such as NFD-L1 has significant effect on levels of enzymes involved in Aβ processing in vivo.

Example 17. Inhibition of Tau Phosphorylation

In this example, we tested if nifedipine, nifedipine mixtures, their oxidized and nitroso derivatives, and/or T3/T4 can reduce phosphorylated Tau protein. Phosphorylated tau protein can result in the self-assembly of tangles of paired helical filaments and straight filaments, which are involved in the pathogenesis of Alzheimer's disease.

Although there are multiple kinases involved in Tau phosphorylation, glycogen synthase kinase-3β (GSK-3β) has received considerable attention as a major contributor to Tau hyperphosphorylation in AD. GSK-3β is present in ~95% paired helical filaments identified using specific-phospho-Tau antibodies. GSK-3β, a constitutively active kinase is inactivated by phosphorylation of Ser 9 by protein kinase B (Akt). Akt, a serine/threonine kinase is regulated by phosphatidylinositol kinase (PI3K) mediated signaling and is activated by phosphorylation of a regulatory threonine residue (Thr-308) by phosphatidylinositol dependent kinase 1 (PDK1) and by phosphorylation of Ser 473 by PDKα/TORC2 kinase. In addition, activation of the Akt/GSK-3β pathway may be mediated by GCPRs coupled to $G_{\alpha 12/13}$ heterotrimeric G proteins. Activation of $G\alpha_{12}$ has been shown to stimulate RhoA and its effector Rho kinase (ROCK). ROCK phosphorylated at ser160 further transactivates a receptor tyrosine kinase (RTK) that activates the PI3K signaling pathway leading to phosphorylation/activation of Akt/GSK-3β (reviewed by New et al, "G protein-coupled receptor-induced Akt activity in cellular proliferation and apoptosis," *FEBS J*, 2007; 274:6025-36.). Phosphoryalted Akt increases phosphorylation and inactivation of GSK-3β therefore reducing Tau phosphorylation.

Figure 26:
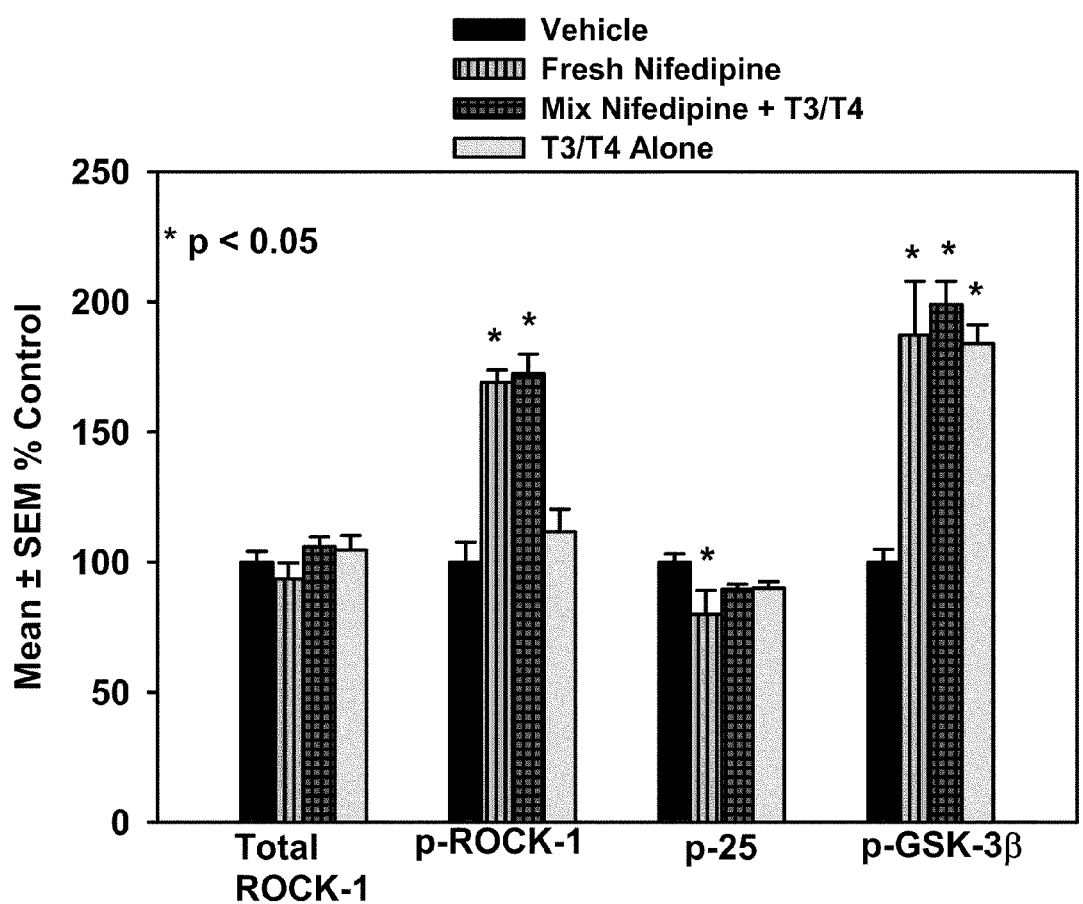
FIG. 26 illustrates exemplary results indicating the effect of nifedipine, nifedipine mix and/or T3/T4 on the levels of enzymes involved in Tau phosphorylation measured in the mouse brains treated with corresponding compounds.

We examined levels and the phosphorylation status of proteins involved in the tau phosphorylation pathway described above in the mouse brains treated with nifedipine, nifedipine mix and/or T3/T4 as described in Example 10. As shown in FIG. 26, the levels of phosphorylated ROCK (p-ROCK) and GSK-3β (p-GSK-3β) were significantly increased in mice treated with nifedipine or nifedipine mix plus T3/T4. T3/T4 alone also significantly increased the level of p-GSK-3β. The total protein levels of ROCK were not affected by any of the treatment. The level of p-25 was slightly reduced in treated mice. These results indicate that nifedipine, nifedipine mix and/or T3/T4 treatment can lead to reduced Tau phosphorylation in vivo.

Example 18. Effects of Nifedipine and Nitroso-Nifedipine on Glutamate Transport

Figure 27:
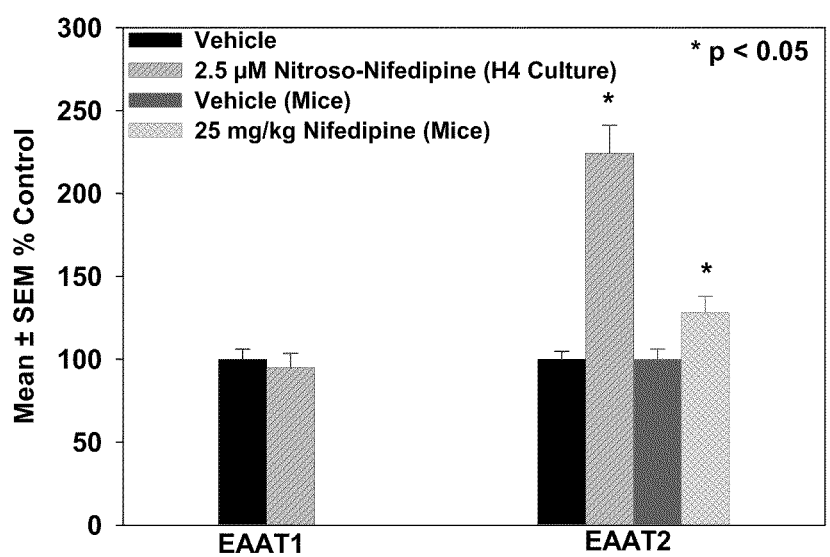
FIG. 27 illustrates exemplary effects of nifedipine and nitroso-nifedipine on glutamate transporter levels.

To test the effect of nitroso-nifedipine on glutamate transport, astroglioma cultures were plated at $2.5 \times 10^5$ cells/well and allowed to attach overnight. The cultures were switched to Opti-MEM and treated with 2.5 μM nitroso-nifedipine for 16 hours. Cultures were washed three times with PBS and fixed with 70% methanol/30% acetone at −20° C. for 30 minutes. Following fixation, cultures were immunostained using antibodies specific to EAAT1 or EAAT2 (Glut-1), the major glutamate transporters. Cultures were then imaged using confocal microscopy and staining intensity quantified using Leica software. 30 to 50 cells were imaged per field and 5 fields were imaged per culture dish. Results of the analyses showed that nitroso-nifedipine led to a significant increase of EAAT2 but no change in EAAT1 (FIG. 27). EAAT2 has been shown to be significantly decreased in AD brain. Using tissue specimens from C57/B16 mice treated acutely for 3 days with 25 mg/kg nifedipine we subjected 20 μg samples of protein to Western blot analysis and probed for EAAT2. Results of the analysis showed a significant increase in EAAT2 with nifedipine. Together, these data suggest that both nifedipine and nitroso-nifedipine lead to increased levels of a key glutamate transporter shown to be altered in AD brain.

Example 19. Liver Toxicity Study

Figure 28:
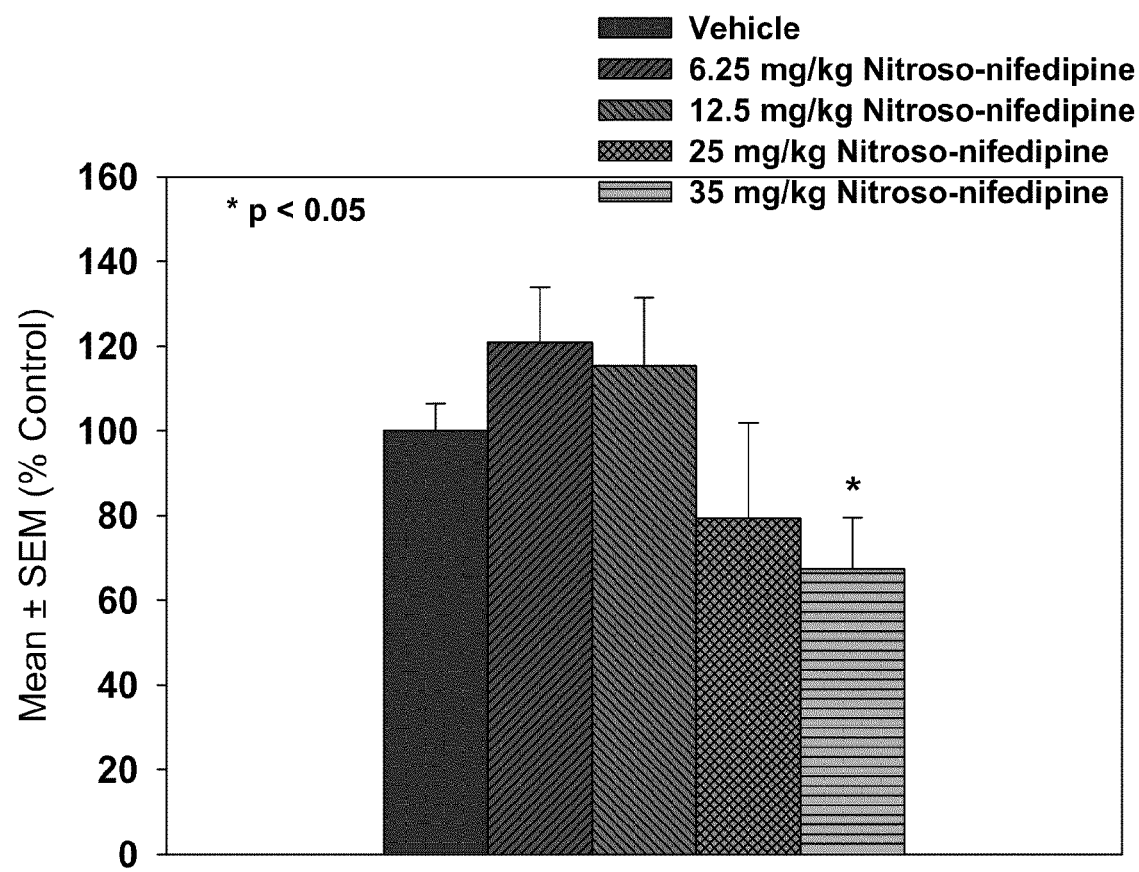
FIG. 28 illustrates exemplary results indicating that nitroso-nifedipine does not induce liver damage in mice.

To determine if treatment with nitroso-nifedipine leads to liver toxicity, alkaline phosphatase levels were quantified in terminal serum samples from mice treated with increasing doses of nitroso-nifedipine using an alkaline phosphatase kit commonly used in clinical practice (Diagnostic Chemicals Limited). Results of the assays showed nitroso-nifedipine did not significantly increase serum alkaline phosphatase levels at any dose and actually led to a significant decrease in levels at a dose of 35 mg/kg (FIG. 28). These data suggest that nitroso-nifedipine does not induce liver damage.

Example 20. Human Association Studies

Figure 29:
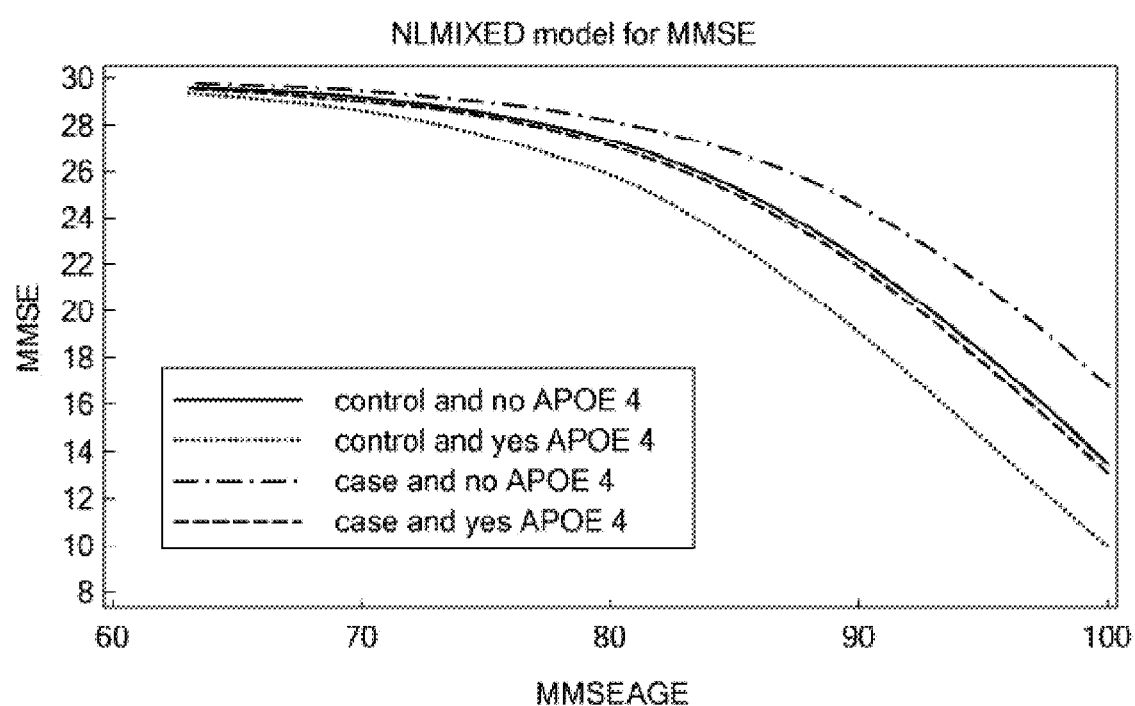
FIG. 29 illustrates exemplary trajectories fitted according to the NLMIXED model of MMSE verse age based on a human association study.

Human association studies were conducted to determine the impact of calcium channel blockers on human patients. In the first study, subjects were segregated into controls, controls with APOE4 (a gene linked to increased incidence of Alzheimer's disease), subjects on dihydropyridine based calcium channel blockers and subjects on dihydropyridine based calcium channel blockers and with APOE4. MMSE (Mini Mental Status Examination) test was used to measure cognitive function of each subject. A trajectory of the fitted model versus age can be determined. FIG. 29 shows exemplary results of the NLMIXED model of MMSE. This model indicates that subjects on calcium channel blockers show a 4 year lag in cognitive decline relative to subjects not on calcium channel blockers.

This human association study demonstrated that the use of dihydropyridine calcium channel blockers appears to delay the onset of cognitive decline, suggesting dihydropyridine calcium channel blockers can be used to treat neurodegenerative diseases such as Alzheimer's disease.

Figure 30:
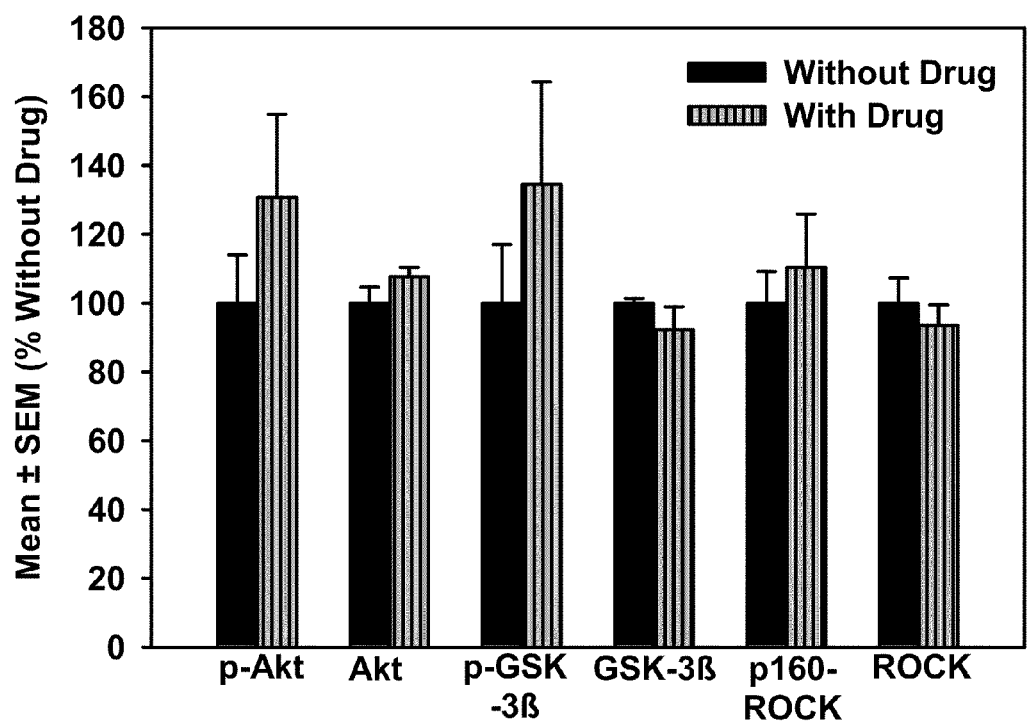
FIG. 30 illustrates exemplary results indicating levels of $A\beta$1-42 and $A\beta$ processing enzymes such as PS-1, Nicas, BACE, APH-1 and PEN-2 in front lobe specimens of subjects from a neuropsychological test score association study who came to autopsy. 4 subjects were on calcium channel blockers, including nifedipine and 4 subjects were not on any calcium channel blocker. $A\beta$ levels determined using Invitrogen ELISAs. Protein levels determined using Western blot analysis and antibodies specific to each protein.

In the second study, we conducted autopsy on a total of 8 subjects from the neuropsychological association study. 4 subjects were on calcium channel blockers, including nifedipine and 4 subjects were not on any calcium channel blocker. Levels of Aβ1-42 and Aβ processing enzymes such as PS-1, Nicas, BACE, APH-1 and PEN-2 in front lobe specimens of subjects were determined using standard methods. Specifically, Aβ1-42 levels were determined using Invitrogen ELISAs and protein levels were determined using Western blot analysis and antibodies specific to each protein. As shown in FIG. 30, the Aβ1-42 level was significantly reduced in subjects with drugs as compared to that in subjects without drugs. Some Aβ processing enzymes including PS-1, Nicas were significantly reduced in those subjects with drugs as compared to those without drugs. Interestingly, the levels of BACE, APH-1 and PEN-2 were increased in those subjects with drugs as compared to subjects without drugs.

Figure 31:
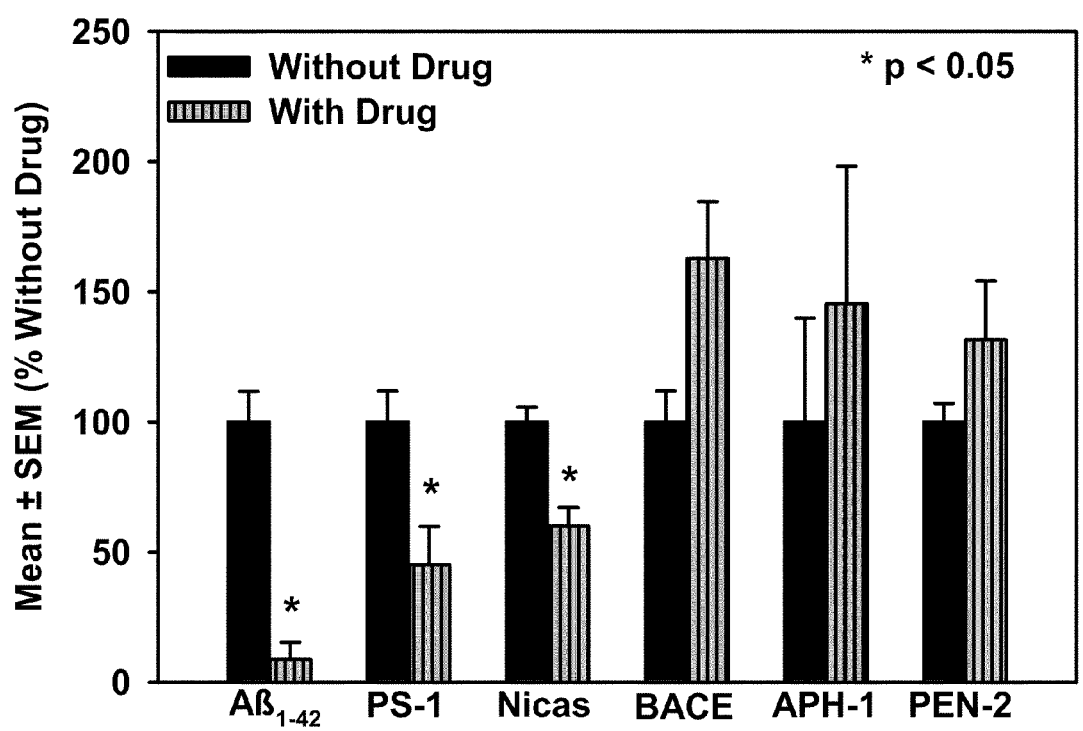
FIG. 31 illustrates exemplary results indicating enzyme levels involved in Tau phosphorylation in frontal lobe specimens from the same subjects shown in FIG. 18.

In addition, enzyme levels that are involved in Tau phosphorylation were also examined in frontal lobe specimens from the subjects. As shown in FIG. 31, the levels of phosphorylated p-Akt, p-GSK-3β and p-ROCK were all increased in subjects with drug as compared to those in subjects without drug. The total protein levels of Akt, GSK-3β and ROCK were comparable in subjects with and without drug. As discussed above, activated p-Akt phosphorylates GSK-3β, which is then inactivated and reduces Tau phosphorylation. These results are consistent with the conclusion that the use of calcium channel blockers can reduce Tau phosphorylation, useful for treatment of Alzheimer's disease.

This human association study demonstrated that the use of calcium channel blockers appears to reduce Aβ1-42 level and certain Aβ1-42 processing enzymes, and inactivate enzymes involved in Tau phosphorylation in human patients, indicating calcium channel blockers may be effective in treating Alzheimer's disease.

Example 21. Nitroso-Nifedipine Increases Calcium Influx

Figure 32:
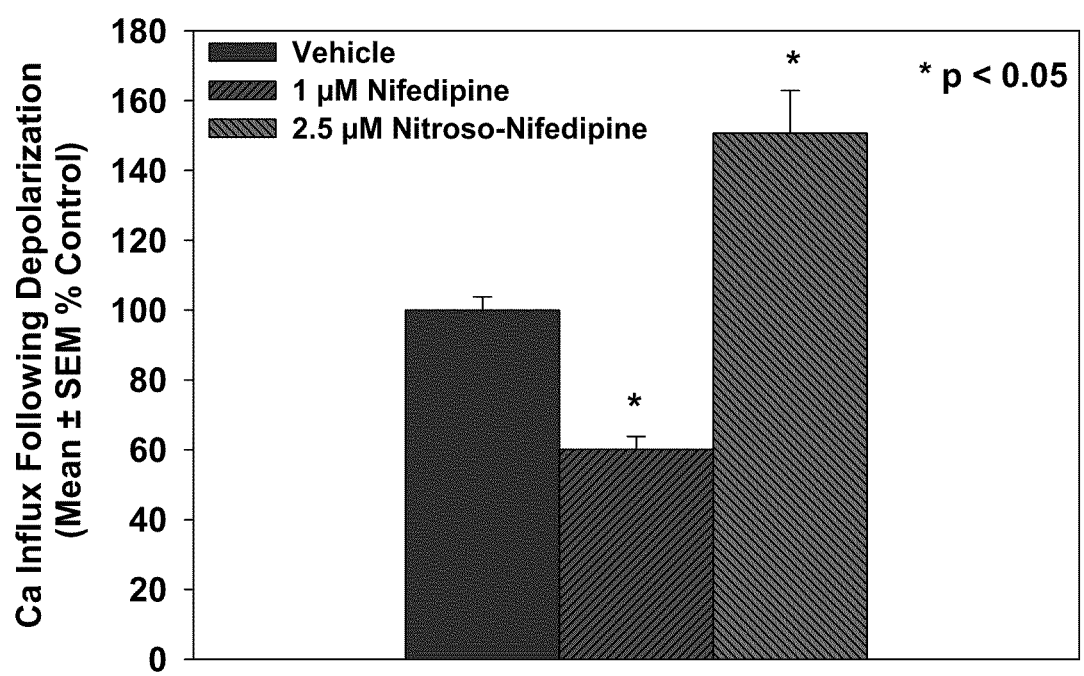
FIG. 32 illustrates exemplary results indicating that treatment of H4 neuroglioma cultures with nitroso-nifedipine leads to a significant increase in calcium influx as compared to control.

This experiment was conducted to determine whether or not nitroso-nifedipine functions as a calcium channel blocker. H4 neuroglioma cultures were loaded with 5 μM Fluo-4 AM for 30 minutes, washed three times with Locke's with glucose and treated with vehicle, 1 μM nifedipine or 2.5 μM nitroso-nifedipine for 1 hour. Cells were depolarized by addition of 40 μL 100 mM KCl and calcium levels quantified 30 seconds following depolarization by confocal microscopy (n=75-100 cells/dish for 3 dishes/treatment). As expected, nifedipine led to a significant decrease in Ca influx following depolarization. In contrast, treatment with nitroso-nifedipine led to a significant increase in Ca influx following depolarization (FIG. 32).

Therefore, this example demonstrates that, unlike nifedipine, nitroso-nifedipine does not function as a calcium channel blocker. Surprisingly, nitroso-nifedipine increases calcium influx. Without wishing to be bound by any theory, it is contemplated that nitroso-nifedipine and its derivatives treat MCI or Alzheimer's disease through a novel mechanism independent of blocking calcium channels.

Example 22. Synthesis of Nitroso-Nifedipine

Figure 33:
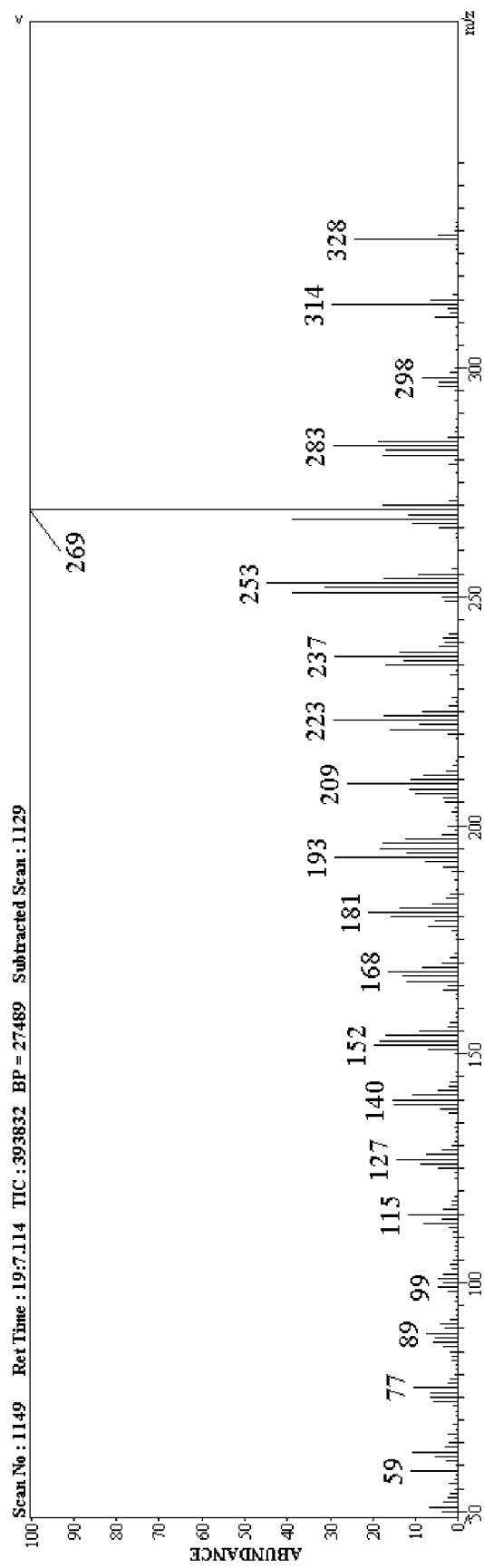
FIG. 33 illustrates exemplary results from a photochemical synthesis of nitroso-nifedipine.

Photochemical synthesis was used in this example to synthesize nitrosonifedipine. Specifically, nifedipine (20 mg) was dissolved in 10 mL acetonitrile in a pyrex culture tube, capped and photolyzed with a 250 W halogen lamp (3M EVW) for 30 minutes. The product was isolated by solvent removal on a rotary evaporator to obtain a blue-green oil (18.1 mg, 94% yield). GC/MS analysis showed greater than 98.5% conversion to nitrosonifedipine. An exemplary result is shown in FIG. 33.

Example 23. Synthesis of NFD-L1

Figure 34:
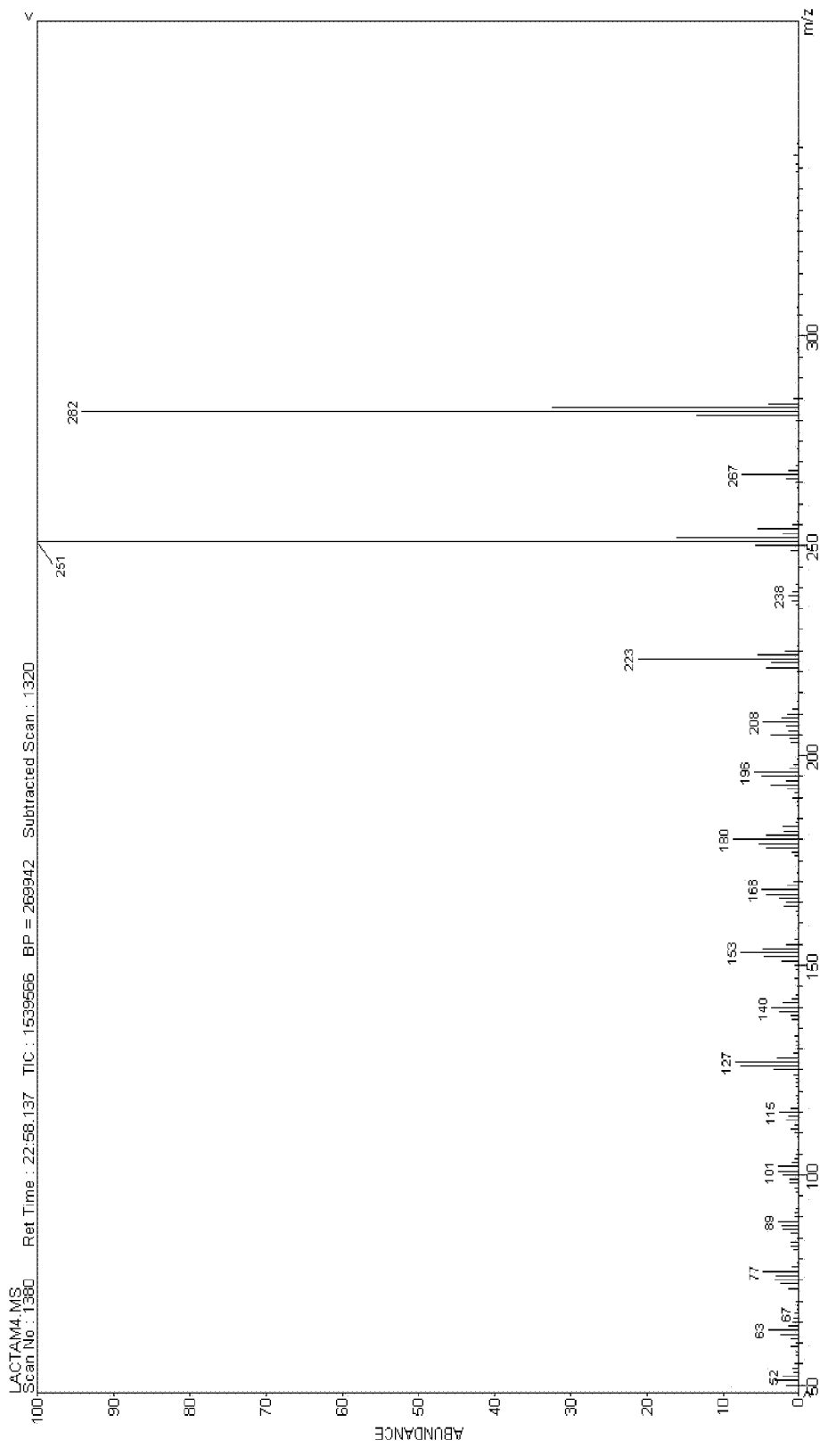
FIG. 34 illustrates exemplary results from a synthesis of NFD-L1.

Nitroso-nifedipine (10 mg, 30.5 µmol) dissolved in 5 mL ethanol was mixed with glutathione (93 mg, 305 µmol) dissolved in 5 mL water and allowed to react at 37° C. for 2 hours. After 2 hours, water was added and the product was extracted with ethyl acetate. The solvent was removed in a rotary evaporator to give NFD-L1 as a white solid in about 85% yield (>95% purity). An exemplary mass spectrum is shown in FIG. 34.

Example 24. Treatment of Human Patients

A human patient determined to have MCI based on an MMSE score is given nitroso-nifedipine at a dosage of 1000 mg per day. Nitroso-nifedipine is given as tablets for oral administration by patient three times daily.

Another human patient determined to have early stage Alzheimer's disease (EAD) based on a CDR score is given nitroso-nifedipine at a dosage of 800 mg per day. Nitroso-nifedipine is given as tablets for oral administration by patient three times daily.

A human patient determined to have MCI based on the level of PDS/TTR complex in a fluid sample obtained from the patient is given nitroso-nifedipine at a dosage of 1000 mg per day. Nitroso-nifedipine is given as tablets for oral administration by patient four times daily.

EQUIVALENTS

The foregoing has been a description of certain non-limiting embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description are introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

INCORPORATION OF REFERENCES

All publications and patent documents cited in this application are incorporated by reference in their entirety to the same extent as if the contents of each individual publication or patent document were incorporated herein.

What is claimed is:

1. A method for treating Mild Cognitive Impairment (MCI) or Alzheimer's disease in a human subject, the method comprising
administering to a subject who is suffering from or susceptible to Mild Cognitive Impairment (MCI) or Alzheimer's disease a therapeutically effective amount of a lactam such that at least one symptom or feature associated with Mild Cognitive Impairment (MCI) or Alzheimer's disease is reduced in abundance, intensity, severity, or frequency, or has delayed onset; and wherein the lactam is NFD-L1,

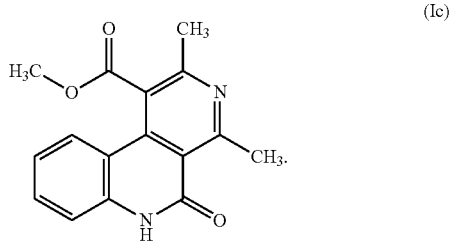 [SMILES: COC(=O)c1c(C)nc(C)c2c(=O)[nH]c3ccccc3c12]

(Ic)

2. The method of claim 1, wherein the at least one symptom or feature is the production of amyloid beta protein.

3. The method of claim 1, wherein the at least one symptom or feature is gamma-secretase activity, and wherein the gamma-secretase activity is reduced by inhibiting orphan G-coupled receptor 3 (GPCR-3) activity.

4. The method of claim 1, wherein the at least one symptom or feature is phosphorylated tau protein in the brain.

5. The method of claim 1, wherein the subject has an abnormal level of a biomarker as compared to a control, wherein the biomarker comprises:
at least one of a transthyretin protein and/or a prostaglandin-H2 D-isomerase protein, and
at least one second, different protein selected from a transthyretin, prostaglandin-H2 D-isomerase, beta-2-microglobulin, cystatin C, superoxide dismutase [Cu—Zn], plasma retinol-binding protein, phosphatidylethanolamine-binding protein, carbonic anhydrase 2, and/or serotransferrin protein.

6. The method of claim 5, wherein the biomarker comprises prostaglandin-D2-synthase and transthyretin (PDS/TTR complex).

7. The method of claim 1, wherein the subject has an abnormal level of a biomarker as compared to a control, wherein the biomarker comprises one or more of (i) beta amyloid 40 (Aβ40), (ii) beta amyloid 42 (Aβ42), (iii) the ratio of Aβ40 to Aβ42, and (iv) the ratio of phosphorylated tau to total tau.

8. The method of claim 1, wherein the subject has a test score indicative of cognitive impairment.

9. The method of claim 8, wherein the test score is an MMSE (Mini Mental Status Examination) score.

10. The method of claim 9, wherein the MMSE score ranges from 21-26.

11. The method of claim 8, wherein the test score is a clinical dementia rating (CDR) score.

12. The method of claim 11, wherein the CDR score is 0.5 or 1.

13. The method of claim 1, further comprising administering a therapeutic amount of nitroso-nifedipine to the subject.

14. The method of claim 1, further comprising administering a mixture of nitrosonifedipine and oxidized nifedipine to the subject.

15. The method of claim 14, wherein the mixture further comprises triiodothyronine (T3) and thyroxine (T4).

16. The method of claim 14, wherein the mixture further comprises nifedipine.

17. The method of claim 16, wherein the mixture comprises 55% nitroso-nifedipine, 11% oxidized nifedipine, and 34% nifedipine.

18. The method of claim 16, wherein the mixture further comprises triiodothyronine (T3) and thyroxine (T4).

19. The method of claim 13, wherein the therapeutically effective amount of nitrosonifedipine ranges from about 10 mg to about 2.5 g per dose.

20. The method of claim 1, further comprising administering a mixture of triiodothyronine (T3) and thyroxine (T4) to the subject.

21. The method of claim 20, wherein the mixture further comprises nifedipine.

22. The method of claim 1, wherein the lactam does not function as a calcium channel blocker.

* * * * *